(12) United States Patent
Jones

(10) Patent No.: US 9,314,541 B2
(45) Date of Patent: *Apr. 19, 2016

(54) IN VIVO IMAGING METHOD FOR CANCER

(75) Inventor: Paul Alexander Jones, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/822,450

(22) PCT Filed: Sep. 29, 2011

(86) PCT No.: PCT/EP2011/066970
§ 371 (c)(1),
(2), (4) Date: Mar. 12, 2013

(87) PCT Pub. No.: WO2012/041953
PCT Pub. Date: Apr. 5, 2012

(65) Prior Publication Data
US 2013/0183240 A1    Jul. 18, 2013

Related U.S. Application Data

(60) Provisional application No. 61/387,998, filed on Sep. 30, 2010.

(30) Foreign Application Priority Data

Sep. 30, 2010 (GB) .................................. 1016411.9

(51) Int. Cl.
*A61K 51/00* (2006.01)
*A61K 36/14* (2006.01)
*A61K 51/04* (2006.01)

(52) U.S. Cl.
CPC ........... *A61K 51/0446* (2013.01); *A61K 51/041* (2013.01); *A61K 51/0455* (2013.01); *A61K 51/0468* (2013.01)

(58) Field of Classification Search
CPC .............. A61K 51/00; A61K 51/0446; A61K 51/0455; A61K 51/0468
USPC .......... 424/1.11, 1.89, 9.1; 548/418, 421, 448
See application file for complete search history.

(56) References Cited

U.S. PATENT DOCUMENTS 8,501,153 B2 *   8/2013   Achanath et al. ............ 424/1.11

FOREIGN PATENT DOCUMENTS

| WO | 2007/057705 | 5/2007 |
| WO | 2010/037851 | 4/2010 |
| WO | 2010/049819 | 5/2010 |
| WO | 2010/109007 | 9/2010 |
| WO | 2011/117421 | 9/2011 |

OTHER PUBLICATIONS

Darryl J. Bornhop et al. Targeted Molecular Imaging Agents for Cellular-Scale Bimodal Imaging, Bioconjugate Chem, 2004, 15, 1488-1495.*
Homes, Bioorganic & Medicinal Chemistry, vol. 14, No. 11, Jun. 1, 2006, pp. 3939-3946.
Taliani, et.al. Current Topics in Medicinial Chemistry 2011 Bentham Sicience Publishers, B.V. vol. 11, No. 7, Apr. 7, 2011 pp. 860-886.
Vlodavsky, etl. al. Journal of Neuro-Oncology, Kluwer Academic Publishers, 80, vol. 81, No. 1, Jul. 26, 2006 pp. 1-7.

* cited by examiner

*Primary Examiner* — Michael G Hartley
*Assistant Examiner* — Jagadishwar Samala

(57) ABSTRACT

The present invention provides a method useful in the diagnosis and monitoring of cancer wherein there is an abnormal expression of PBR. The method of the invention is particularly useful in evaluating the severity of the cancer, e.g. PBR expression correlates with cell proliferation rates, metastatic potential, tumor aggressiveness, malignancy progression. The method of the invention can therefore be applied in the determination of likely disease progression and in making an associated prognosis. Furthermore, the method of the invention can find use in determining the likely success of certain therapeutic approaches, or in the evaluation of the efficacy of certain proposed new treatments.

15 Claims, 29 Drawing Sheets

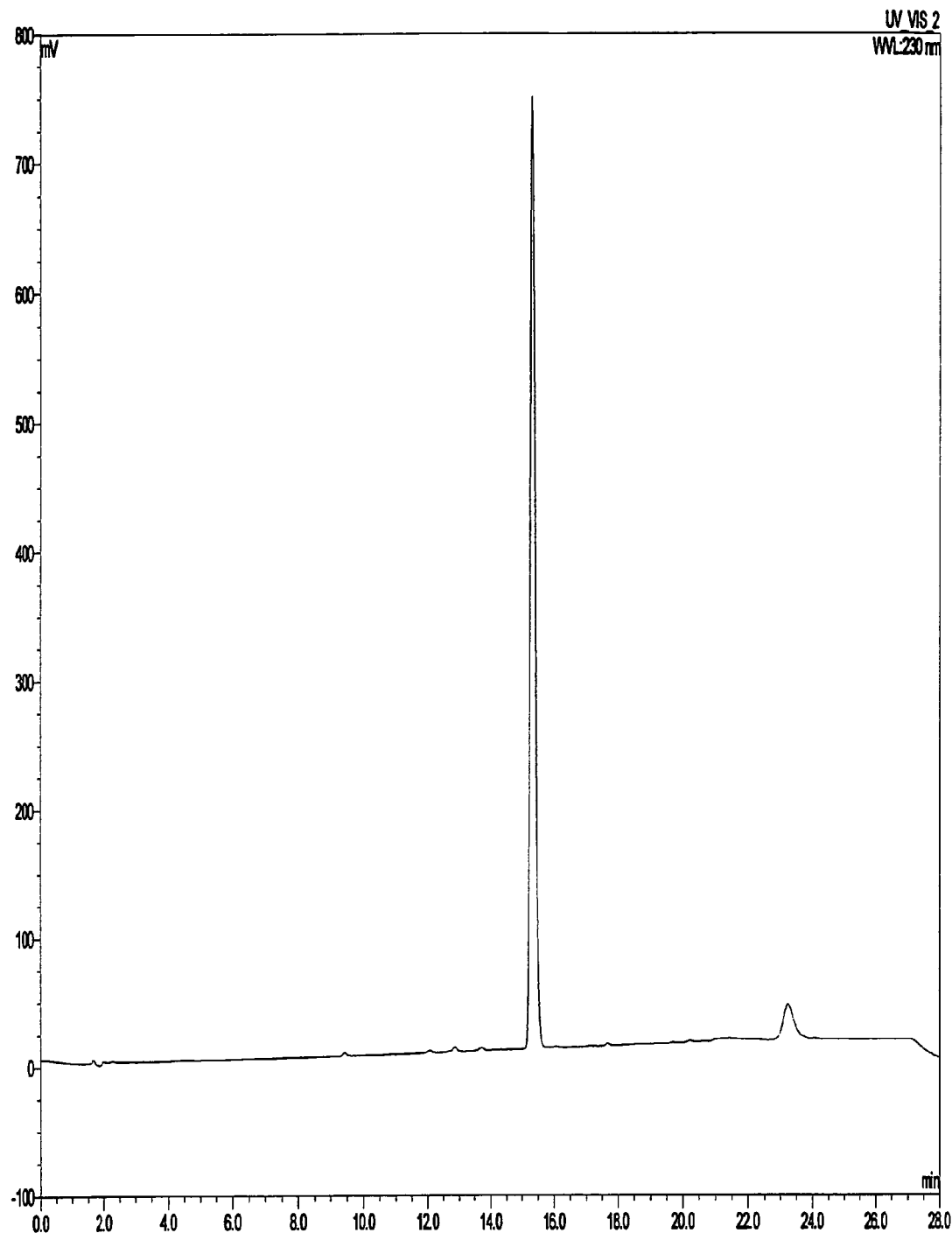
Figure 1 (cont...)

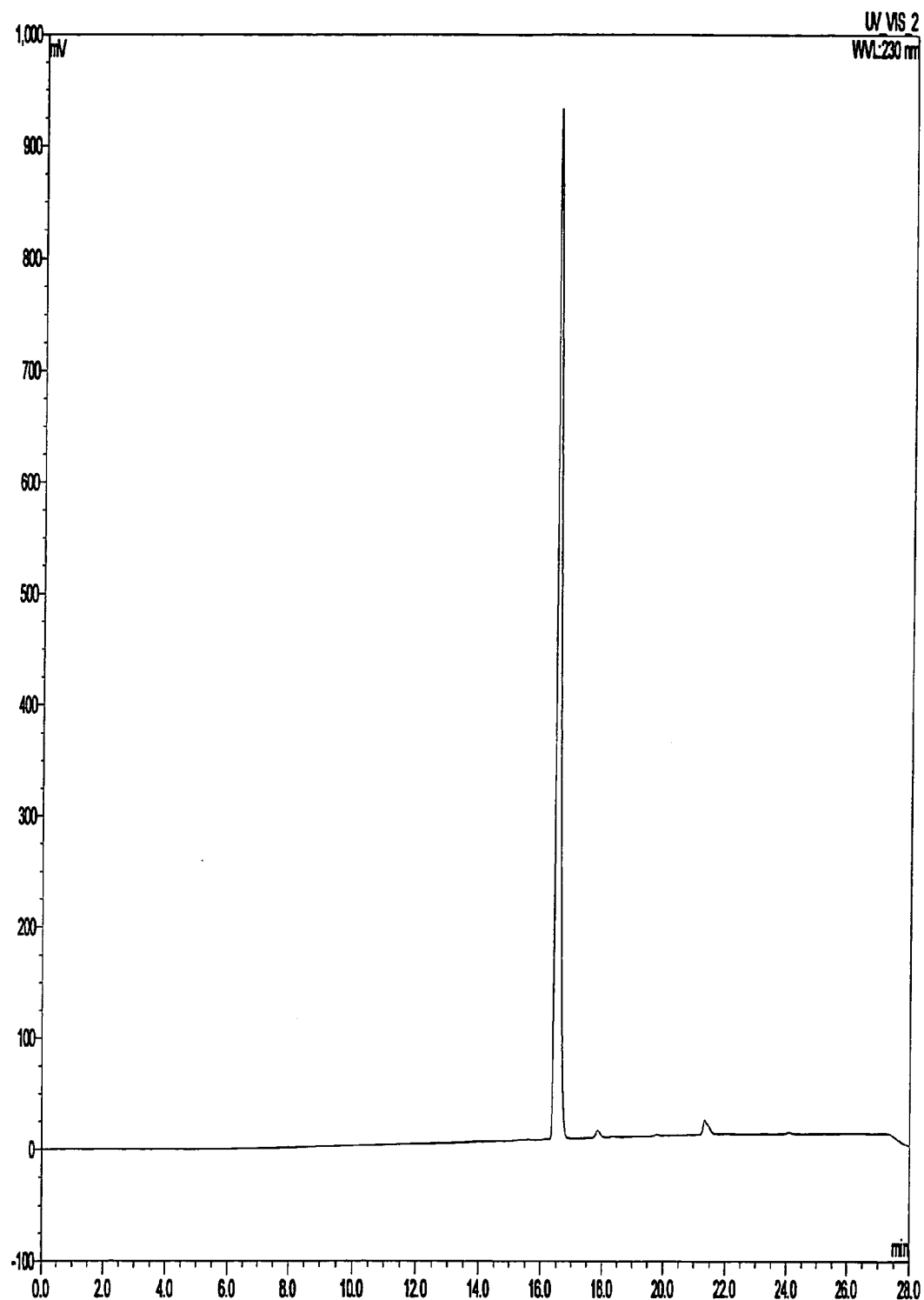
Figure 2 (cont...)

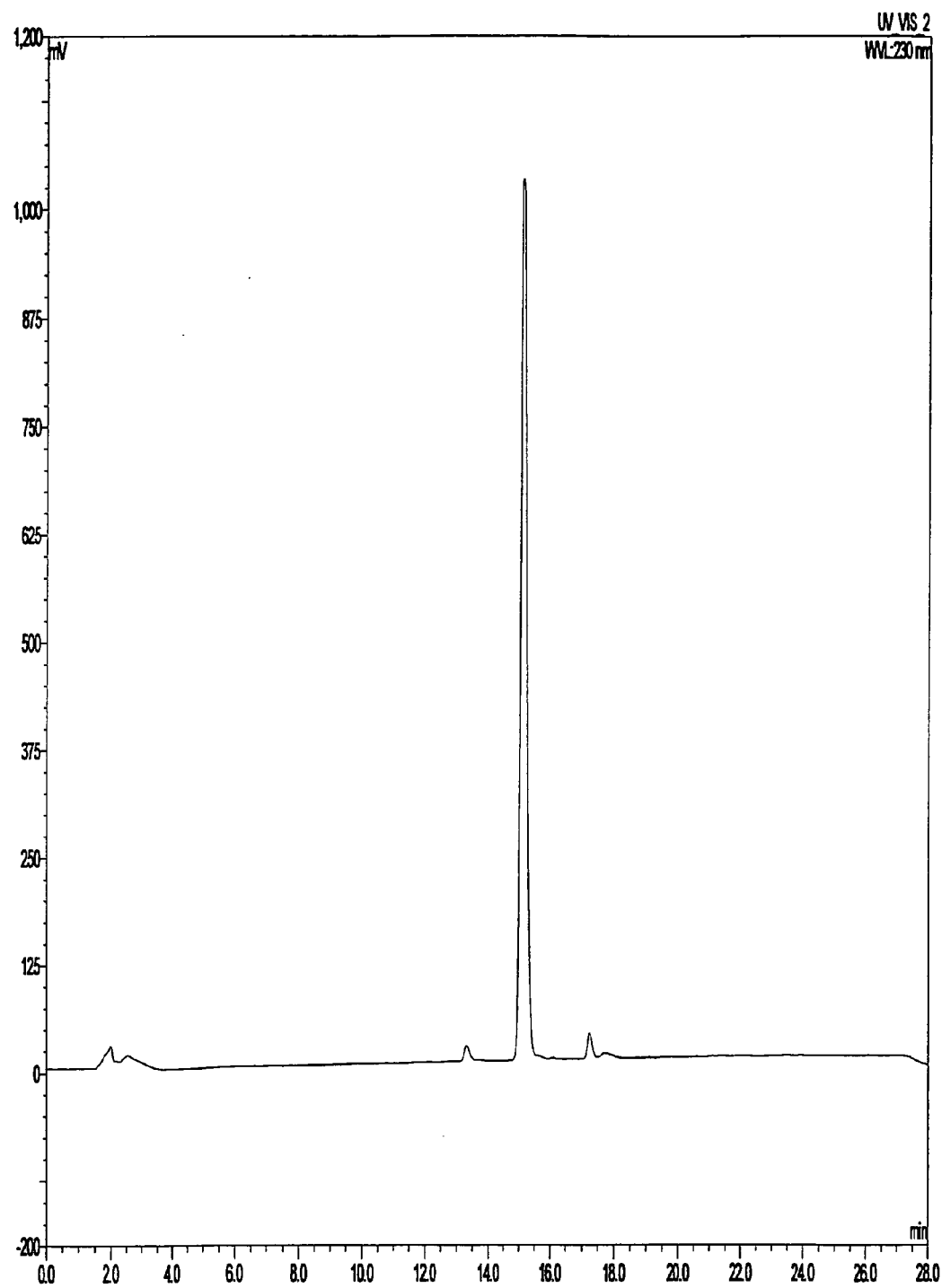
Figure 3 (cont...)

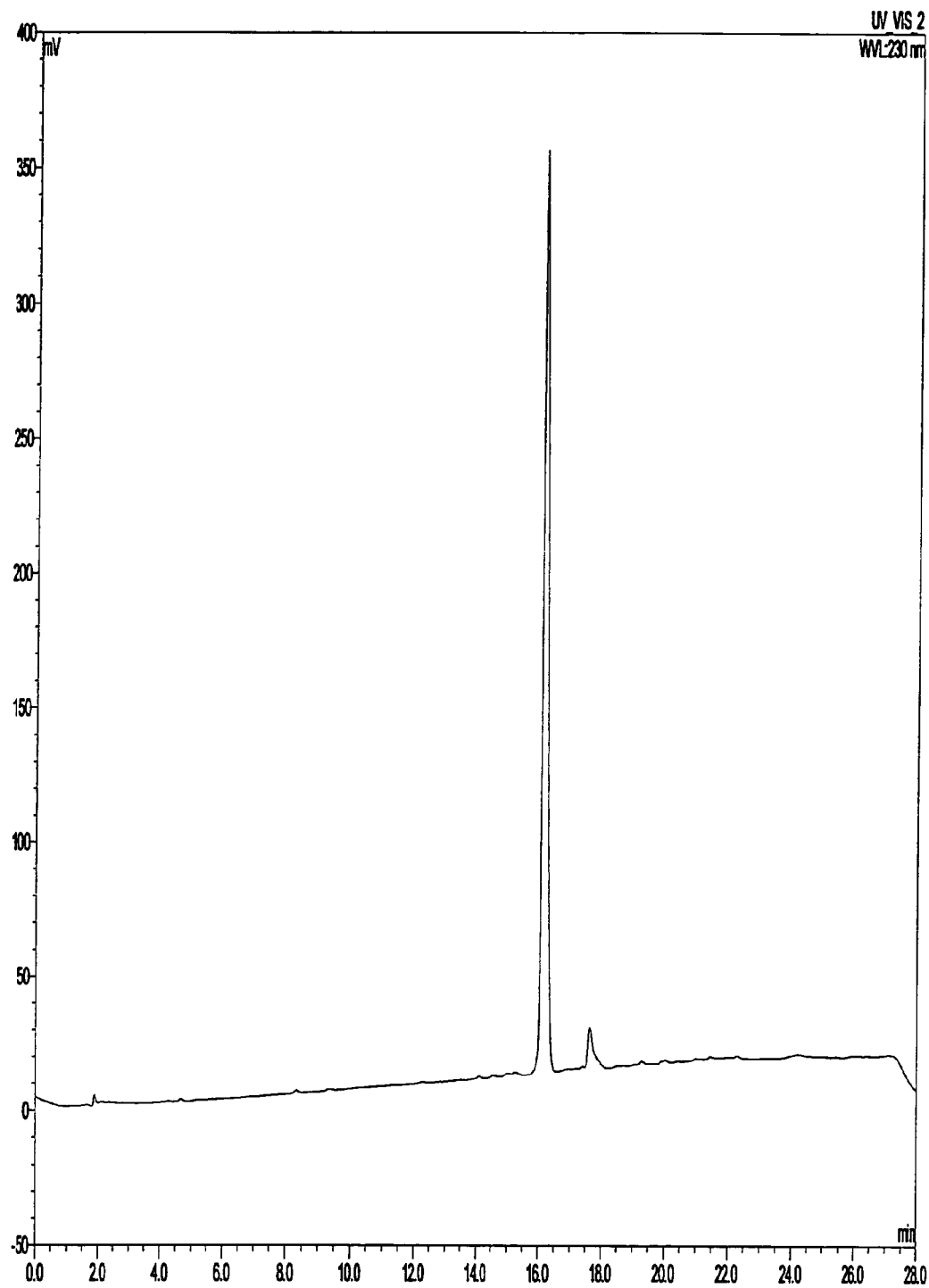
Figure 4 (cont...)

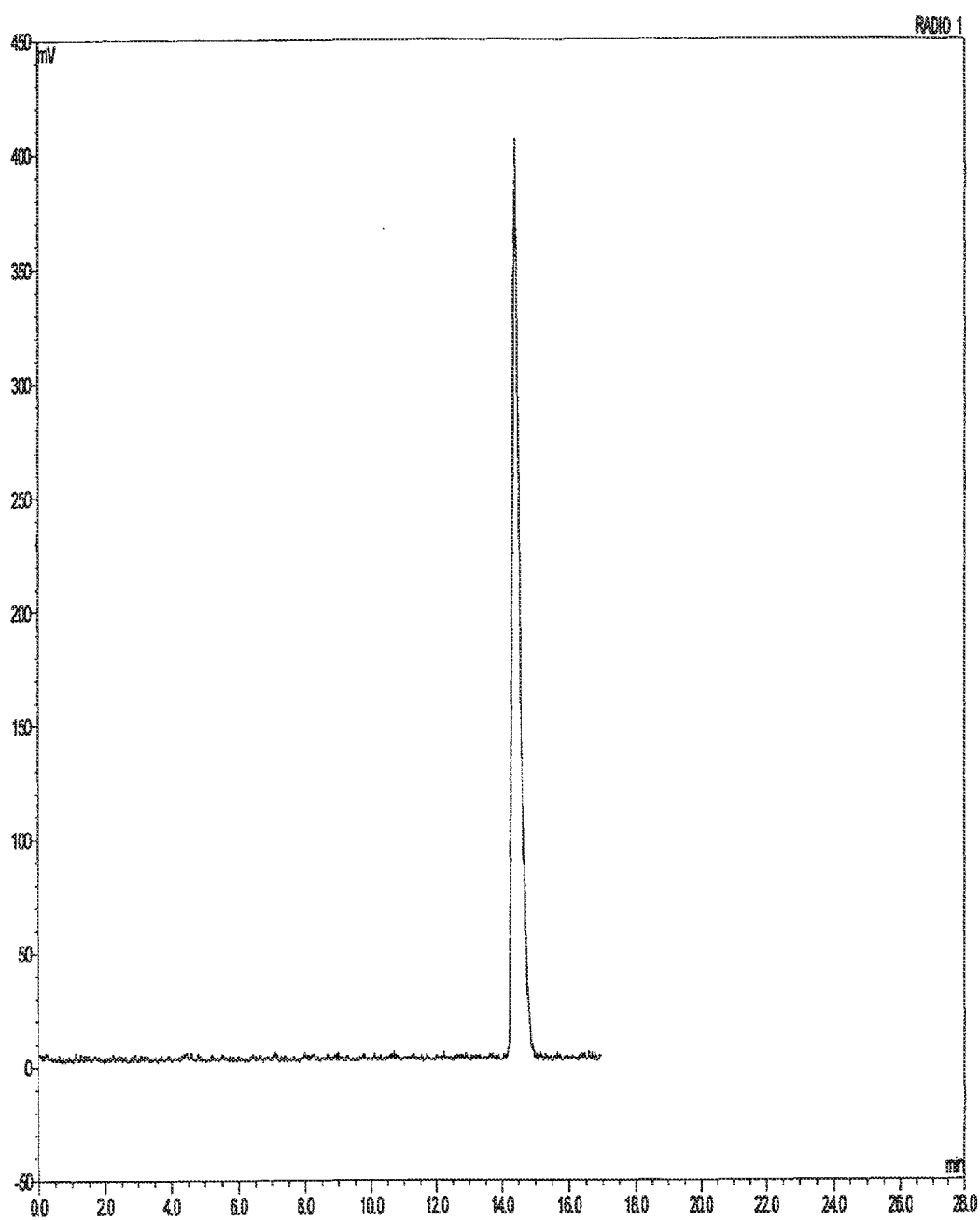
Figure 5 (continued...)

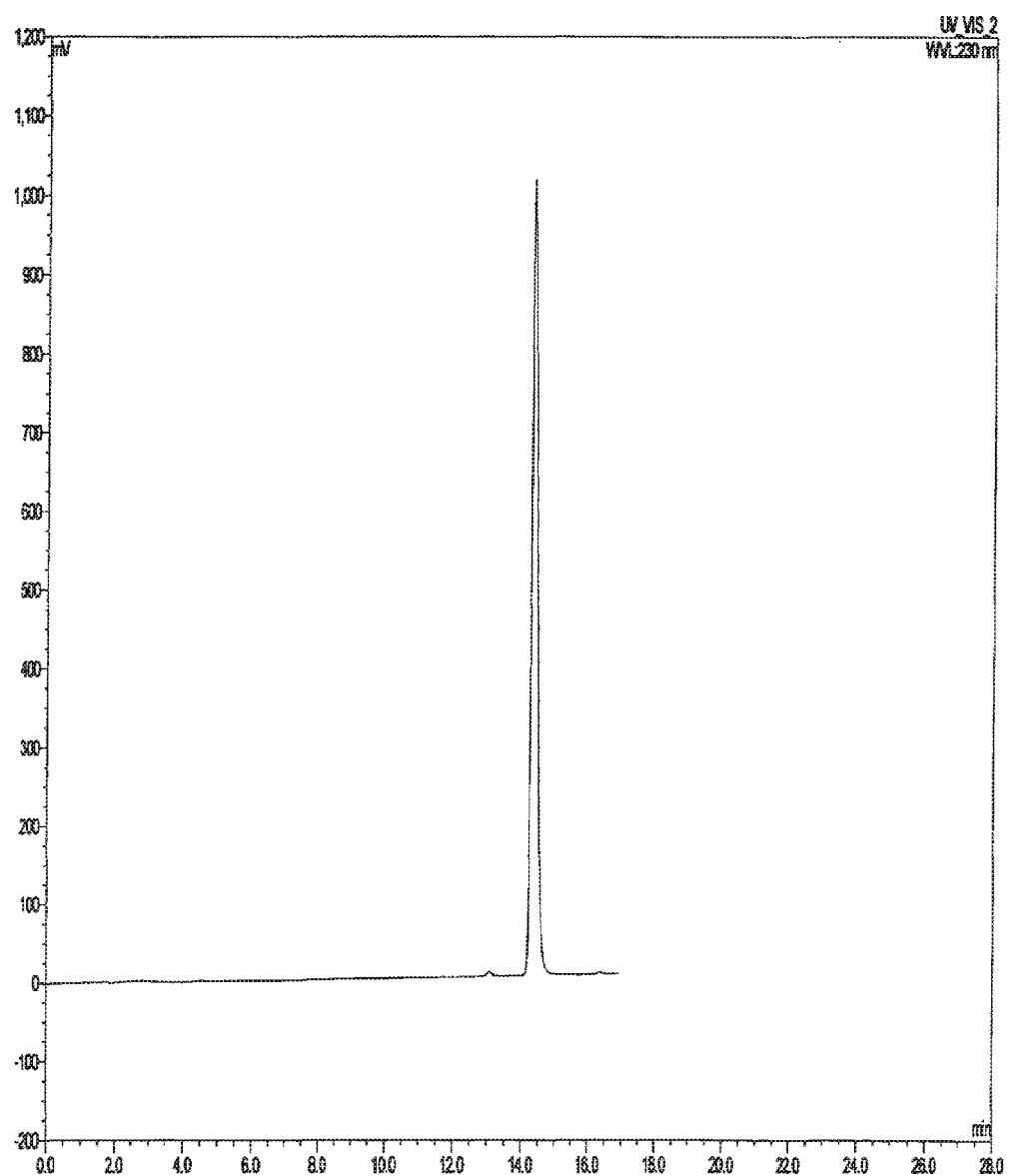
Figure 5 (continued...)

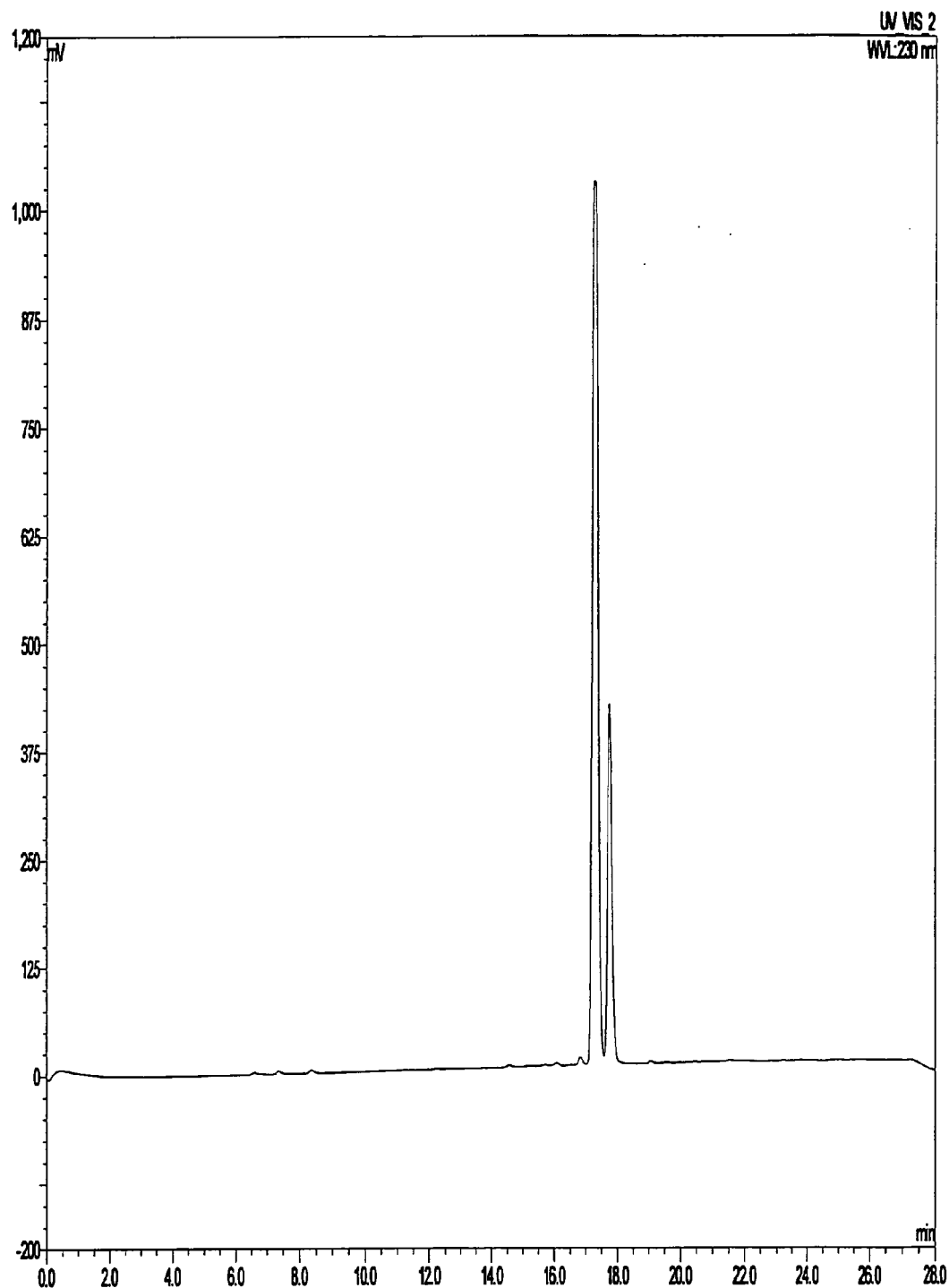
Figure 6 (cont...)

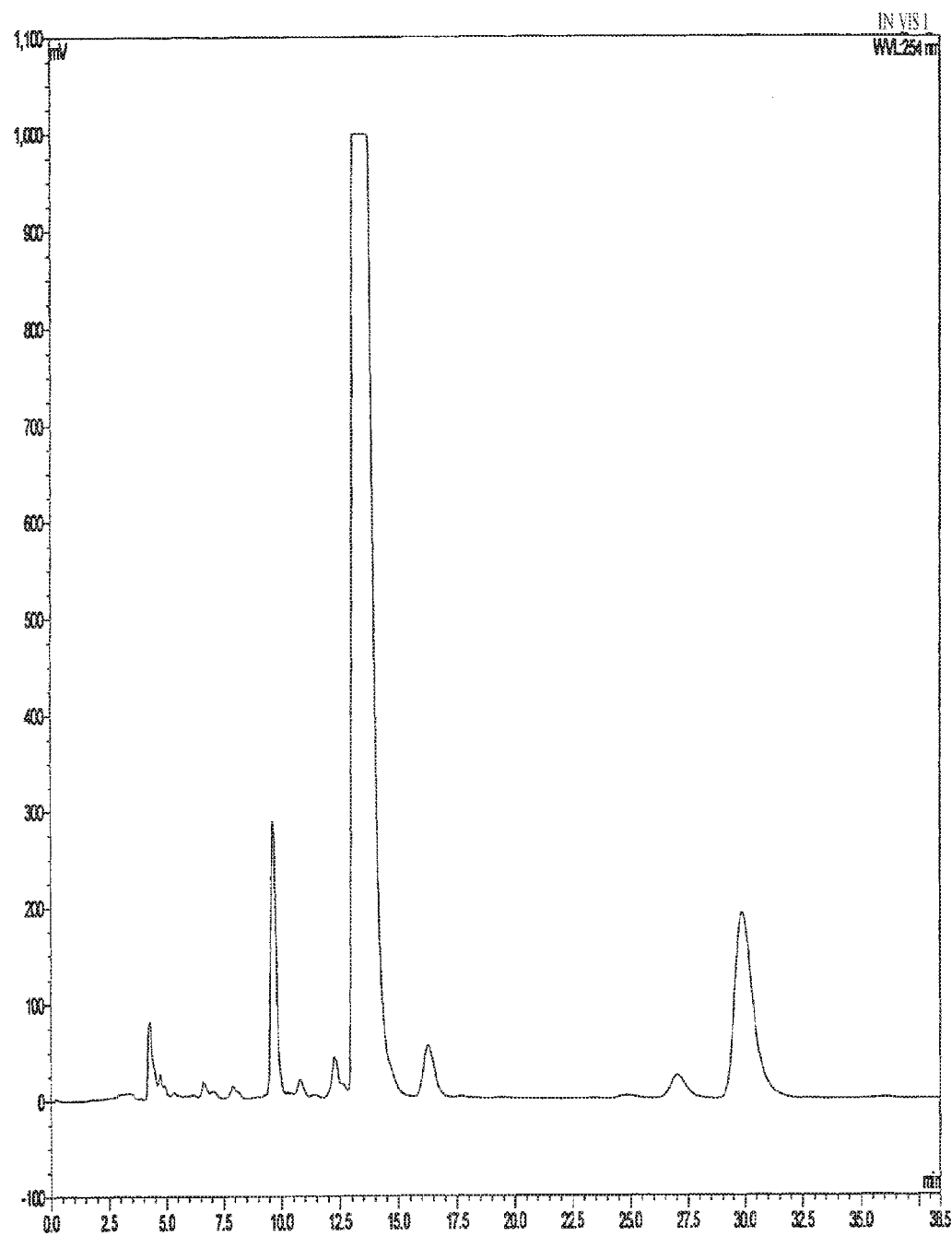
Figure 7 (continued...)

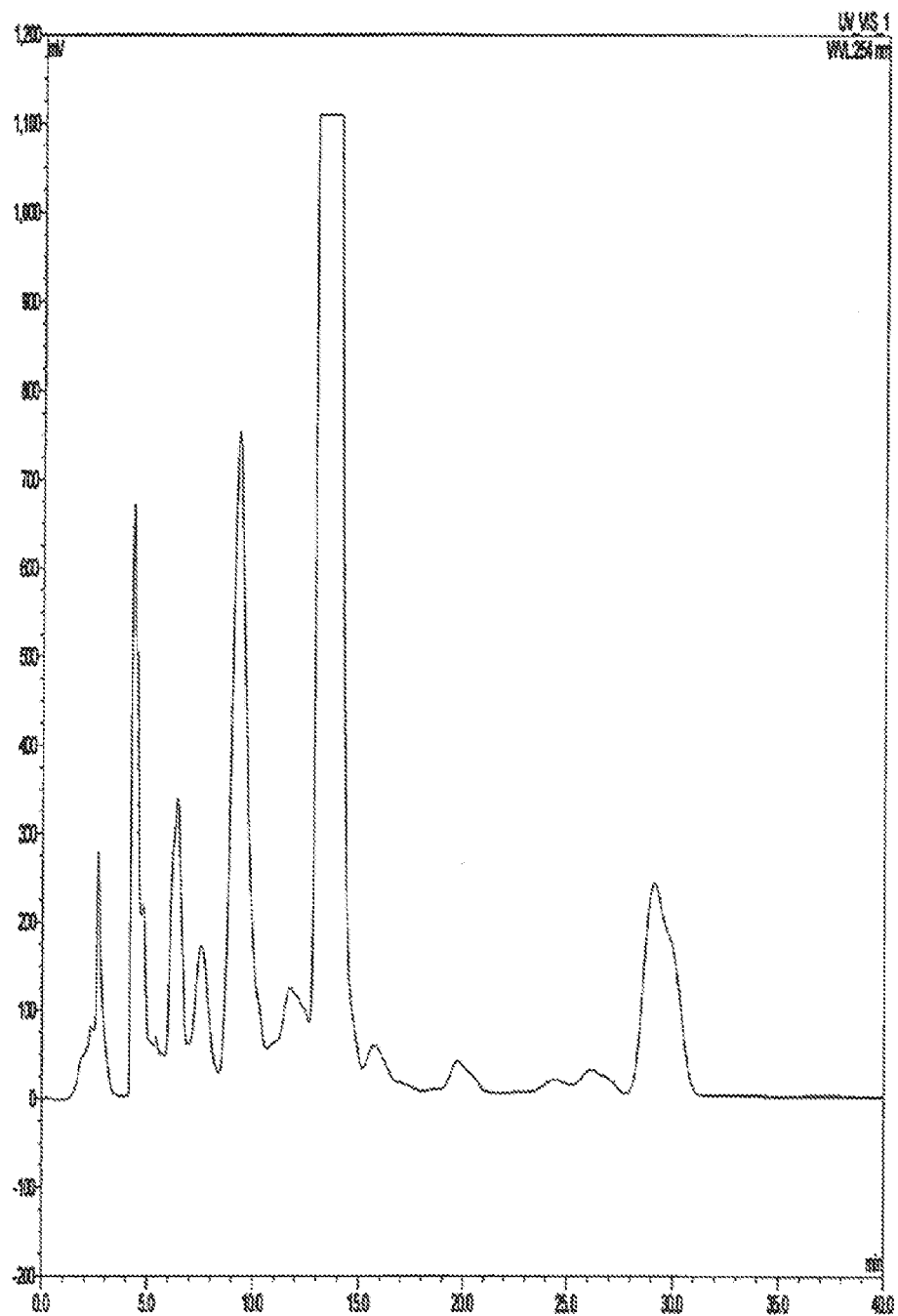
Figure 8 (continued...)

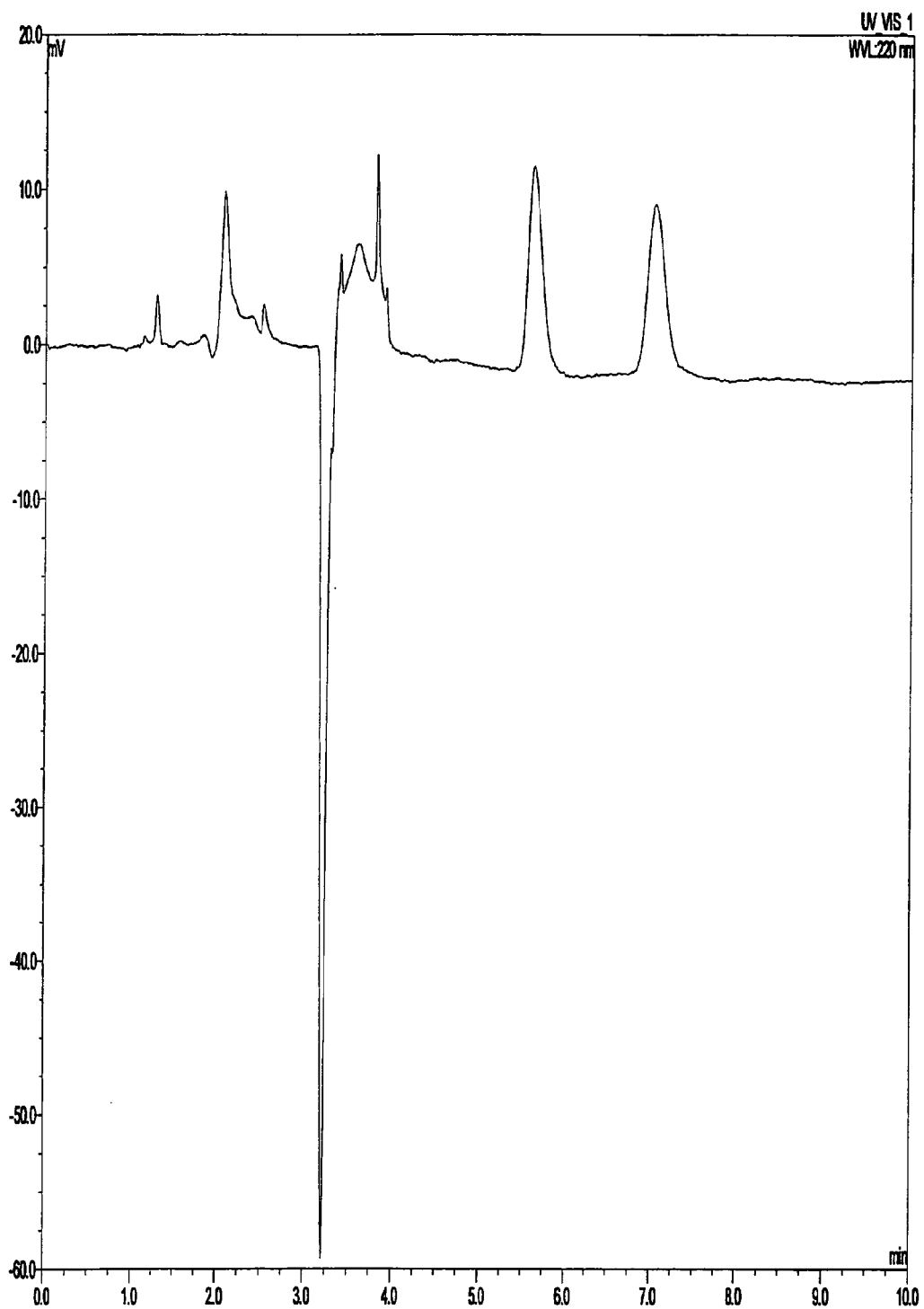
Figure 11 (cont...)

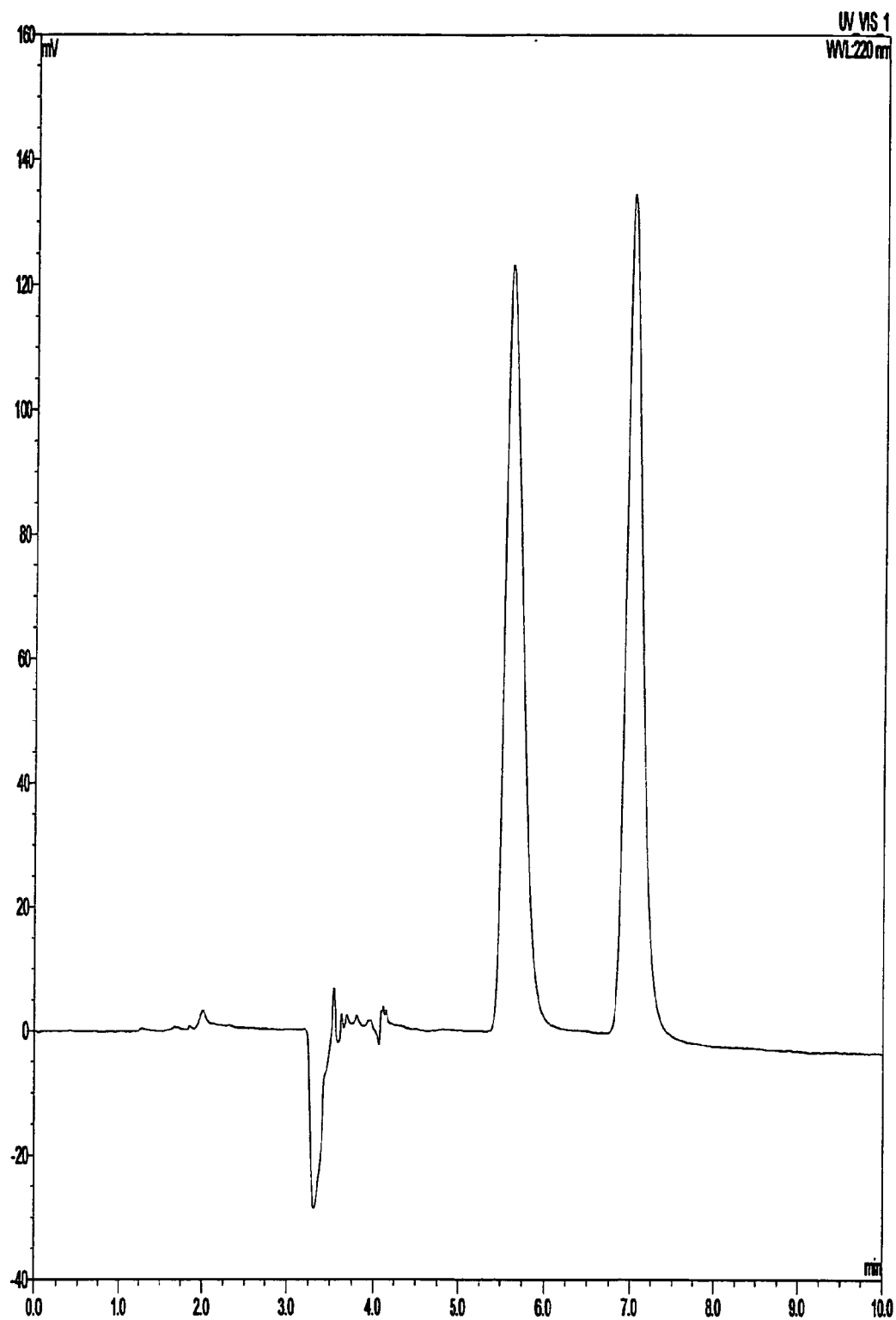
Figure 12 (cont...)

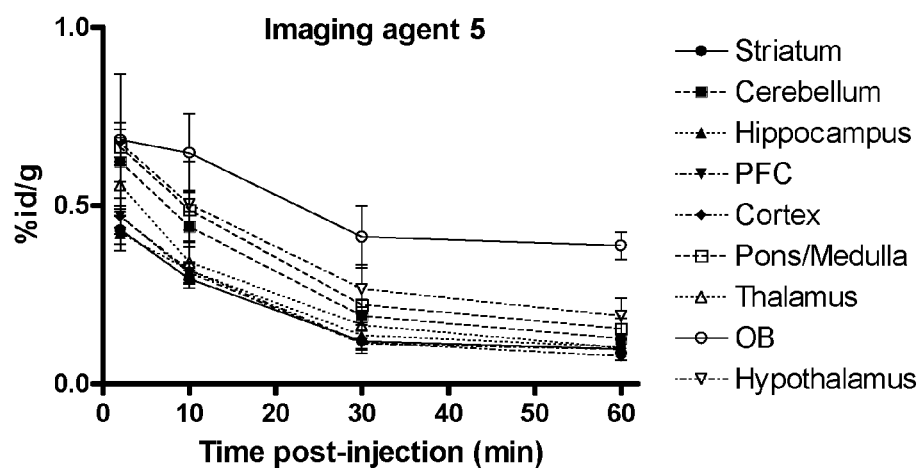
Figure 13: Brain biodistribution of imaging agent 5

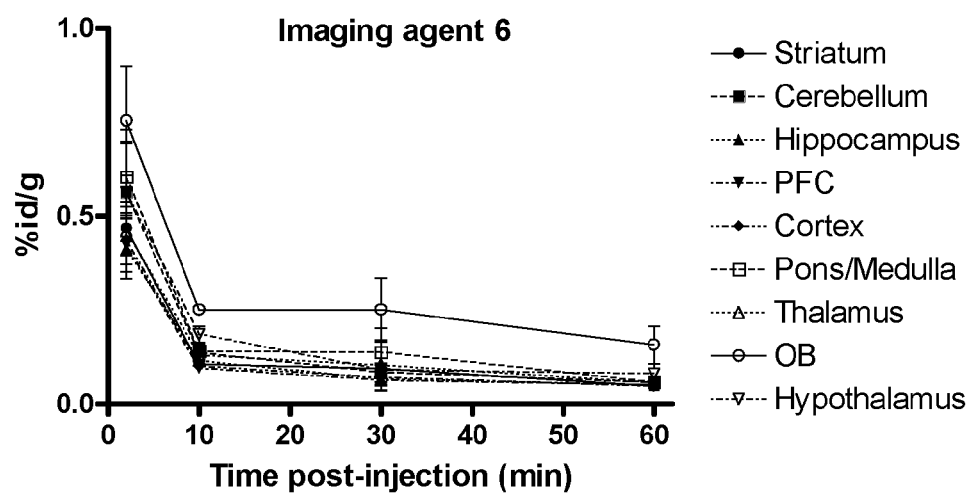
Figure 14: Brain biodistribution of imaging agent 6

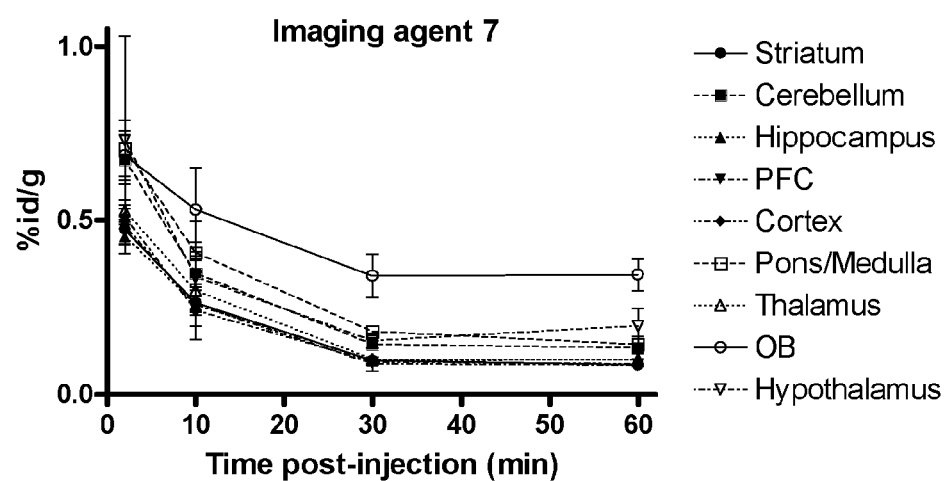
Figure 15: Brain biodistribution of imaging agent 7

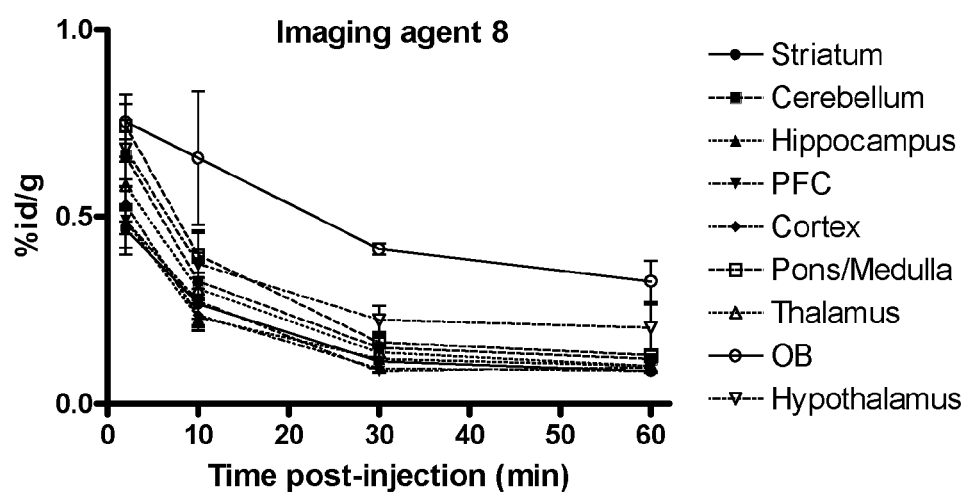
Figure 16: Brain biodistribution of imaging agent 8

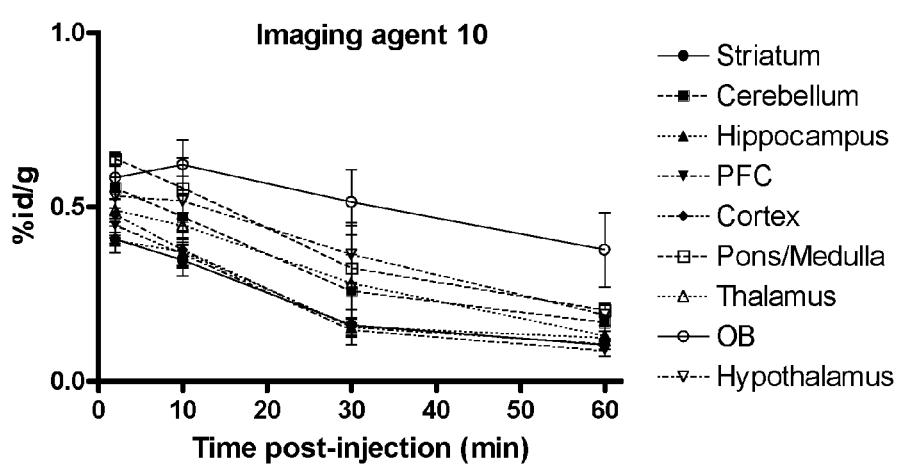
Figure 17: Brain biodistribution of imaging agent 10

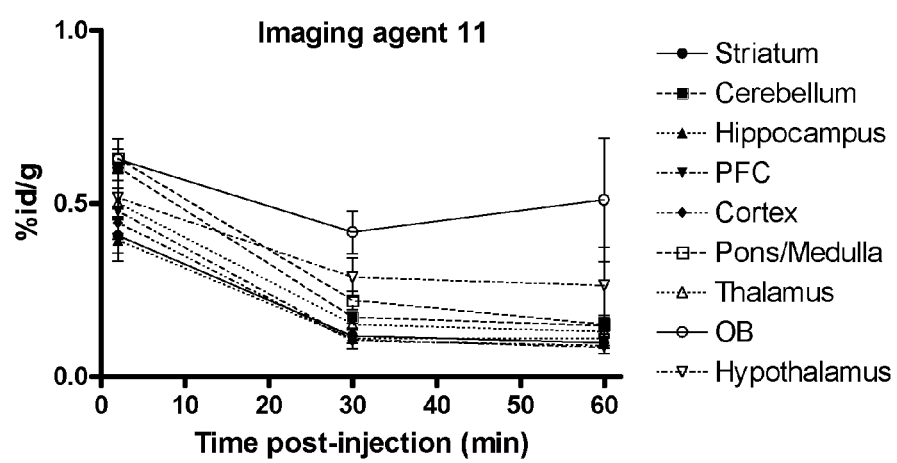
Figure 18: Brain biodistribution of imaging agent 11

IN VIVO IMAGING METHOD FOR CANCER

This application is a filing under 35 U.S.C. 371 of international application number PCT/EP2011/066970, filed Sep. 29, 2011, which claims priority to Great Britain application number 1016411.9 filed Sep. 30, 2010 and U.S. application No. 61/387,998 filed Sep. 30, 2010, the entire disclosure of each of which is hereby incorporated by reference.

TECHNICAL FIELD OF THE INVENTION

The present invention concerns in vivo imaging and in particular in vivo imaging of the peripheral benzodiazepine receptor (PBR). In particular, the present invention provides a method useful for the diagnosis and monitoring of cancer.

DESCRIPTION OF RELATED ART

The peripheral benzodiazepine receptor (PBR, also known as translocator protein (TSPO)) is a mitochondrial protein involved in cell proliferation. PBR is known to be mainly localised in peripheral tissues and glial cells but its physiological function remains to be clearly elucidated. Subcellularly, PBR is known to localise on the outer mitochondrial membrane, indicating a potential role in the modulation of mitochondrial function and in the immune system. It has furthermore been postulated that PBR is involved in cell proliferation, steroidogenesis, calcium flow and cellular respiration.

A link has been observed between PBR expression and cancer pathophysiology. In glioma cell lines, a high correlation between PBR density and both enhanced tumourgenicity and cell proliferation rates (Veenman et al Biochem Pharmacol 2004; 68: 689-98) and metastatic potential of the cancer (Rechichi et al Biochim Biophys Acta 2008; 1782: 118-25) has been characterised. In an animal model of mammary tumours, the total expression of PBR ($B_{max}$ of [$^3$H]Ro5-4864) increased by 56% in non-aggressive tumours, but considerably more (128%) in aggressive tumours (Mukhopadhyay et al Glycoconj J 2006; 23: 199-207). Similarly, Hunakova et al (Neoplasma 2007; 54: 541-8) correlated PBR expression with tumour aggressiveness in breast as well as ovarian carcinoma cell lines. They showed little correlation with mitochondrial concentration, but a very strong correlation with malignancy progression. High PBR density was also shown to be a significant differential marker between cisplatin-sensitive and insensitive ovarian carcinoma cell lines. A direct link between PBR and tumour aggression was shown in glioma cells over-expressing the receptor that exhibited potentiated proliferation, motility and transmigration capability compared to wild type cells (Rechichi et al Biochim Biophys Acta 2008; 1782: 118-25). Zheng et al (Mol Pharmaceutics 2011; 8: 823-2) found using immunohistochemistry that a significant portion of tumour stromal PBR expression colocalised with F4/80 positive macrophage cells. Knockdown of PBR expression by siRNA in the highly aggressive MDA-MB-231 breast cancer cell line lead to a reduction in cell proliferation (Li et al Biochem Pharmacol 2007; 73: 491-503). These studies suggest that the link between tumour aggression and PBR expression is a direct pathophysiological one and not secondary or epiphenomenal. This furthermore suggests that successful treatment is likely to be mirrored by a decrease in expression, a finding observed in breast, glioma and hepatocarcinoma cells lines (Pretner et al Anticancer Res 2006; 26: 9-22).

The above-described in vitro observations have been mirrored in vivo, firming the link between PBR, tumour aggressiveness and patient survival. Maaser et al (Clin Cancer Res. 2002; 8: 3205-9) examined resected stage III colorectal carcinomas histologically. Subdividing patients into 'high' and 'low' PBR expression groups the authors showed a differentiated mean survival of 30 months and concluded that PBR overexpression was an independent prognostic factor for this cancer. Miettnen et al (Cancer Res 1995; 55: 2691-5) showed a tight correlation between the severity grade of 86 astrocytic brain tumours and intensity of PBR expression ($P<0.0012$), such that of the 37 Grade IV tumours (the most severe) 86% had 'moderate or greater' expression of PBR and 64% exhibited 'very high' expression. In contrast, of the 9 Grade I tumours 66% had 'little or no' PBR expression and none had 'very high' expression. A clear correlation was also observed between PBR expression and proliferative index (as ascertained by Ki-67 immunohistochemistry). Analysing patient survival of the 'low or no expression' groups with 'moderate to very high expression' groups significantly linked PBR expression to poorer outcome. Similarly, Vlodavsky & Soustiel (J Neurooncol 2007; 81: 1-7) correlated PBR expression negatively to survival and positively to tumour malignancy, proliferation and apoptotic indices.

In breast cancer, Galiegue et al, (Clin Cancer Res 2004; 10: 2058-64) showed that PBR was increased in tumoral cells compared to normal tissue, with a tight correlation to the proliferation marker, Ki-67. By analysing the survival of 'high' and 'low' expressing groups, the authors also suggest the usefulness of PBR as a prognostic marker for lymph node-negative patients.

In a study of patients suffering from oral cancer, Nagler et al (Biochim Biophys Acta 2010; 1802(5): 454-61) demonstrated a direct correlation between increased PBR expression and decreased survival time. Five-year survival probability dropped from 65% in patients with PBR negative tumors to 7% in patients with highly expressed PBR ($p<0.001$).

Fafalios et al (Clin Cancer Res 2009; 15(19): 6177-84) showed that PBR expression is increased in prostatic intraepithelial neoplasia, primary prostate cancer and metastases as compared with normal prostate tissue and benign prostatic hyperplasia. A correlation was also seen with malignant disease progression with PBR levels observed to be increased with increasing Gleason score. Furthermore, prostate cancer metastases demonstrated the highest level of PBR expression among all tissues examined.

A link between PBR expression and fibrosarcoma tumours has also been reported (Yamasaki et al J Radiat Res 2010; 51: 57-65 and Nucl Med Biol 2009; 36(7): 801-9).

A number of in vivo imaging agents that target PBR are known in the art. [$^{11}$C]PK11195 has been considered the gold standard PET ligand for PBR and has been utilised in many clinical and pre-clinical studies. However, [$^{11}$C]PK11195 suffers from high and variable plasma protein binding and high lipophilicity leading to relatively low and variable brain uptake and relatively high levels of non-specific binding which can lead to inconsistent imaging results (Lockhart et al Nucl Med Biol 2003; 30(2): 199-206).

$^{11}$C and $^{18}$F derivatives of the DPA, DAA and other series have recently been investigated in pre-clinical and clinical settings against [$^{11}$C]PK11195 and claims have been made that these compounds have higher specific uptake. A selection of these imaging agents is illustrated below:

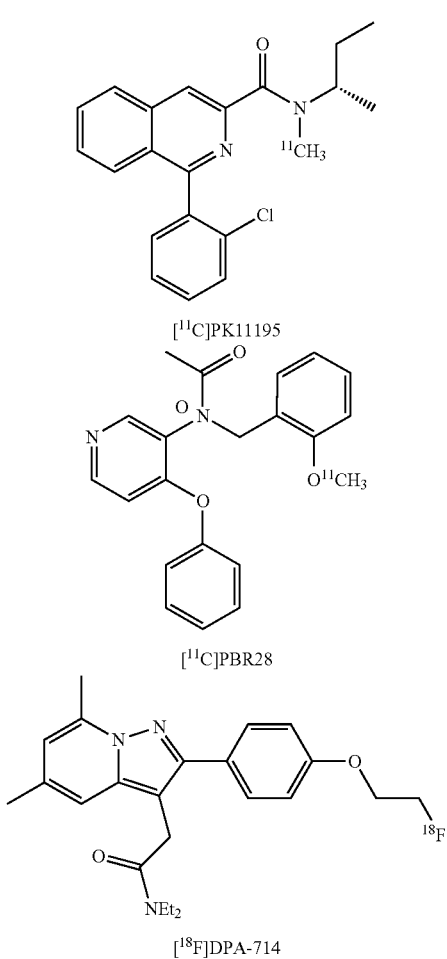

[11C]PK11195

[11C]PBR28

[18F]DPA-714

Chaveau et al (J Nuc Med 2009; 50(3): 468-476) report 18F-DPA-714 as an attractive alternative to 11C-PK11195 because of its increased bioavailability. An 11C labelled analogue of DAA1106, developed by the NIMH (named PBR28) has been assessed in humans for imaging inflammatory conditions including multiple sclerosis (MS) and atherosclerosis (Fujita et al Neuroimage 2008; 40(1): 43-52).

In the co-pending patent application WO 2010/109007 a series of radiolabelled tricyclic indole imaging agents is described that has improved properties over all of the above described in vivo imaging agents. These tricyclic indole in vivo imaging agents are described as useful in the diagnosis of inflammatory conditions wherein the PBR is abnormally expressed, and in particular neuroinflammatory conditions.

There is a need for improved methods useful in the diagnosis and monitoring of cancer.

SUMMARY OF THE INVENTION

The present invention provides a method useful in the diagnosis and monitoring of cancer wherein there is an abnormal expression of PBR. The method of the invention is particularly useful in evaluating the severity of the cancer, e.g. PBR expression correlates with cell proliferation rates, metastatic potential, tumour aggressiveness, malignancy progression. The method of the invention can therefore be applied in determining likely disease progression and associated prognosis. Furthermore, the method of the invention can find use in determining the likely success of certain therapeutic approaches, or in the evaluation of the efficacy of certain proposed new treatments.

BRIEF DESCRIPTION OF THE FIGURES

FIGS. 13-18 illustrate the biodistribution profile in the brain imaging agents 5-8, 10 and 11, respectively.

DETAILED DESCRIPTION OF THE INVENTION

Figure 1:
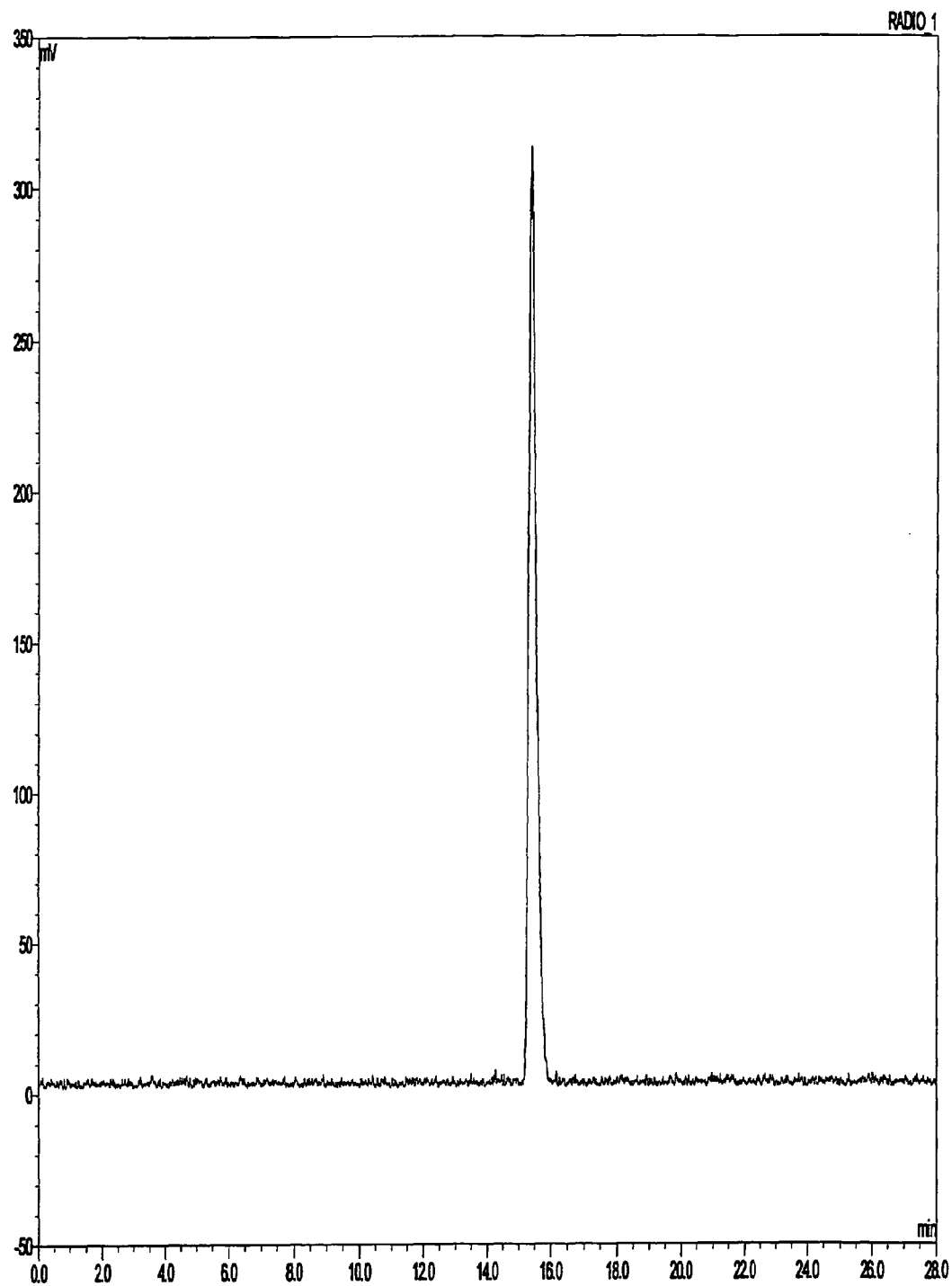
FIG. 1 shows co-elution of imaging agent 5 (prepared according to Example 1) and non-radioactive imaging agent 5 (prepared according to Example 2).

In one aspect, the present invention provides a method for the identification and/or monitoring of cancer in a subject wherein said cancer is characterised by abnormal expression of peripheral benzodiazepine receptors (PBR), wherein said method comprises the following steps:

(a) administering to said subject an in vivo imaging agent of Formula I:

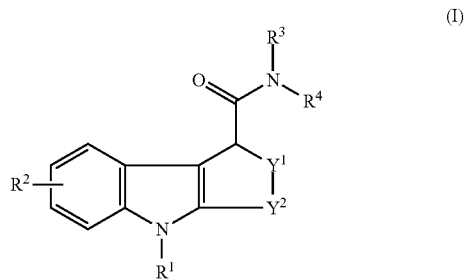

(I)

wherein:
R¹ is $C_{1-3}$ alkyl or $C_{1-3}$ fluoroalkyl;
R² is hydrogen, hydroxy, halo, cyano, $C_{1-3}$ alkyl, $C_{1-3}$ alkoxy, $C_{1-3}$ fluoroalkyl, or $C_{1-3}$ fluoroalkoxy;

$R^3$ and $R^4$ are independently $C_{1-3}$ alkyl, $C_{7-10}$ aralkyl, or $R^3$ and $R^4$, together with the nitrogen to which they are attached, form a nitrogen-containing $C_{4-6}$ aliphatic ring optionally comprising 1 further heteroatom selected from nitrogen, oxygen and sulfur;

$Y^1$ is O, S, SO, $SO_2$ or $CH_2$; and, $Y^2$ is $CH_2$, $CH_2$—$CH_2$, $CH(CH_3)$—$CH_2$ or $CH_2$—$CH_2$—$CH_2$;

and wherein said in vivo imaging agent of Formula I comprises an atom which is a radioisotope suitable for in vivo imaging;

(b) allowing said administered in vivo imaging agent of step (a) to bind to PBR expressed in said subject;

(c) detecting signals emitted by the radioisotope comprised in said bound in vivo imaging agent of step (b) using a suitable in vivo imaging procedure;

(d) generating an image representative of the distribution and/or extent of said signals detected in step (c);

(e) determining the distribution and/or extent of PBR expression in said subject wherein said expression is directly correlated with the distribution and/or extent of said signals as represented in said image generated in step (d); and, (f) using the distribution and extent of PBR expression as determined in step (e) in the identification and/or monitoring of said cancer.

The term "identification" is used to encompass both the clinical and pre-clinical settings. In the clinical setting where the subject is a patient, the term refers to a medical diagnosis, i.e. determining on the basis of information gathered in selected tests whether the patient is suffering from a particular disease or condition, and/or determining the nature of that disease or condition. Such a determination can be useful in the selection of the most appropriate method of treatment, or in reaching a prognosis. The term "prognosis" is taken to mean the likely outcome of the disease.

The term "monitoring" is taken herein to refer to the evaluation over time of the course of a disease or condition in a subject, particularly in the context of evaluating the efficacy of a treatment regimen.

The "subject" of the invention can be any human or animal subject. Preferably the subject of the invention is a mammal. Most preferably, said subject is an intact mammalian body in vivo, for example humans and mammals typically used in pre-clinical trials including naïve animals and animal models of cancer. In an especially preferred embodiment, the subject of the invention is a human. Preferably, the subject of the invention also is known or suspected to suffer from cancer, wherein the term "cancer" is defined as that class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Specifically, in the context of the present invention the pathophysiology of said cancer comprises abnormal expression of PBR. Non-limiting examples of such cancers are: glioma, astrocytoma, prostate cancer, breast cancer, ovarian cancer, hepatocarcinoma, fibrosarcoma, oral cancer and colorectal carcinoma.

The step of "administering" the in vivo imaging agent is preferably carried out parenterally, and most preferably intravenously. The intravenous route represents the most efficient way to deliver the in vivo imaging agent throughout the body of the subject into contact with PBR expressed in said subject. Intravenous administration does not represent a substantial physical intervention or a substantial health risk.

The in vivo imaging agent of the invention is preferably administered as a "radiopharmaceutical composition" comprising said in vivo imaging agent together with a pharmacologically-acceptable carrier.

The "pharmacologically-acceptable carrier" is a fluid, especially a liquid, in which the in vivo imaging agent is suspended or dissolved, such that the composition is physiologically tolerable, i.e. can be administered to the mammalian body without toxicity or undue discomfort. The pharmacologically-acceptable carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with pharmacologically-acceptable counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The pharmacologically-acceptable carrier may also comprise pharmacologically-acceptable organic solvents such as ethanol. Such organic solvents are useful to solubilise more lipophilic compounds or formulations. Preferably the pharmacologically-acceptable carrier is pyrogen-free water for injection, isotonic saline or an aqueous ethanol solution. The pH of the pharmacologically-acceptable carrier for intravenous injection is suitably in the range 4.0 to 10.5.

The radiopharmaceutical composition is most preferably an aqueous solution. Such a composition may optionally contain further ingredients such as buffers; pharmacologically acceptable solubilisers (e.g. cyclodextrins or surfactants such as Pluronic, Tween or phospholipids); pharmacologically acceptable stabilisers or antioxidants (such as ascorbic acid, gentisic acid or para-aminobenzoic acid).

The term "in vivo imaging agent" in the context of the present invention refers to a radiolabelled compound suitable for in vivo imaging. The term "in vivo imaging" as used herein refers to those techniques that noninvasively produce images of all or part of the internal aspect of a subject. Examples of in vivo imaging techniques suitable in the context of the present invention are single-photon emission tomography (SPECT) and positron emission tomography (PET), both of which are well-known techniques in the field of in vivo imaging (the reader is referred for example to "Emission Tomography: the Fundamentals of PET and SPECT"; 2004 Academic Press: Wernick and Aarsvold, Eds.).

Unless otherwise specified, the term "alkyl" alone or in combination, means a straight-chain or branched-chain alkyl radical preferably containing, unless otherwise specified, 1 to 3 carbon atoms. Examples of such radicals include methyl, ethyl, and propyl.

The term "fluoroalkyl" represents a haloalkyl group as defined below wherein the halogen is fluorine.

The term "hydroxy" refers to the group —OH.

The term "halogen" or "halo-" means a substituent selected from fluorine, chlorine, bromine or iodine. "Haloalkyl" and "haloalkoxy" are alkyl and alkoxy groups, respectively, as defined above substituted with one or more halogens. Suitably in the case of haloalkyl and haloalkoxy substituents, the halogen replaces a hydrogen at the terminal end of the radical, i.e. -alkylene-halogen or -alkoxylene-halogen. The term "alkylene" refers to the bivalent group —$(CH_2)_n$— wherein n is preferably 1-3, and the term "alkoxylene" refers to an alkylene group comprising an ether linkage, wherein an ether linkage is as defined above.

The term "cyano" refers to the group —CN.

Unless otherwise specified, the term "alkoxy" means an alkyl radical as defined above comprising an ether linkage, and the term "ether linkage" refers to the group —C—O—C—. Examples of suitable alkyl ether radicals include, methoxy, ethoxy, and propoxy.

The term "fluoroalkoxy" represents a haloalkoxy group as defined above wherein the halogen is fluorine.

The term "aralkyl" refers to the group -alkylene-phenyl wherein alkylene is as defined above.

A "nitrogen-containing $C_{4-6}$ aliphatic ring" is a saturated $C_{4-6}$ alkyl ring comprising a nitrogen heteroatom. Examples include pyrrolidinyl, piperidinyl and morpholinyl rings.

In the context of Formula I, the term "comprises an atom which is a radioisotope suitable for in vivo imaging" means that the isotopic form of one or more (preferably one) of the atoms defined herein for said formula is a radioisotope suitable for in vivo imaging. In order to be suitable for in vivo imaging, the radioisotope is detectable externally following administration to said subject, e.g. using an in vivo imaging technique such as SPECT or PET.

The step of "allowing" said administered in vivo imaging agent of step (a) to bind to PBR expressed in said subject follows the administering step and precedes the detecting step. For example, when the subject is an intact mammal, the in vivo imaging agent will dynamically move through the mammal's body, coming into contact with various tissues therein. Once the in vivo imaging agent comes into contact with PBR, a specific interaction takes place such that clearance of the in vivo imaging agent from tissue with PBR takes longer than from tissue without, or with less PBR. A certain point in time will be reached when detection of in vivo imaging agent specifically bound to PBR is enabled as a result of the ratio between in vivo imaging agent bound to tissue with PBR versus that bound in tissue without, or with less PBR. When a tissue is observed to express higher levels of PBR this can be an indication that this tissue is cancer tissue. Cancer tissue is comprised of malignant and non-malignant cells (i.e. endothelial cells, immune cells, fibroblasts) and PBR expression may be associated with any of these cell types. As noted by Zheng et al (Mol Pharmaceutics 2011; 8: 823-2) a significant portion of tumour stromal PBR expression in breast cancer tumours colocalised with F4/80 positive macrophage cells.

The "detecting" step of the method of the invention involves detection of signals emitted by the radioisotope of said in vivo imaging agent by means of a detector sensitive to said signals. This detecting step can also be understood as the acquisition of signal data. Single-photon emission tomography (SPECT) and positron-emission tomography (PET) are the most suitable in vivo imaging procedures for use in the method of the invention.

The "generating" step of the method of the invention is carried out by a computer which applies a reconstruction algorithm to the acquired signal data to yield a dataset. This dataset is then manipulated to generate images showing the location and/or amount of signals emitted by said radioisotope. The signals emitted therefore directly correlate with the expression of PBR such that the "determining" step can then be made by evaluating the generated image.

The step of "using" the information determined in step (e) in the identification and/or monitoring of said cancer can be understood to encompass identification of the presence of cancer in said subject, preferably as an aid to making a diagnosis, in selecting an appropriate treatment or in the determination of a patient's prognosis. In the context of identifying the presence of cancer, the information obtained in step (e) is compared with data obtained using the same in vivo imaging method carried out on a cohort of normal subjects, i.e. subjects known not to be suffering from cancer. In this way any significant deviation from the normal value for PBR expression can be determined, and this deviation can be attributed to a particular clinical picture. For monitoring said cancer, the information obtained in step (e) is compared with data obtained at an earlier point in time using the same in vivo imaging method carried out on the same subject. Differences between the information obtained at the various time points can indicate progression or regression of the cancer. The using step also encompasses monitoring as a means to evaluate the success of a treatment, or in the determination of the potential efficacy of a test compound as a new treatment. It is envisaged that the method of the invention can also be applied in a pre-clinical setting in the testing and optimisation of treatments under development.

A preferred in vivo imaging agent of Formula I is suitable for imaging using single photon emission computed tomography (SPECT) or positron emission tomography (PET). For SPECT, said in vivo imaging agent suitably comprises a gamma-emitting radioactive halogen. Examples of gamma-emitting radioactive halogens suitable for use in the present invention are $^{123}I$, $^{131}I$ and $^{77}Br$. A preferred gamma-emitting radioactive halogen is $^{123}I$. Where the radioisotope of the in vivo imaging agent is $^{123}I$ it is preferred that $R^2$ is $^{123}I$. For PET, said in vivo imaging agent suitably comprises a positron-emitting radioactive non-metal. Examples of positron-emitting radioactive non-metal suitable for use in the present invention are $^{11}C$, $^{18}F$ and $^{124}I$. Preferred positron-emitting radioactive non-metals are $^{11}C$ and $^{18}F$. In the case of $^{11}C$ it is preferred that $R^1$ is $^{11}C$ methyl. Where the radioisotope is $^{18}F$, it is preferred that $R^1$ is $C_{2-3}$ [$^{18}F$]fluoroalkyl, most preferably -ethylene-$^{18}F$.

PET is particularly preferred in the method of the invention due to its excellent sensitivity and resolution, so that even relatively small changes in a lesion can be observed overtime, which is particularly useful in monitoring disease progression over time e.g. in response to treatment. PET scanners routinely measure radioactivity concentrations in the picomolar range. Micro-PET scanners now approach a spatial resolution of about 1 mm, and clinical scanners about 4-5 mm.

Where a chiral centre or another form of an isomeric centre is present in an in vivo imaging agent according to the present invention, all forms of such isomer, including enantiomers and diastereoisomers, are encompassed by the present invention. In vivo imaging agents of the invention containing a chiral centre may be used as racemic mixture or as an enantiomerically-enriched mixture, or the racemic mixture may be separated using well-known techniques and an individual enantiomer maybe used alone.

in the method of the invention:

$R^1$ of Formula I is preferably methyl or $C_{2-3}$-fluoroalkyl;

$R^2$ of Formula I is preferably hydrogen, halo, $C_{1-3}$ alkoxy or $C_{1-3}$ fluoroalkoxy;

$R^3$ and $R^4$ of Formula I are preferably independently methyl, ethyl or benzyl; or, together with the nitrogen to which they are attached, form a nitrogen-containing $C_{5-6}$ aliphatic ring;

$Y^1$ of Formula I is preferably $CH_2$;

$Y^2$ of Formula I is preferably $CH_2$—$CH_2$.

In a preferred embodiment, said in vivo imaging agent of Formula I used in the method of the invention is of Formula Ia:

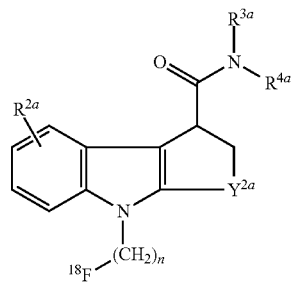
(Ia)

wherein:

$R^{2a}$ is hydrogen, halo or $C_{1-3}$ alkoxy;

$R^{3a}$ and $R^{4a}$ are independently methyl, ethyl or benzyl, or together with the nitrogen to which they are attached form a pyrrolidinyl, piperidinyl, azepanyl, or morpholinyl ring;

$Y^{2a}$ is as defined above for $Y^2$ of Formula I; and;

n is 1, 2 or 3.

Preferably for Formula Ia:

$R^{3a}$ and $R^{4a}$ are both ethyl, or $R^{3a}$ is methyl and $R^{4a}$ is benzyl, or together with the nitrogen to which they are attached form an azepanyl ring;

$R^{2a}$ is hydrogen, methoxy or fluoro;

$Y^{2a}$ is $CH_2$—$CH_2$ or $CH(CH_3)$—$CH_2$; and, n is 2.

Some non-limiting examples of in vivo imaging agents of Formula Ia suitable for use in the method of the invention are as follows:

1
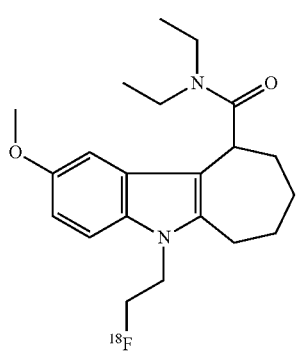

2
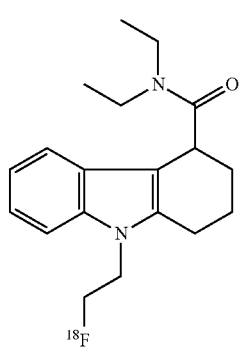

3
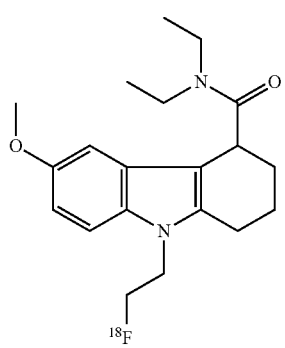

4
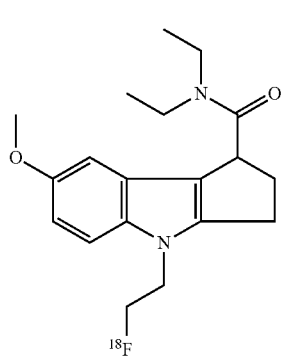

5
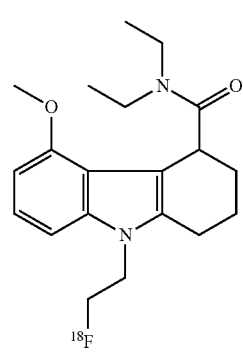

6
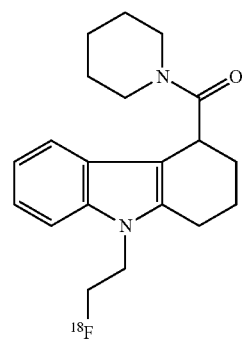

11

-continued

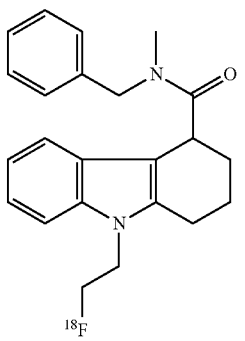

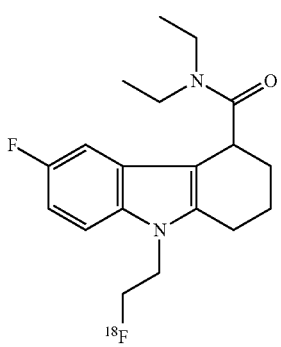

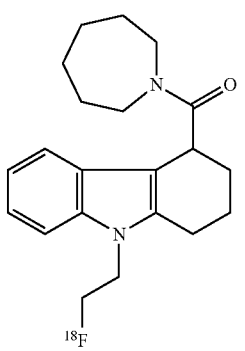

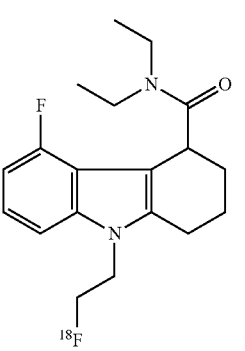

12

-continued

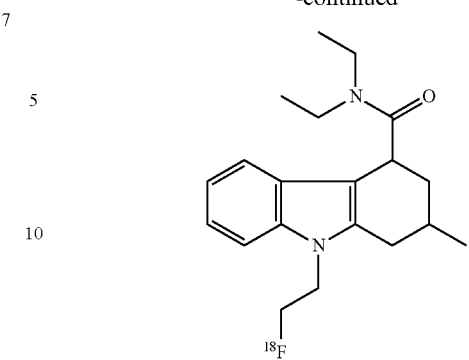

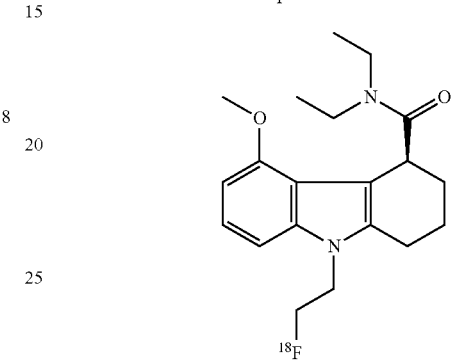

A particularly preferred in vivo imaging agent for use in the method of the invention is in vivo imaging agent 5 illustrated in the above table. The enantiomer of this imaging agent wherein the chiral centre has (S) configuration is most particularly preferred (illustrated as imaging agent 12 in the table above).

The above-described in vivo imaging agents are prepared by reaction of a precursor compound with suitable source of the radioisotope. A suitable such precursor compound is of Formula II:

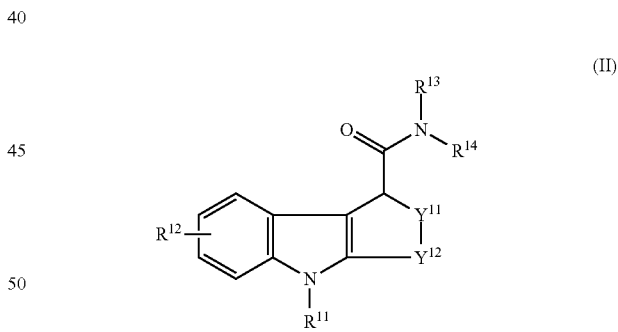

wherein one of $R^{11}$ and $R^{12}$ comprises a chemical group that reacts with a suitable source of the radioisotope as defined above, such that an in vivo imaging agent is formed upon reaction of said precursor compound with said suitable source of said radioisotope, and the other of $R^{11}$ and $R^{12}$ is as defined herein for $R^1$ and $R^2$, respectively, and optionally comprises a protecting group; and, $R^{13-14}$ and $Y^{11-12}$ are as defined herein for $R^{3-4}$ and $Y^{1-2}$, respectively, and optionally each further comprise a protecting group.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent of Formula I. Such precursor compounds are synthetic and can conveniently be obtained in good chemical purity.

By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Third Edition, John Wiley & Sons, 1999).

The term "a suitable source of a radioisotope" means the radioisotope in a chemical form that is reactive with a substituent of the precursor compound such that the radioisotope becomes covalently attached to the precursor compound. For each particular radioisotope presented in the following section, one or more suitable sources of the radioisotope are discussed. The person skilled in the art of in vivo imaging agents will be familiar with these and other sources of radioisotopes that are suitable for application in the present invention.

Scheme 1 below is a generic reaction scheme that shows how to obtain compounds that can themselves be used as suitable precursor compounds, or can be converted into precursor compounds with a small number of further Scheme 1

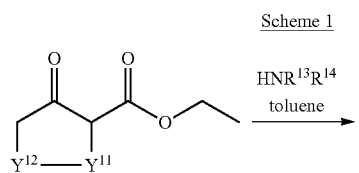

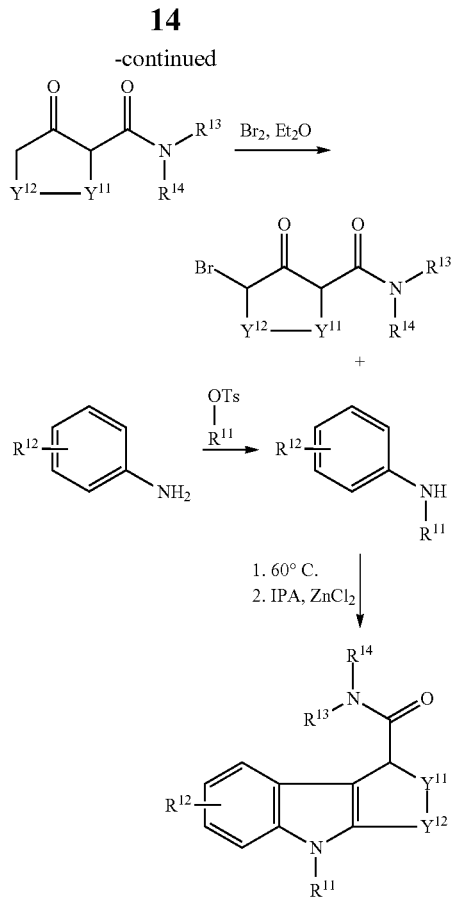

Alternatively, where $R^{12}$ of the precursor compound is at the top position on the ring, the general synthetic route illustrated in Scheme 1a below can be used:

Scheme 1a

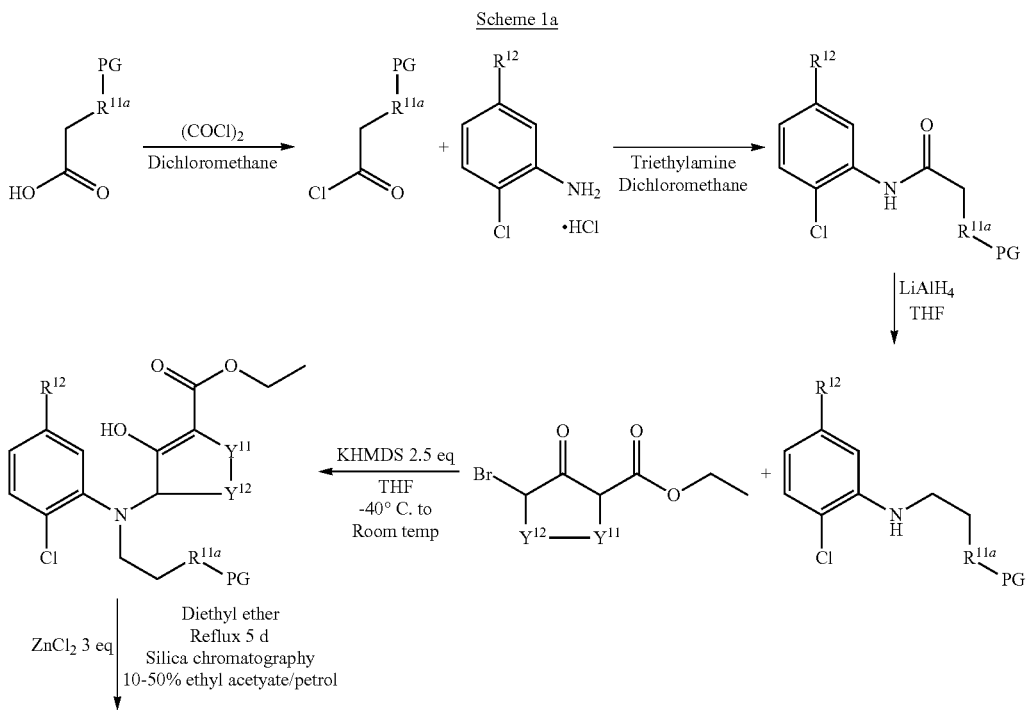

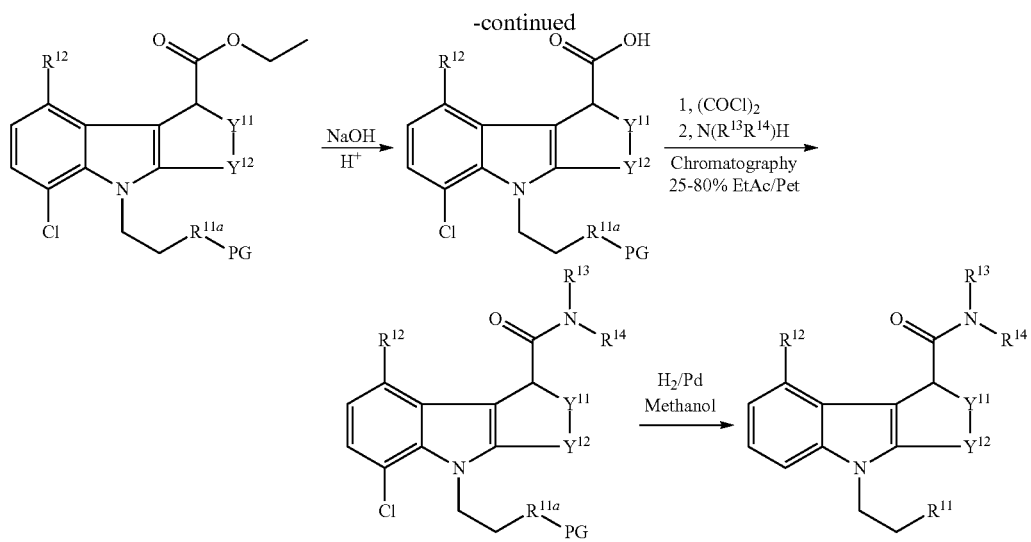

In Scheme 1a above, —$R^{11a}$-PG represents a protected $R^{11}$ group wherein $R^{11}$ is as suitably and preferably defined herein. Where $R^{11}$ is hydroxy —$R^{11a}$-PG may for example be —O-benzyl. $R^{12-14}$ and $Y^{11-12}$ are as suitably and preferably provided for Formula II above, with the proviso that $R^{12}$ is not chloro. In this synthetic route, the chlorine at the bottom position on the ring forces the cyclisation to take place in just one way such that only one isomer is produced. A similar method is disclosed in WO 2003/014082 but wherein the solvent system used for the cyclisation step is diethyl ether in place of toluene. The product of the cyclisation step dissolves in diethyl ether whereas the uncyclised starting compound does not. The uncyclised starting compound therefore remains with the $ZnCl_2$ at the bottom of the reaction vessel, and the cyclised product moves into the diethyl ether at the top of the reaction vessel.

When the radioisotope of the in vivo imaging agent is $^{18}F$, labelling with $^{18}F$ can be achieved by nucleophilic displacement of a leaving group from a precursor compound. Suitable leaving groups include Cl, Br, I, tosylate (OTs), mesylate (OMs) and triflate (OTf). Another strategy would be to have a suitable leaving group in place on an alkylamide group present on the precursor compound. In both cases, the precursor compound may be labeled in one step by reaction with a suitable source of [$^{18}F$]-fluoride ion ($^{18}F^-$), which is normally obtained as an aqueous solution from the nuclear reaction $^{18}O(p,n)^{18}F$ and is made reactive by the addition of a cationic counterion and the subsequent removal of water. $^{18}F$ can also be introduced by O-alkylation of hydroxy groups in the precursor compound with $^{18}F(CH_2)_3$-LG wherein LG represents a leaving group as defined above. Alternatively, the radiofluorine atom may attach via a direct covalent bond to an aromatic ring such as a benzene ring. For aryl systems, $^{18}F$-fluoride nucleophilic displacement from an aryl diazonium salt, aryl nitro compound or an aryl quaternary ammonium salt are suitable routes to aryl-$^{18}F$ derivatives.

Either Scheme 1 or Scheme 1a above can be continued to arrive at precursor compounds suitable for obtaining $^{18}F$ in vivo imaging agents for use in the method of the invention, e.g. as illustrated in Scheme 2 below:

Scheme 2

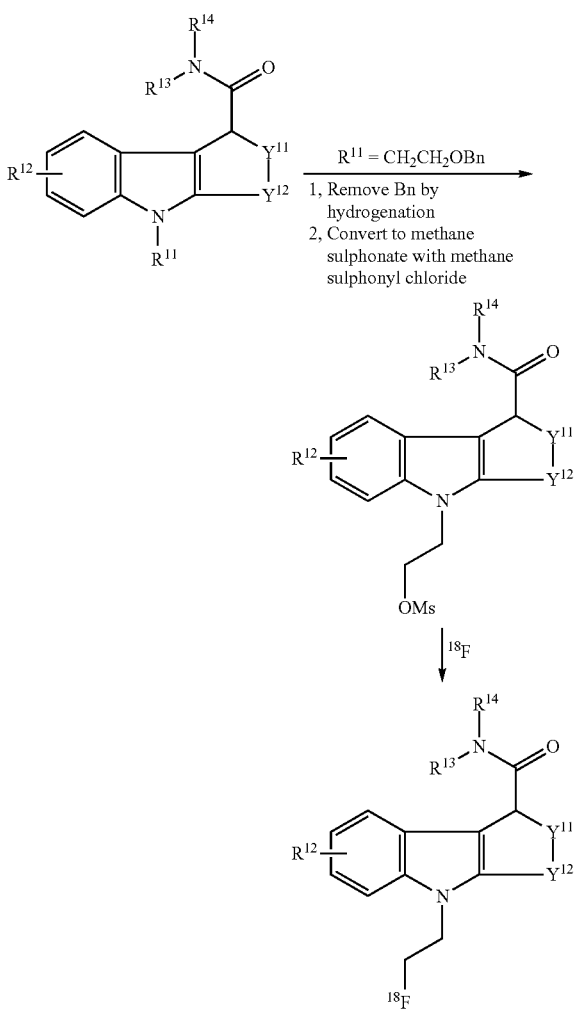

Starting compounds and intermediates are available commercially or are known from published scientific papers, e.g.

Napper et al J Med Chem 2005; 48: 8045-54; Davies et al J Med Chem 1998; 41: 451-467.

[11]C-labelled PET tracer compounds may be synthesised by reacting a precursor compound with $^{11}$C methyl iodide. As the half-life of $^{11}$C is only 20.4 minutes, it is important that the intermediate $^{11}$C methyl iodide has high specific activity and, consequently, that it is produced using a reaction process which is as rapid as possible. A thorough review of such $^{11}$C-labelling techniques may be found in Antoni et al "Aspects on the Synthesis of [11]C-Labelled Compounds" in Handbook of Radiopharmaceuticals, Ed. M. J. Welch and C. S. Redvanly (2003, John Wiley and Sons).

[11]C-labelled in vivo imaging agents for use in the method of the invention can be obtained by continuation of Scheme 1 above as illustrated in Scheme 3 below:

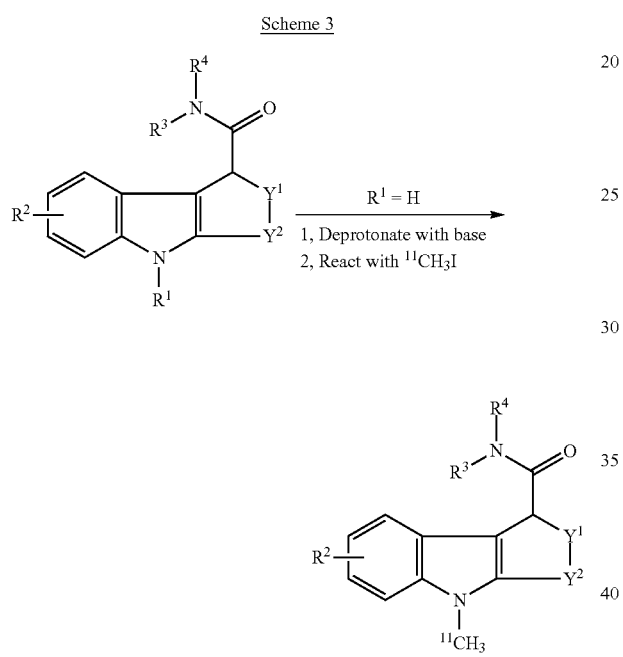

Where the imaging moiety is radioiodine, a precursor compound may comprise a derivative which either undergoes electrophilic iodination. Examples of this are organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates).

For electrophilic radioiodination, the precursor compound comprises: an activated organometallic precursor compound (e.g. trialkyltin, trialkylsilyl or organoboron compound). Precursor compounds and methods of introducing radioiodine into organic molecules are described by Bolton (J. Lab. Comp. Radiopharm. 2002; 45: 485-528). Suitable boronate ester organoboron compounds and their preparation are described by Kabalaka et al (Nucl. Med. Biol., 2002; 29: 841-843 and 2003; 30: 369-373). Suitable organotrifluoroborates and their preparation are described by Kabalaka et al (Nucl. Med. Biol., 2004; 31: 935-938).

Radioiodine labelled in vivo imaging agents for use in the method of the invention can be obtained by continuation of Scheme 1 above as illustrated in Scheme 4 below:

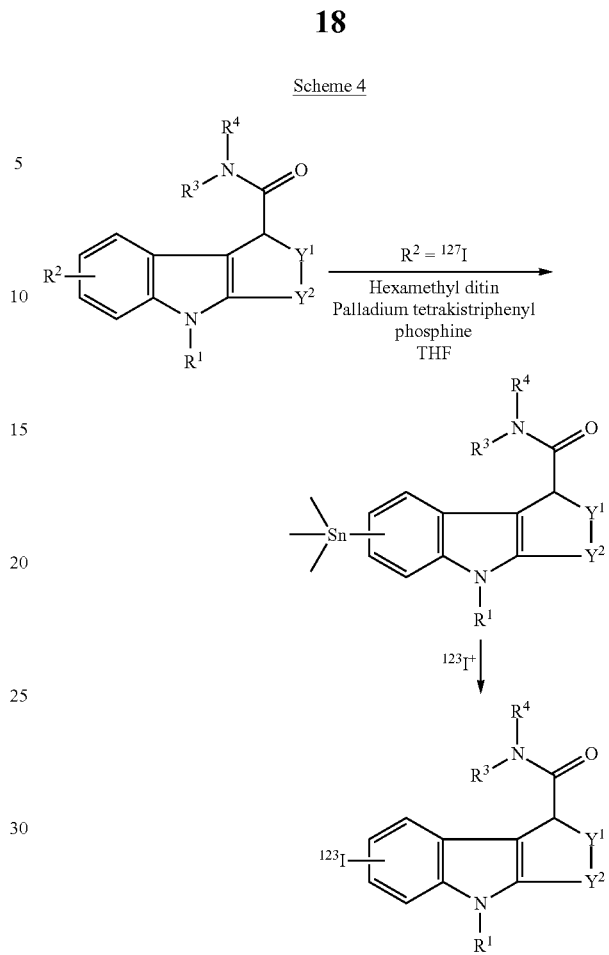

Radiobromination can be achieved by methods similar to those described above for radioiodination. Kabalka and Varma have reviewed various methods for the synthesis of radiohalogenated compounds, including radiobrominated compounds (Tetrahedron 1989; 45(21): 6601-21).

Precursor compounds for preparing in vivo imaging agents are ideally provided in sterile, apyrogenic form in order to be used for the preparation of a radiopharmaceutical composition comprising the in vivo imaging agent together with a pharmacologically-acceptable carrier suitable for mammalian administration. The precursor compound is also suitable for inclusion as a component in a kit or a cassette for the preparation of such a radiopharmaceutical composition.

The precursor compound may be bound to a solid phase and may be supplied covalently attached to a solid support matrix. In this way, the desired product forms in solution, whereas starting materials and impurities remain bound to the solid phase. As an example of such a system, precursor compounds for solid phase electrophilic fluorination with $^{18}$F-fluoride are described in WO 03/002489, and precursor compounds for solid phase nucleophilic fluorination with $^{18}$F-fluoride are described in WO 03/002157. Alternatively the precursor compound may be provided in solution in a kit or in a cassette suitable for use with an automated synthesis apparatus.

In a kit, the precursor compound can be presented in a sealed container which permits maintenance of sterile integrity and/or radioactive safety, plus optionally an inert headspace gas (e.g. nitrogen or argon), whilst permitting addition and withdrawal of solutions by syringe. An example of a sealed container is a septum-sealed vial, wherein the gas-tight closure is crimped on with an overseal (typically of aluminium). Such sealed containers have the advantage that the closure can withstand vacuum if desired e.g. to change the headspace gas or degas solutions. The precursor compound for use in the kit may be employed under aseptic manufacture conditions to give the desired sterile, non-pyrogenic material. The precursor compound may alternatively be employed under non-sterile conditions, followed by terminal sterilisation using e.g. gamma-irradiation, autoclaving, dry heat or chemical treatment (e.g. with ethylene oxide). Typically, all components of the kit are disposable to minimise the possibilities of contamination between runs and to ensure sterility and quality assurance.

Certain in vivo imaging agents, and in particular those labelled with $^{18}$F are now often conveniently prepared on an automated radiosynthesis apparatus. There are several commercially-available examples of such apparatus, including Tracerlab™ and Fastlab™ (GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. A typical such cassette comprises:

(i) a vessel containing a precursor compound as described herein; and
(ii) means for eluting the vessel with a suitable source of said radioisotope suitable for in vivo imaging as described herein.

The cassette may additionally comprise:
(iii) an ion-exchange cartridge for removal of excess radioisotope; and optionally,
(iv) where the precursor compound comprises one or more protecting groups, a cartridge for deprotection of the resultant radiolabelled product to form the desired in vivo imaging agent.

Where the in vivo imaging agent is administered as a radiopharmaceutical composition as described above, the method for preparation of said in vivo imaging agent may further comprise the steps required to obtain a radiopharmaceutical composition, e.g. removal of organic solvent, addition of a pharmacologically-acceptable carrier and any optional further ingredients. For parenteral administration, steps to ensure that the radiopharmaceutical composition is sterile and apyrogenic also need to be taken.

PBR expression can be correlated to various indices of cancer severity, as reported e.g. in the in vitro studies of Rechichi et al (Biochim Biophys Acta 2008; 1782: 118-25); Veenman et al (Biochem Pharmacol 2004; 68: 689-98); Mukhopadhyay et ai (Giycoconj J 2006; 23: 199-207); and Li et al (Biochem Pharmacol 2007; 73: 491-503), and in the in vivo studies of Maaser et al (Clin Cancer Res. 2002; 8: 3205-9); Vlodavsky & Soustiel (J Neurooncol 2007; 81: 1-7); Galiegue et al, (Clin Cancer Res 2004; 10: 2058-64), and Miettnen et al (Cancer Res 1995; 55: 2691-5). The method of the present invention can therefore be used in the evaluation of tumourgenicity, cell proliferation rates, metastatic potential of the cancer, tumour aggressiveness, malignancy progression, patient outcome and survival. The method of the invention can also be applied in the selection of the most appropriate treatment. Furthermore, the method of the invention can be used to determine whether treatment has been successful, as this will correlate with a reduction in PBR expression. In some instances [$^{18}$F]-fluorodeoxyglocose (FDG) is not ideal for assessing differentiation. The method of the invention therefore presents an improved method of in vivo imaging for certain cancers as compared with [$^{18}$F]-FDG imaging.

In an alternative aspect, the in vivo imaging method of the invention may be carried out repeatedly during the course of a treatment regimen for said subject, said regimen comprising administration of a drug to combat cancer wherein said cancer is as defined herein. For example, the in vivo imaging method of the invention can be carried out before, during and after said treatment in order to monitor its effectiveness over time. The suitable and preferred embodiments of the method of the invention as described herein also apply to this aspect of the invention. This aspect of the invention may also be applied in the evaluation of the efficacy of potential new treatments, e.g. in either pre-clinical or clinical studies.

In another aspect, the present invention provides an in vivo imaging agent, as suitably and preferably defined herein in respect of the method of the invention, for use in said method.

In a yet further aspect, the present invention provides for use of the in vivo imaging agent, as suitably and preferably defined herein in respect of the method of the invention, in the manufacture of a radiopharmaceutical composition as suitably and preferably defined herein for use in the method of the invention.

The invention is now illustrated by a series of non-limiting examples.

BRIEF DESCRIPTION OF THE EXAMPLES

Example 1 describes the synthesis of imaging agent 5.
Example 2 describes the synthesis of a non-radioactive analogue of imaging agent 5.
Example 3 describes the synthesis of imaging agent 6.
Example 4 describes the synthesis of a non-radioactive analogue of imaging agent 6.
Example 5 describes the synthesis of imaging agent 7.
Example 6 describes the synthesis of a non-radioactive analogue of imaging agent 7.
Example 7 describes the synthesis of imaging agent 8.
Example 8 describes the synthesis of a non-radioactive analogue of imaging agent 8.
Example 9 describes the synthesis of imaging agent 10.
Example 10 describes the synthesis of a non-radioactive analogue of imaging agent 10.
Example 11 describes the synthesis of imaging agent 11.
Example 12 describes the synthesis of a non-radioactive analogue of imaging agent 11.
Example 13 describes enantiomeric separation of precursor compound 5.
Example 14 describes enantiomeric separation of non-radioactive imaging agent 5.
Example 15 describes an in vitro potency assay that was used to test the affinity for PBR.
Example 16 describes a biodistribution method that was used to examine the performance of imaging agents of the invention in vivo.

List of Abbreviations Used in the Examples
aq aqueous
DCM dichloromethane
DMAP 4-Dimethylaminopyridine
DMF dimethylformamide
EDC 1-Ethyl-3-[3-dimethylaminopropyl]carbodiimide Hydrochloride
EOS end of synthesis
EtOAc ethyl acetate
IPA isopropyl alcohol
LC-MS liquid chromatography-mass spectrometry NMR nuclear magnetic resonance
OBn benzyloxy
OMs mesylate
OTs tosylate
RT room temperature
TLC thin layer chromatography
Tol toluene

EXAMPLES

Example 1

Synthesis of 9-(2-[$^{18}$F]Fluoro-ethyl)-5-methoxy-2,3,4,9-tetrahydro-1H-carbazole-4-carboxylic acid diethylamide (imaging agent 5)

Example 1(a)

Benzyloxy Acetyl Chloride (1)

To benzyloxyacetic acid (10.0 g, 60.0 mmol, 8.6 mL) in dichloromethane (50 mL) was added oxalyl chloride (9.1 g, 72.0 mmol, 6.0 mL) and DMF (30.0 mg, 0.4 mmol, 32.0 μL) and stirred at RT for 3 h. There was initially a rapid evolution of gas as the reaction proceeded but evolution ceased as the reaction was complete. The dichloromethane solution was concentrated in vacuo to give a gum. This gum was treated with more oxalyl chloride (4.5 g, 35.7 mmol, 3.0 mL), dichloromethane (50 mL), and one drop of DMF. There was a rapid evolution of gas and the reaction was stirred for a further 2 h. The reaction was then concentrated in vacuo to afford 11.0 g (quantitative) of Benzyloxy acetyl chloride (1) as a gum. The structure was confirmed by $^{13}$C NMR (75 MHz, CDCl$_3$) bc 73.6, 74.8, 128.1, 128.4, 128.6, 130.0, and 171.9.

Example 1(b)

2-Benzyloxy-N-(2-chloro-5-metnhoxy-phenyl)acetamide (2)

Benzyloxy acetyl chloride (1) (11.0 g, 60.0 mmol) and 2-chloro-5-methoxyaniline hydrochloride (11.7 g, 60.2 mmol) in dichloromethane (100 mL) at 0° C., was stirred and triethylamine (13.0 g 126.0 mmol, 18.0 mL) added slowly over 15 min. The stirred reaction was allowed to warm to RT over 18 h. There was a heavy precipitation of triethylamine hydrochloride. The dichloromethane solution was washed with 10% aqueous potassium carbonate (50 mL), dried over magnesium sulfate and concentrated in vacuo to afford 18.9 g (quantitative) of 2-Benzyloxy-N-(2-chloro-5-methoxy-phenyl)acetamide (2) as a gum. The structure was confirmed by $^{13}$C NMR (75 MHz, CDCl$_3$): δ$_C$ 55.6, 69.6, 73.6, 106.2, 111.1, 114.1, 127.7, 128.3, 128.6, 129.2, 134.6, 136.5, 158.9, and 167.7.

Example 1(c)

(2-Benzyloxy-ethyl)-(2-chloro-5-methoxyphenyl) amine (3)

2-Benzyloxy-N-(2-chloro-5-methoxy-phenyl)acetamide (2) (18.9 g, 62.0 mmol) in THF (100 mL) was stirred and lithium aluminum hydride (4.9 g, 130.0 mmol) was added slowly over 15 min. There was a rapid evolution of hydrogen gas as the first of the lithium aluminium hydride was added. The reaction was then heated to reflux for 4 h and allowed to stand at RT over the weekend. The reaction was then quenched by the dropwise addition of water (50 mL) to the stirred solution. There was a violent evolution of hydrogen causing the reaction mixture to reflux. The reaction was then concentrated in vacuum to a slurry. Water (200 mL) and ethyl acetate (200 mL) were added and the mixture vigorously shaken. The reaction was then filtered through celite to remove the precipitated aluminium hydroxide and the ethyl acetate solution was separated, dried over magnesium sulfate and concentrated in vacuo to afford 18.4 g (quantitative) of (2-Benzyloxy-ethyl)-(2-chloro-5-methoxyphenyl) amine (3) as a gum. The structure was confirmed by $^{13}$C NMR (75 MHz, CDCl$_3$) δ$_C$ 43.3, 55.3, 68.2, 73.0, 98.1, 101.8, 111.6, 127.6, 127.7, 128.4, 129.3, 137.9, 144.8, and 159.5.

Example 1(d)

3-Bromo-2-hydroxy-cyclohex-1-enecarboxylic acid ethyl ester (4)

Ethyl 2-oxocyclohexanecarboxylate (30 g, 176 mmol, 28 mL) was dissolved in diethyl ether (30 mL) and cooled to 0° C. under nitrogen. Bromine (28 g, 176 mmol, 9.0 mL) was added dropwise over 15 min and the reaction mixture was allowed to warm to RT over 90 min. The mixture was slowly poured into ice-cold saturated aqueous potassium carbonate (250 mL) and extracted with ethyl acetate (3×200 mL). The combined organic layers were dried over magnesium sulfate, filtered, concentrated in vacuo and dried on the vacuum line for 18 h to afford 41.4 g (94%) of 3-Bromo-2-hydroxy-1-enecarboxylic acid ethyl ester (4) as a yellow oil. The structure was confirmed by $^{13}$C NMR (75 MHz, CDCl$_3$): δ$_C$ 14.1, 17.7, 21.8, 32.0, 60.0, 60.8, 99.7, 166.3, and 172.8.

Example 1(e)

3[(2-Benzyloxy-ethyl)-(2-chloro-5-methoxyphenyl-amino]-2-hydroxy-cyclohex-1-ene carboxylic acid ethyl ester 5)

(2-Benzyloxy-ethyl)-(2-chloro-5-methoxyphenyl) amine (3) (10.0 g, 34.2 mmol) was stirred in dry THF (100 mL) at −40° C. under nitrogen and potassium bis(trimethylsilyl) amide (143.0 mL of a 0.5 M solution in toluene, 72.0 mmol) was added over 30 min. 3-bromo-2-hydroxycyclohex-1-enecarboxylic acid ethyl ester (4) (8.5 g, 34.2 mmol) in dry THF (10 mL) was then added and allowed to warm to RT over a period of 1.5 h. Acetic acid (10.0 g, 166 mmol, 10.0 mL) was added and concentrated in vacuo to remove the THF. Ethyl acetate (200 mL) and 10% aqueous potassium carbonate (100 mL) was added and the mixture vigorously shaken. The ethyl acetate solution was separated, dried over magnesium sulfate and concentrated in vacuo to afford 16.5 g (quantitative) of 3[(2-Benzyloxy-ethyl)-(2-chloro-5-methoxy-phenyl)-amino]-2-hydroxy-cyclohex-1-ene carboxylic acid ethyl ester (5) as a gum which was used crude in the next step. HPLC (Gemini 150×4.6 mm, 50-95% methanol/water over 20 min) of crude reaction mixture, 18.9 min (38%), 19.2 min (25%), 23.1 min (28%). One component of the reaction was isolated $^{13}$C NMR (75 MHz, CDCl$_3$) δ$_C$ 14.3, 20.6, 21.8, 26.4, 38.6, 43.0, 55.8, 60.5, 68.7, 73.3, 93.4, 106.3, 108.2, 119.3, 121.5, 127.5, 127.6, 128.3, 135.7, 137.0, 137.9, 155.7, and 175.0.

Example 1(f)

9-(2-Benzyloxy-ethyl)-8-chloro-5-methoxy-2,3,4,9,-tetrahydro-1H-carbazole-4-carboxylic acid ethyl ester (6)

Zinc chloride (7.1 g, 52.0 mmol) was added to 3-[(2-Benzyloxy-ethyl)-(2-chloro-5-methoxy-phenyl)-amino]-2-hydroxy-cyclohex-1-ene carboxylic acid ethyl ester (5) (8.0 g, 17.0 mmol) in dry diethyl ether (150 mL) under nitrogen and heated at reflux for 5.5 h. As the reaction was refluxed a thick brown dense oil formed in the reaction. The reaction was then cooled and the supernatant diethyl ether decanted off, ethyl acetate (100 mL) was added, washed with 2 N HCl (50 mL) and with 10% aqueous potassium carbonate (50 mL). The diethyl ether layer was separated, dried over magnesium sulfate and concentrated in vacuo to afford an oil (2.0 g). The crude material was purified by silica gel chromatography eluting with petrol (A):ethyl acetate (B) (10-40% (B), 340 g, 22 CV, 150 mL/min) to afford 1.8 g of 9-(2-Benzyloxy-ethyl)-8-chloro-5-methoxy-2,3,4,9,-tetrahydro-1H-carbazole-4-carboxylic acid ethyl ester (6). The thick dense brown layer was treated with ethyl acetate (100 mL) and 2 N HCl (50 mL). The ethyl acetate solution was separated, washed with 10% aqueous potassium carbonate (50 mL), dried over magnesium sulfate and concentrated in vacuo to give an oil (5.2 g). Diethyl ether (100 mL) and anhydrous zinc chloride (7.0 g) were added. The mixture was heated at reflux for a further 5 days. The ether layer was decanted off from the dark gum, was washed with 2 N HCl (50 mL), dried over magnesium sulfate and concentrated in vacuo to give a gum (2.8 g). This gum was purified by silica gel chromatography eluting with petrol (A):ethyl acetate (B) (5-35% (B), 340 g, 150 mL/min) to afford 2.1 g of 9-(2-Benzyloxy-ethyl)-8-chloro-5-methoxy-2,3,4,9,-tetrahydro-1H-carbazole-4-carboxylic acid ethyl ester (6). Total material obtained was 4.1 g (50%) of 9-(2-Benzyloxy-ethyl)-8-chloro-5-methoxy-2,3,4,9,-tetrahydro-1H-carbazole-4-carboxylic acid ethyl ester (6). The structure was confirmed by $^{13}$C NMR (75 MHz, CDCl$_3$): $\delta_C$ 14.4, 20.5, 22.3, 27.5, 40.2, 43.9, 55.0, 60.2, 70.7, 73.3, 100.2, 107.5, 108.4, 120.1, 122.8, 127.4, 127.5, 128.2, 132.0, 137.4, 138.1, 152.6, and 175.8.

Example 1(g)

9-(2-Benzyloxy-ethyl)-8-chloro-5-methoxy-2,3,4,9,-tetrahydro-1H-carbazole-4-carboxylic acid (7)

To 9-(2-Benzyloxy-ethyl)-8-chloro-5-methoxy-2,3,4,9,-tetrahydro-1H-carbazole-4-carboxylic acid ethyl ester (6) (2.0 g, 4.1 mmol) in ethanol (50 mL) was added sodium hydroxide (1.1 g, 27.1 mmol) and water (5 mL) and heated at 80° C. for 18 h. The ethanol was then removed by evaporation in vacuo and the residue partitioned between diethyl ether (50 mL) and water (50 mL). The diethyl ether layer was separated, dried over magnesium sulfate and concentrated in vacuo to give a gum (71.0 mg). The aqueous layer was acidified to pH 1 with 2N HCl (20 mL) and extracted with dichloromethane (2×100 mL). The dichloromethane layer was dried over magnesium sulfate and concentrated in vacuo to afford 1.6 g (87%) of 9-(2-Benzyloxy-ethyl)-8-chloro-5-methoxy-2,3,4,9,-tetrahydro-1H-carbazole-4-carboxylic acid (7) as a foam. The structure was confirmed by $^{13}$C NMR (75 MHz; CDCl$_3$): $\delta_C$ 20.2, 22.2, 27.1, 39.7, 44.0, 55.1, 70.7, 73.3, 100.6, 106.3, 108.9, 123.0, 127.4, 127.5, 128.3, 132.0, 138.0, and 152.0.

Example 1(h)

9-(2-Benzyloxy-ethyl)-8-chloro-5-methoxy-2,3,4,9,-tetrahydro-1H-carbazole-4-carbonyl chloride (8)

9-(2-Benzyloxy-ethyl)-8-chloro-5-methoxy-2,3,4,9,-tetrahydro-1H-carbazole-4-carboxylic acid (7) (1.5 g, 3.7 mmol) was dissolved in dichloromethane (50 mL) and oxalyl chloride (700 mg, 5.5 mmol, 470 µL) and DMF (1 drop) were added and the reaction stirred at 20° C. for 2 h. There was a moderate evolution of gas for about 30 min as the reaction proceeded. The reaction was then concentrated in vacuo to give 9-(2-Benzyloxy-ethyl)-8-chloro-5-methoxy-2,3,4,9,-tetrahydro-1H-carbazole-4-carbonyl chloride (8) as a gum which was used into the next step without purification. The structure was confirmed by $^{13}$C NMR (75 MHz; CDCl$_3$): $\delta_C$ 20.8, 22.1, 26.4, 44.2, 51.8, 55.1, 70.7, 73.3, 100.7, 106.0, 108.6, 119.5, 123.4, 127.3, 127.7, 128.3, 131.9, 138.0, 138.2, 152.0. and 176.3.

Example 1(i)

9-(2-Benxyloxy-ethyl)-8-chloro-5-methoxy-2,3,4,9-tetrahydro-1H-carbazole-4-carboxylic acid diethylamide (9)

9-(2-Benxyloxy-ethyl)-8-chloro-5-methoxy-2,3,4,9,-tetrahydro-1H-carbazole-4-carbonyl chloride (8) (1.6 g, 3.7 mmol) was then dissolved in dichloromethane (50 mL), cooled to 0° C., stirred and diethylamine (810 mg, 11.0 mmol, 1.1 mL) was added dropwise. The reaction was allowed to warm to room temperature over a period of 18 h. The reaction mixture was then washed with 10% aqueous potassium carbonate (50 mL), separated, dried over magnesium sulfate and concentrated in vacuo to a gum. The crude material was crystallized from diethyl ether to afford 1.2 g (71%) of 9-(2-Benxyloxy-ethyl)-8-chloro-5-methoxy-2,3,4,9-tetrahydro-1H-carbazole-4-carboxylic acid diethylamide (9) as a white crystalline solid. The structure was confirmed by $^{13}$C NMR (75 MHz; CDCl$_3$): $\delta_C$ 13.0, 14.5, 19.8, 22.2, 27.9, 36.4, 40.4, 41.9, 43.8, 55.0, 70.8, 73.3, 100.2, 108.5, 108.6, 119.9, 122.5, 127.4, 127.5, 128.3, 131.5, 137.8, 138.2, 152.4, and 174.5.

Example 1(j)

9-(2-Benzyloxy-ethyl)-5-methoxy-2,3,4,9-tetrahydro-1H-carbazole-4-carboxylic acid diethylamine (10)

9-(2-Benxyloxy-ethyl)-8-chloro-5-methoxy-2,3,4,9-tetrahydro-1H-carbazole-4-carboxylic acid diethylamide (9) (1.0 g, 2.1 mmol) in methanol (100 ml) was shaken with 10% palladium on charcoal (1.0 g), triethylamine (2.9 mg, 2.9 mmol, 4 µL) under an atmosphere of hydrogen gas for 18 h at 55° C. The reaction was then filtered through a pad of celite and the filtrate concentrated in vacuo to give a gum (908 mg). The gum was then taken up in dichloromethane (100 ml) and washed with 5% aqueous potassium carbonate solution (50 ml). The dichloromethane solution was then separated, dried over magnesium sulfate and concentrated in vacuo to afford a gum. The gum was then crystallised from diethyl ether (50 ml) and the crystals collected by filtration to afford 523 mg (57%) of 9-(2-Benzyloxy-ethyl)-5-methoxy-2,3,4,9-tetrahydro-1H-carbazole-4-carboxylic acid diethylamine (10). The structure was confirmed by $^{13}$C NMR (75 MHz; CDCl$_3$): $\delta_C$ 13.1, 14.6, 20.1, 22.0, 28.1, 36.4, 40.5, 42.0, 43.0, 54.7, 68.8, 73.3, 99.4, 102.4, 107.8, 116.4, 121.2, 127.6, 127.6, 128.3, 135.6, 137.8, 138.0 153.6, and 175.0.

Example 1(k)

9-(2-Hydroxyethyl)-5-methoxy-2,3,4,9-tetrahydro-1H-carbazole-4-carboxylic acid diethylamine (11)

9-(2-Benzyloxy-ethyl)-5-methoxy-2,3,4,9-tetrahydro-1H-carbazole-4-carboxylic acid diethylamine (10) (1.0 g, 2.1 mmol) in methanol (50 ml) was shaken with 10% palladium on charcoal (300 mg), and hydrogen gas excess for 18 h at 55° C. The reaction was then filtered through a pad of celite and the filtrate concentrated in vacuo to give 578 mg (100%) 9-(2-hydroxyethyl)-5-methoxy-2,3,4,9-tetrahydro-1H-carbazole-4-carboxylic acid diethylamine (11) as a foam. The structure was confirmed by $^{13}$C NMR (75 MHz; CDCl$_3$): $\delta_C$ 13.0, 14.4, 20.0, 22.0, 28.0, 36.4, 40.6, 42.0, 54.7, 60.6, 99.2, 102.6, 107.0, 116.7, 121.1, 136.1, 137.5, 138.0 153.5, and 175.7.

Example 1(l)

Methanesulphonic acid 2-(4-diethylcarbamyl-5-methoxy-1,2,3,4-tetrahydro-carbazol-9-yl)ethyl ester 9-(2-Hydroxyethyl)-5-methoxy-2,3,4,9-tetrahydro-1H-carbazole-4-carboxylic acid diethylamine (11) (478 mg, 1.4 mmol) in dichloromethane (30 ml) was cooled to 0° C. and methanesulfonyl chloride (477 mg, 4.2 mmol, 324 µL) and triethylamine (420 mg, 4.2 mmol, 578 µL) were added and allowed to warm to RT overnight. The reaction was washed with 5% aqueous potassium carbonate solution. The layers were separated. The combined organics were dried over magnesium sulfate and concentrated in vacuo to give a gum (696 mg). The crude material was purified by silica gel chromatography eluting with petrol (A):ethyl acetate (B) (75-100% B, 22 CV, 120 g, 85 mL/min) to afford Methanesulphonic acid 2-(4-diethylcarbamyl-5-methoxy-1,2,3,4-tetrahydro-carbazol-9-yl)ethyl ester as a gum that crystallised from diethyl ether to give 346 mg (59%) of a colourless solid. The structure was confirmed by $^{13}$C NMR (75 MHz; CDCl$_3$): $\delta_C$ 13.1, 14.5, 20.0, 21.9, 28.0, 36.3, 36.7, 40.3, 41.8, 41.9, 54.7, 68.1, 100.0, 102.0, 109.0, 116.4, 122.0 135.1, 137.3, 153.8, and 174.6.

Example 1(m)

9-(2-[$^{18}$F]Fluoro-ethyl)-5-methoxy-2,3,4,9-tetrahydro-1H-carbazole-4-carboxylic acid diethylamide (imaging agent 5)

[$^{18}$F]Fluoride was supplied from GE Healthcare on a GE PETrace cylcotron. Kryptofix 2.2.2 (2 mg, 5 µmol), potassium bicarbonate (0.1 mol dm$^{-3}$, 0.1 ml, 5 mg, 5 µmol) and acetonitrile (0.5 ml) was added to [$^{18}$F]F$^-$/H$_2$0 (ca. 400 MBq, 0.1-0.3 ml) in a COC reaction vessel. The mixture was dried by heating at 100° C. under a stream of nitrogen for 20-25 mins. After drying and without cooling, methanesulphonic acid 2-(4-diethylcarbamyl-5-methoxy-1,2,3,4-tetrahydro-carbazol-9-yl)ethyl ester (0.5-1 mg, 1.2-2.4 µmol) in acetonitrile (1 ml) was added to the COC reaction vessel and heated at 100° C. for 10 mins. After cooling, the reaction mixture was removed and the COC reaction vessel rinsed with water (1.5 ml) and added to the main crude reaction.

Following this, the crude product was applied to semi-preparative HPLC: HICHROM ACE 5 C18 column (100×10 mm i.d.), particle size 5 µm; mobile phase A: Water, mobile phase B: Methanol; flow gradient: 3 ml/min; 0-1 min 40% B; 1-20 mins 40-95% B; Wavelength 254 nm; $t_R$ imaging agent 5 16 mins. The imaging agent 5 HPLC purified-peak was diluted to a volume of 10 ml with water and adsorbed on a tC18 Sep-Pak (lite) cartridge. The cartridge was washed with water (2 ml), and eluted with anhydrous ethanol (0.5 ml) followed with Dulbecco's phosphate buffered saline (4.5 ml). Radiochemical yield 30±7% (n=4) non-decay corrected, time 90-120 mins, radiochemical purity ≥99%.

Analytical-HPLC: Phenomenex Luna C18 column (150× 4.6 mm i.d.), particle size 5 µm; mobile phase A: Water, mobile phase B: Methanol; flow gradient: 1 ml/min; 0-1 min 40% B; 1-20 mins 40-95% B; Wavelength 230 nm; $t_R$ imaging agent 5 16 mins. FIG. 1 shows co-elution of imaging agent 5 and non-radioactive imaging agent 5 (synthesis described in Example 2).

Example 2

Synthesis of 9-(2-Fluoro-ethyl)-5-methoxy-2,3,4,9-tetrahydro-1H-carbazole-4-carboxylic acid diethylamide (non-radioactive imaging agent 5)

Example 2(a)

Fluoroethyl Tosylate (12)

2-Fluoroethanol (640 mg, 10 mmol, 0.6 mL) was dissolved in pyridine (10 mL) under nitrogen. The solution was stirred at 0° C. and tosyl chloride (4.2 g, 21.8 mmol) added portionwise to the solution over a period of 30 min, keeping the temperature below 5° C. The reaction was stirred at 0° C. for 3 h. Ice was slowly added followed by water (20 mL). The reaction mixture was extracted into ethyl acetate and washed with water. Excess pyridine was removed by washing with 1 N HCl solution until the aqueous layer became acidic. Excess tosyl chloride was removed by washing with 1 M aqueous sodium carbonate. The organic layer was washed with brine, dried over magnesium sulfate and concentrated in vacuo to give 2.1 g (98%) of fluoroethyl tosylate (12) as a colourless oil. The structure was confirmed by $^{13}$C NMR (75 MHz, CDCl$_3$): $\delta_C$ 21.6 (C$\underline{C}$H$_3$), 68.5 (d, J$_{CF}$=173 Hz, O$\underline{C}$H$_2$CH$_2$F), 80.6 (d, J$_{CF}$=173 Hz, OCH$_2$$\underline{C}$H$_2$F), 128.0, 129.9, 132.6, and 145.1.

Example 2(b)

2-chloro-5-methoxy-phenyl) (2-fluoroethyl) amine (13)

2-Chloro-5-methoxyaniline hydrochloride (5.0 g, 26.0 mmol) was dissolved in DMF (50 mL) and sodium hydride (2.3 g, 60% in oil, 57.0 mmol) was added. The reaction was stirred for 30 minutes at RT under nitrogen. Fluoroethyl tosylate (12) (6.7 g, 31.0 mmol) in DMF (5 mL) was added dropwise and the reaction was stirred at RT for 2 h. The reaction was then heated at 100° C. for 18 h. The reaction was allowed to cool and the solvent was removed under reduced pressure. The residue was dissolved in ethyl acetate (100 mL) and washed with water (2×100 mL). The organics were collected, dried over magnesium sulfate and concentrated in vacuo to give a brown oil which was purified by silica gel chromatography eluting with petrol (A):ethyl acetate (B) (5-30% (B), 330 g, 18.1 CV, 120 mL/min) to afford 1.3 g (25%) of 2-chloro-5-methoxy-phenyl) (2-fluoroethyl)amine (13) as a yellow oil. The structure was confirmed by $^{13}$C NMR (75 MHz; CDCl$_3$): $\delta_C$ 43.8 (d, J$_{CF}$=23 Hz), 55.3, 82.0 (d, J$_{CF}$=165 Hz), 98.1, 102.2, 111.6, 129.5, 144.1, and 159.5.

Example 2(c)

3-[(2-Chloro-5-methoxy-phenyl)-(2-fluoroethyl) amino]-2-hydroxy-cyclohexyl-1-enecarboxylic acid ethyl ester (14)

A solution of 2-chloro-5-methoxy-phenyl) (2-fluoroethyl) amine (13) (6.1 g, 30.0 mmol) in THF (170 mL) was cooled to −40° C. Potassium bis(trimethylsilyl)amide (126.0 mL of a 0.5 M solution in toluene, 63.0 mmol) was added dropwise and the reaction stirred for 30 min at −40° C.) 3-Bromo-2-hydroxy-cyclohex-1-enecarboxylic acid ethyl ester (4; prepared according to Example 1(d)) (7.4 g, 30.0 mmol) in THF (30 mL) was added dropwise at −40° C. The cooling bath was removed and the reaction was stirred at RT for 4 h. The reaction was quenched with brine (300 mL) and extracted into ethyl acetate (2×400 mL), dried over magnesium sulfate and concentrated in vacuo to give 12.0 g (quantitative) of 3-[(2-Chloro-5-methoxy-phenyl)-(2-fluoroethyl)amino]-2-hydroxy-cyclohexyl-1-enecarboxylic acid ethyl ester (14) as a brown oil which was used crude in the next step. The structure as a mixture of isomers was confirmed by $^1$H NMR (300 MHz, CDCl$_3$): $\delta_H$ 1.08 (0.8H, t, J=9 Hz, CO$_2$CH$_2$CH$_3$), 1.22-1.33 (2.2H, m, CO$_2$CH$_2$CH$_3$), 1.40-2.60 (7H, m, 4-, 5-, and 6-CH$_2$, CHN), 3.20-4.50 (10H, m, NCH$_2$CH$_2$F, NCH$_2$CH$_2$F, OCH$_3$, CHCO$_2$CH$_2$CH$_3$), 6.50-6.70 (1H, m, CHC(OCH$_3$)CHCH), 6.95 (0.5H, dd, J=3 and 6 Hz, CHC(OCH$_3$)CHCH), 7.08 (0.5H, d, J=3 Hz, CHC(OCH$_3$)CHCH), and 7.20-7.30 (1H, m, CHC(OCH$_3$)CHCH).

Example 2(d)

8-chloro-9-(2-Fluoroethyl)-5-methoxy-2,3,4,9-tetrahydro-1H-carbazole-4-carboxylic acid ethyl ester (15)

Synthesis of 8-Chloro-9-(2-fluoro-ethyl)-5-methoxy-2,3,4,9-tetrahydro-1H-carbazole-4-carboxylic acid ethyl ester (15) was initially attempted using the conditions described in WO 2003/014082. A solution of 2-chloro-5-methoxy-phenyl) (2-fluoroethyl)amine (13; prepared according to Example 2(b)) (600 mg, 3.8 mmol) in dry THF (20 mL) was cooled in an ice bath and treated with potassium bis(trimethyl silyl)amide (16 mL of a 0.5 M solution in toluene, 8.0 mmol). After 30 minutes 3-Bromo-2-hydroxy-cyclohex-1-enecarboxylic acid ethyl ester (4; prepared according to Example 1(d)) (1.04 g, 4.2 mmol) in THF (4 mL) was added and the reaction was allowed to warm to RT over 2 hours.

The reaction was quenched with saturated ammonium chloride solution and extracted twice with ether. The extracts were washed with water, brine, dried and concentrated in vacuo. The crude material was purified by silica gel chromatography eluting with petrol (A) and ethyl acetate (B) (2.5-50% B, 50 g, 25 CV, 40 mL/min). The main spot was a mixture of three compounds. This mixture was refluxed in toluene (20 mL) with dry zinc chloride (1.7 g, 12.6 mmol) overnight. The reaction was concentrated in vacuo and the residue was partitioned between 1N HCL (25 mL) and ethyl acetate (25 mL) and then extracted once more with ethyl acetate. The organic layers were washed with water and brine, dried and concentrated in vacuo to afford a brown oil. $^1$H NMR indicated that it was a mixture of several compounds. TLC on silica in a range of solvents could not separate this mixture into separate spots. Comparison of the $^1$H NMR of the mixture with an authentic sample indicated that the mixture contained an estimated 25% of 8-Chloro-9-(2-fluoro-ethyl)-5-methoxy-2,3,4,9-tetrahydro-1H-carbazole-4-carboxylic acid ethyl ester (15).

A modified method was then carried out. 3-[(2-Chloro-5-methoxy-phenyl)-(2-fluoroethyl)amino]-2-hydroxy-cyclohexyl-1-enecarboxylic acid ethyl ester (14) (12.2 g, 30.0 mmol) was dissolved in diethyl ether (250 mL) and zinc chloride (16.4 g, 120.0 mmol) was added. The reaction was heated at reflux for 16 h. Ethyl acetate (500 mL) was added to dissolve everything and was washed with 2N HCl (200 mL), water (200 mL), 10% aqueous potassium carbonate (200 mL), dried over magnesium sulfate and concentrated in vacuo. The crude material was purified by silica gel chromatography eluting with petrol (A):ethyl acetate (B) (5-20% B, 12 CV, 10 g, 100 mL/min) to afford 5.3 g (50% over 2 steps) of 8-chloro-9-(2-Fluoroethyl)=5-methoxy-2,3,4,9-tetrahydro-1H-carbazole-4-carboxylic acid ethyl ester (15) as a yellow solid. The structure was confirmed by $^{13}$C NMR (75 MHz, CDCl$_3$): $\delta_C$ 14.4, 20.4, 22.2, 27.4, 40.1, 44.2(d, J$_{CF}$=23 Hz), 55.1, 60.2, 83.9 (d, J$_{CF}$=173 Hz), 100.6, 107.9, 108.2, 119.8, 123.1, 131.9, 137.2, 152.7, and 175.7.

Example 2(e)

9-(2-Fluoroethyl)-5-methoxy-2,3,4,9-tetrahydro-1H-carbazole-4-carboxylic acid ethyl ester 16)

8-chloro-9-(2-Fluoroethyl)-5-methoxy-2,3,4,9-tetrahydro-1H-carbazole-4-carboxylic acid ethyl ester (15) (5.3 g, 15.0 mmol) was dissolved in methanol (180 mL) and triethylamine (1.8 g, 18.0 mmol, 2.5 mL) and 10% Pd/C (2 g in methanol (20 mL)) were added. The mixture was placed on the Parr hydrogenator and shaken for 18 h under a hydrogen atmosphere. The reaction was filtered through a pad of celite, washed with methanol and the solvent was removed in vacuo. The residue was dissolved in ethyl acetate (300 mL) and washed with 10% aqueous potassium carbonate (200 mL), dried over magnesium sulfate and concentrated in vacuo to give 4.2 g (88%) of 9-(2-Fluoroethyl)-5-methoxy-2,3,4,9-tetrahydro-1H-carbazole-4-carboxylic acid ethyl ester (16) as a light brown solid. The structure was confirmed by $^{13}$C NMR (75 MHz, CDCl$_3$): $\delta_C$ 14.3, 20.6, 21.8, 27.6, 40.3, 43.3 (d, J$_{CF}$=23 Hz), 54.9, 60.1, 82.0 (d, J$_{CF}$=165 Hz), 99.8, 102.1, 107.3, 117.2, 121.8, 134.9, 137.6, 153.8, and 176.0.

HPLC (Gemini 150×4.6 mm, 50-95% methanol/water over 20 min) 13.6 min (94%).

Example 2(f)

9-(2-Fluoroethyl)-5-methoxy-2,3,4,9-tetrahydro-1H-carbazole-4-carboxylic acid (17)

8-chloro-9-(2-Fluoroethyl)-5-methoxy-2,3,4,9-tetrahydro-1H-carbazole-4-carboxylic acid ethyl ester (16) (380 mg, 1.2 mmol) was dissolved in ethanol (4 mL). A solution of sodium hydroxide (580 mg, 14.5 mmol) dissolved in 6 mL of water, was added. The reaction mixture was heated to reflux overnight. The solvent was removed in vacuo and the crude mixture diluted with water, acidified with 2 N HCl until acidic, and washed with dichloromethane. The organics were combined and dried over magnesium sulfate and concentrated in vacuo to give 347 mg (quantitative) of 9-(2-Fluoroethyl)-5-methoxy-2,3,4,9-tetrahydro-1H-carbazole-4-carboxylic acid (17) as an off white solid which was used crude into the next step. The structure was confirmed by $^{13}$C NMR (75 MHz; CDCl$_3$): $\delta_C$ 20.4, 21.9, 27.2, 39.9, 43.3 (d, J$_{CF}$=23 Hz), 55.1, 81.9 (d, J$_{CF}$=173 Hz), 100.3, 102.8, 106.2, 117.1, 122.2, 135.6, 137.8, 153.3, and 180.8.

Example 2(g)

9-(2-Fluoroethyl)-5-methoxy-2,3,4,9-tetrahydro-1H-carbazole-4-carbonyl chloride (18)

A solution of 9-(2-Fluoroethyl)-5-methoxy-2,3,4,9-tetrahydro-1H-carbazole-4-carboxylic acid (17) (347 mg, 1.2 mmol) in dry dichloromethane (2 mL) was stirred under nitrogen. Oxalyl chloride (453 mg, 3.6 mmol, 300 µL) was added followed by a drop of DMF. The reaction mixture was stirred at RT under nitrogen for 2 h then evaporated in vacuo to give 371 mg (quantitative) of 9-(2-fluoroethyl)-5-methoxy-2,3,4,9-tetrahydro-1H-carbazole-4-carbonyl chloride as a gum which was used in the next step without purification. The structure was confirmed by $^{13}$C NMR (75 MHz, CDCl$_3$): $\delta_C$ 20.2, 21.7, 26.4, 43.3 (d, $J_{CF}$=23 Hz), 54.9, 80.5, 83.1, 100.2, 102.2, 105.8, 116.7, 122.4, 135.5, 137.4, 153.5, and 176.6.

Example 2(h)

9-(2-Fluoroethyl)-5-methoxy-2,3,4,9-tetrahydro-1H-carbazole-4-carboxylic acid diethyl amide (non-radioactive imaging agent 5)

9-(2-fluoroethyl)-5-methoxy-2,3,4,9-tetrahydro-1H-carbazole-4-carbonyl chloride (18) (371 mg, 1.2 mmol) was dissolved in dichloromethane (2 mL) and cooled to 0° C. diethylamine (177 mg, 2.4 mmol, 250 µL) was then added and the reaction was stirred overnight at RT. The reaction was quenched with 10% aqueous potassium carbonate (2 mL). The dichloromethane layer was collected through a phase separator then concentrated in vacuo. The crude material was purified by silica gel chromatography eluting with petrol (A):ethyl acetate (B) (50-100% (B), 50 g, 35.2 CV, 40 mL/min) to afford a pale yellow solid. The solid was next triturated with a minimum amount of diethyl ether to afford 240 mg (58%) of 9-(2-Fluoroethyl)-5-methoxy-2,3,4,9-tetrahydro-1H-carbazole-4-carboxylic acid diethyl amide (non-radioactive imaging agent 5). The structure was confirmed by $^{13}$C NMR (75 MHz, CDCl$_3$): $\delta_C$ 13.0, 14.6, 19.9, 21.9, 28.0, 36.3, 40.5, 41.9, 43.1 (d, $J_{CF}$=23 Hz), 54.7, 82.0 (d, $J_{CF}$=173 Hz), 99.7, 102.1, 108.3, 117.0, 121.5, 135.3, 137.4, 153.3, and 174.8.

Example 3

Synthesis of [9-(2-[$^{18}$F]Fluoro-ethyl)-2,3,4,9-tetrahydro-1H-carbazol-4-yl]-piperidin-1-methanone (imaging agent 6)

Example 3(a)

2-(Piperidine-1-carbonyl)-cyclohexanone (19)

Ethyl 2-oxocyclohexane-carboxylate (5.3 g, 31 mmol, 5.0 mL) DMAP (1.05 g, 9.4 mmol) and piperidine (5.3 g, 63 mmol, 6.2 mL) in toluene (100 mL) were heated at reflux for 4 days. The reaction was allowed to cool and the reaction was concentrated in vacuo. The crude material was purified by silica gel chromatography eluting with petrol (A) and ethyl acetate (B) (20-80% (B), 100 g, 8 CV, 85 mL/min) to afford 6.26 g (96%) of 2-(piperidine-1-carbonyl)-cyclohexanone (19) as a white solid. The structure was confirmed by $^{13}$C NMR (75 MHz, CDCl$_3$) $\delta_C$ 23.5, 24.5, 25.5, 26.2, 27.1, 30.4, 41.9, 42.9, 46.8, 54.2, 167.6, 207.6.

Example 3(b)

2-Bromo-6-(piperidine-1-carbonyl)-cyclohexanone (20)

2-(piperidine-1-carbonyl)-cyclohexanone (19) (4.0 g, 19 mmol) was dissolved in diethyl ether (5 mL) and cooled to 0° C. under N$_2$. Bromine (5.9 g, 19 mmol, 1.0 mL) was added dropwise over 15 min and the reaction mixture was allowed to warm to room temperature over 90 min. The solid was collected by filtration to give 5.86 g (quantitative) of 2-bromo-6-(piperidine-1-carbonyl)-cyclohexanone (20) as a white solid which was used in the next step without purification. The structure was confirmed by $^{13}$C NMR (75 MHz, DMSO-d$_6$) $\delta_C$ 17.3, 24.2, 25.3, 25.8, 32.5, 44.0, 51.6, 108.3, 145.5, 167.8.

Example 3(c)

(2-Benzyloxy-ethyl)-phenyl-amine (21)

In a round bottom flask aniline (2.0 g, 21.5 mmol, 2.0 mL), 2,6-lutidine (2.30 g, 21.5 mmol) and benzyl 2-bromoethyl ether (4.6 g, 21.5 mmol, 3.4 mL) were combined in DMF (10 mL) and stirred at 100° C. overnight. The reaction was allowed to cool and then diluted with ethyl acetate (50 mL). This was washed with water (3×20 mL) and the organics were dried and concentrated in vacuo. The crude material was purified by silica gel chromatography eluting with petrol (A) and ethyl acetate (B) (0-50% B, 100 g, 19.5 CV, 85 mL/min) to afford 2.22 g (37%) of (2-benzyloxy-ethyl)-phenyl-amine (21) as a yellow oil. The structure was confirmed by $^{13}$C NMR (75 MHz, CDCl$_3$) $\delta_C$ 43.6, 68.6, 73.2, 113.1, 117.5, 127.5, 127.7, 128.4, 129.1, 138.2, 148.1.

Example 3(d)

[9-(2-Benzyloxy-ethyl)-2,3,4,9-tetrahydro-1H-carbazol-4-yl]-piperidin-1-methanone (22)

A mixture of 2-bromo-6-(piperidine-1-carbonyl)-cyclohexanone (20) (1.5 g, 5.2 mmol) and (2-benzyloxy-ethyl)-phenyl-amine (21) (3.2 g, 10.4 mmol) was stirred under N$_2$ at 50° C. for 3 h and the reaction turned brown. The resulting mixture was dissolved in propan-2-ol (5 mL) and dry zinc chloride (2.13 g, 15.6 mmol) was added. The mixture was heated to reflux under N$_2$ for 16 h and then concentrated in vacuo. The residue was dissolved in ethyl acetate (100 mL) and washed with 2 N HCl (30 mL), water (2×30 mL) and aqueous potassium carbonate solution (2×30 mL) then dried and concentrated in vacuo. The crude material was purified by SCX cartridge and then silica gel chromatography eluting with petrol (A) and ethyl acetate (B) (30-100% B, 12 g, 41 CV, 30 mL/min) to afford 600 mg (27%) of [9-(2-benzyloxy-ethyl)-2,3,4,9-tetrahydro-1H-carbazol-4-yl]-piperidin-1-yl-methanone (22) as an oil. The structure was confirmed by $^{13}$C NMR (75 MHz, CDCl$_3$) $\delta_C$ 21.5, 21.7, 24.5, 25.7, 26.3, 273, 37.7, 42.8, 43.1, 46.7, 60.2, 68.7, 73.1, 108.2, 108.7, 117.8, 118.9, 120.5, 126.4, 127.3, 127.4, 128.1, 136.2, 137.8, 172.9.

Example 3(e)

[9-(2-Hydroxy-ethyl)-2,3,4,9-tetrahydro-1H-carbazol-4-yl]-piperidin-1-yl-methanone (23)

To a solution of [9-(2-benzyloxy-ethyl)-2,3,4,9-tetrahydro-1H-carbazol-4-yl]-piperidin-1-yl-methanone (22) (600 mg, 1.4 mmol) in methanol (15 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo. The crude material was triturated to afford 332 mg (71%) of [9-(2-hydroxy-ethyl)-2,3,4,9-tetrahydro-1H-carbazol-4-yl]-piperidin-1-yl-methanone (23) as a white solid. The structure was confirmed by $^{13}$C NMR (75 MHz, CDCl$_3$): $\delta_C$ 21.2, 21.9, 24.7, 27.4, 36.4, 43.4, 45.0, 47.0, 60.9, 107.8, 109.0, 117.7, 119.0, 120.7, 126.6, 136.2, 137.2, 173.5

Example 3(f)

Methanesulfonic acid 2-[4-(piperidine-1-carbonyl)-1, 2,3,4-tetrahydro-carbazol-9-yl]-ethyl ester (precursor compound 6)

To a solution of [9-(2-hydroxy-ethyl)-2,3,4,9-tetrahydro-1H-carbazol-4-yl]-piperidin-1-yl-methanone (23) (260 mg, 0.8 mmol) in dichloromethane (15 mL) was added pyridine (633 mg, 8.0 mmol, 0.65 mL). The reaction was cooled to 0° C. and methanesulfonyl chloride (458 mg, 4.0 mmol, 0.31 mL) was added. The reaction was allowed to warm to room temperature overnight. The mixture was washed with 2 N HCl (2×50 mL) and water (2×50 mL), dried and concentrated in vacuo. The crude material was triturated with diethyl ether to afford 263 mg (82%) of methanesulfonic acid 2-[4-(piperidine-1-carbonyl)-1,2,3,4-tetrahydro-carbazol-9-yl]-ethyl ester as a white solid. The structure was confirmed by $^{13}$C NMR (75 MHz, CDCl$_3$) $\delta_C$ 21.4, 21.8, 24.7, 25.9, 26.9, 27.4, 36.6, 36.8, 41.7, 43.3, 47.0, 67.9, 108.5, 109.5, 118.4, 119.7, 121.3, 126.9, 136.2, 172.7.

Example 3(g)

[9-(2-[$^{18}$F]Fluoro-ethyl)-2,3,4,9-tetrahydro-1H-carbazol-4-yl]-piperidin-1-yl-methanone (imaging agent 6)

Figure 2:
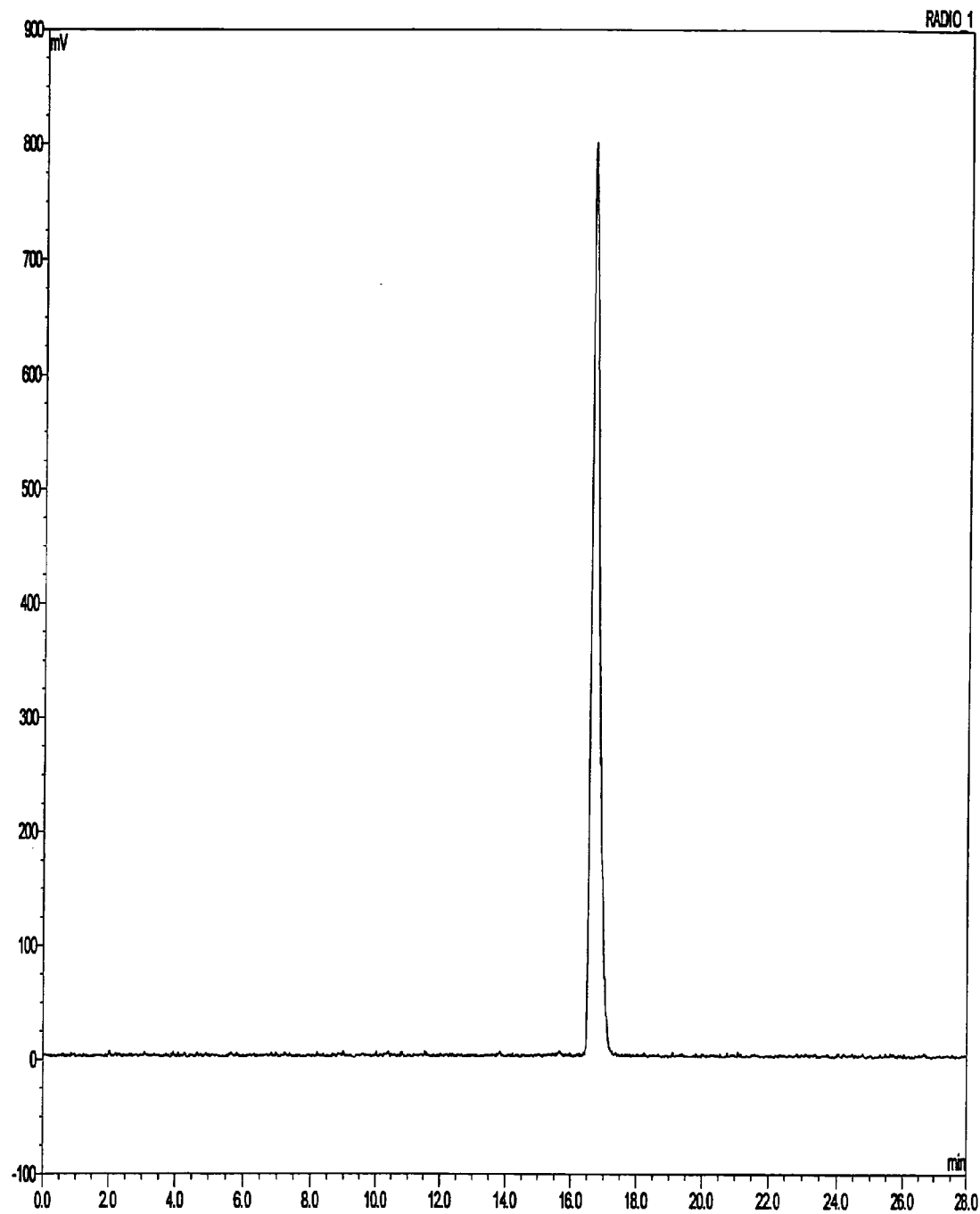
FIG. 2 shows co-elution of imaging agent 6 (prepared according to Example 3) and non-radioactive imaging agent 6 (prepared according to Example 4).

Labelling of methanesulfonic acid 2-[4-(piperidine-1-carbonyl)-1,2,3,4-tetrahydro-carbazol-9-yl]-ethyl ester with $^{18}$F was carried out as described in Example 1(f).
Semi-preparative HPLC: HICHROM ACE 5 C18 column (100×10 mm i.d.), particle size 5 µm; mobile phase A: Water, mobile phase B: Methanol; flow gradient: 3 ml/min; 0-1 min 50% B; 1-20 mins 50-95% B; Wavelength 254 nm; $t_R$ imaging agent 6, 17 mins.
Analytical-HPLC: Phenomenex Luna C18 column (150× 4.6 mm i.d.), particle size 5 µm; mobile phase A: Water, mobile phase B: Methanol; flow gradient: 1 ml/min; 0-1 min 50% B; 1-20 mins 50-95% B; Wavelength 230 nm; $t_R$ imaging agent 6 16 mins. Radiochemical yield 23±2% (n=3) non-decay corrected, time 90-120 mins, radiochemical purity ≥99%. FIG. 2 shows co-elution of imaging agent 6 and non-radioactive imaging agent 6 (prepared according to Example 4).

Example 4

Synthesis of [9-(2-Fluoro-ethyl)-2,3,4,9-tetrahydro-1H-carbazol-4-yl]-piperidin-1-yl-methanone (non-radioactive analogue of imaging agent 6)

Example 4(a)

(2-Fluoro-ethyl)-phenyl-amine (24)

In a round bottom flask aniline (0.5 g, 5.4 mmol), 2,6-lutidine (0.58 g, 5.4 mmol) and 2-fluoroethyl tosylate (12; prepared according to Example 2(a)) (1.17 g, 5.4 mmol) were combined in DMF (2.5 mL) and stirred at 100° C. overnight. The reaction was allowed to cool and then diluted with ethyl acetate (50 mL). This was washed with water (3×20 mL) and the organics were dried and concentrated in vacuo. The crude material was purified by silica gel chromatography eluting with petrol (A) and ethyl acetate (B) (100 g, 0-100% B, 18 CV, 85 mL/min) to give 435 mg (60%) of (2-fluoro-ethyl)-phenyl-amine (24) as a yellow oil. The structure was confirmed by $^1$H NMR (300 MHz, CDCl$_3$) $\delta_H$ 3.41 (1H, t, J=3 Hz, NCH$_2$CH$_2$F), 3.50 (1H, t, J=3 Hz, NCH$_2$CH$_2$F), 3.93 (1H, s, br), 4.54 (1H, t, J=3 Hz, NCH$_2$CH$_2$F), 4.71 (1H, t, J=3 Hz, NCH$_2$CH$_2$F), 6.65-6.82 (3H, m, 2×NCCH, NCCHCHCH), 7.14-7.28 (2H, m, 2×NCCHCHCH).

Example 4(b)

[9-(2-Fluoro-ethyl)-2,3,4,9-tetrahydro-1H-carbazol-4-yl]-piperidin-1-yl-methanone (non-radioactive imaging agent 6)

A mixture of 2-bromo-6-(piperidine-1-carbonyl)-cyclohexanone (20; prepared according to example 3(b)) (500 mg, 1.7 mmol) and (2-fluoro-ethyl)-phenyl-amine (24) (890 mg, 3.5 mmol) was stirred under N$_2$ at 50° C. for 3 h and the reaction turned brown. The resulting mixture was dissolved in propan-2-ol (2 mL) and dry zinc chloride (682 mg, 5 mmol) was added. The mixture was heated to reflux under N$_2$ for 16 h and then concentrated in vacuo. The residue was dissolved in ethyl acetate (50 mL) and washed with 2 N HCl (20 mL), water (2×20 mL) and aqueous potassium carbonate solution (2×20 mL) then dried and concentrated in vacuo. The crude material was triturated with diethyl ether to afford 151 mg (27%) of [9-(2-fluoro-ethyl)-2,3,4,9-tetrahydro-1H-carbazol-4-yl]-piperidin-1-yl-methanone (non-radioactive imaging agent 6) as a white solid. The structure was confirmed by $^{13}$C NMR (75 MHz, CDCl$_3$) $\delta_C$ 21.6, 21.8, 24.7, 26.5, 26.9, 27.4, 37.3, 43.1 (d, $J_{CF}$=45 Hz), 47.0, 82.1 (d, $J_{CF}$=173 Hz), 108.5, 108.9, 118.6, 119.4, 121.0, 126.8, 136.2, 172.7.

Example 5

Synthesis of 9-(2-[$^{18}$F]fluoro-ethyl-2,3,4,9-tetrahydro-1H-carbazole-4-carboxylic acid benzyl-methyl-amide (imaging agent 7)

Example 5(a)

9-(2-Benzyloxy-ethyl)-2,3,4,9-tetrahydro-1H-carbazole-4-carboxylic acid ethyl ester (25)

A mixture of (2-benzyloxy-ethyl)-phenyl-amine (21; prepared according to Example 3(c)) (8.0 g, 26 mmol) and 3-bromo-2-hydroxy-cyclohex-1-enecarboxylic acid ethyl ester (4; prepared according to Example 1(d)) (3.2 g, 13 mmol) was stirred under N$_2$ at 50° C. for 3 h and the reaction turned brown. The resulting mixture was dissolved in propan-2-ol (30 mL) and dry zinc chloride (10.6 g, 78 mmol) was added. The mixture was heated to reflux under N$_2$ for 16 h and then concentrated in vacuo. The residue was dissolved in ethyl acetate (300 mL) and washed with 2 N HCl (100 mL), water (2×100 mL) and aqueous potassium carbonate solution (2×100 mL) then dried and concentrated in vacuo. The crude material was purified by silica gel chromatography eluting with petrol (A) and ethyl acetate (B) (2.5-40% B, 17 CV, 330 g, 100 mL/min) to give 3.49 g (72%) of 9-(2-benzyloxy-ethyl)-2,3,4,9-tetrahydro-1H-carbazole-4-carboxylic acid ethyl ester (25) as an oil. The structure was confirmed by $^{13}$C NMR (75 MHz, CDCl$_3$) $\delta_C$ 14.2, 20.5, 21.8, 26.5, 38.6, 42.9, 60.4, 68.7, 73.2, 106.4, 108.8, 118.7, 120.7, 127.4, 127.5, 128.3, 136.2, 136.9, 137.8, 175.0.

Example 5(b)

9-(2-Benzyloxy-ethyl)-2,3,4,9-tetrahydro-1H-carbazole-4-carboxylic acid (26)

9-(2-Benzyloxy-ethyl)-2,3,4,9-tetrahydro-1H-carbazole-4-carboxylic acid ethyl ester (25) (35 g, 9.3 mmol) was dissolved in ethanol (9 mL) and then NaOH (1.56 g) in water (15 mL) was added. The reaction was heated at reflux for 2 h. The reaction was concentrated in vacuo and the residue diluted with water and washed with dichloromethane (2×150 mL). The aqueous layer was added drop wise to 2 N HCl (150 mL) and then extracted into dichloromethane (3×150 mL). The organics were dried and concentrated in vacuo to afford 2.48 g (92%) of 9-(2-benzyloxy-ethyl)-2,3,4,9-tetrahydro-1H-carbazole-4-carboxylic acid (26) as a yellow solid which was used in the next step without purification.

The structure was confirmed by $^{13}C$ NMR (75 MHz, $CDCl_3$) $\delta_C$ 20.4, 21.8, 26.4, 38.3, 42.9, 68.7, 73.3, 105.7, 108.8, 118.7, 119.3, 102.9, 127.4, 127.6, 128.3, 136.2, 137.1, 137.8, 108.9.

Example 5(c)

9-(2-benzyloxy-ethyl)-2,3,4,9-tetrahydro-1H-carbazole-4-carboxylic acid benzyl-methyl-amide (27)

9-(2-Benzyloxy-ethyl)-2,3,4,9-tetrahydro-1H-carbazole-4-carboxylic acid (26) (600 mg, 1.7 mmol) was dissolved in dry DCM (8 mL) under nitrogen and oxalyl chloride (393 mg, 3.1 mmol, 0.26 mL) was added. The reaction was stirred at room temperature for 3 h and there was vigorous evolution of gas. The reaction was concentrated in vacuo and then redissolved in dichloromethane (8 mL) and cooled to 0° C. and N-benzylmethylamine (412 mg, 3.4 mmol, 0.44 mL) was added. The reaction was warmed to room temperature overnight. The reaction was washed with 5% aqueous potassium carbonate solution, dried and concentrated in vacuo to afford a brown oil. The crude material was purified by silica gel chromatography eluting with petrol (A) and ethyl acetate (B) (30% B, 10 g) to afford 246 mg (64%) of 9-(2-benzyloxy-ethyl)-2,3,4,9-tetrahydro-1H-carbazole-4-carboxylic acid benzyl-methyl-amide (27) as a yellow oil. The structure was confirmed by $^1H$ NMR ($CDCl_3$) $\delta_H$ 1.60-2.30 (4H, m, CHC$\underline{H}_2C\underline{H}_2C\underline{H}_2$), 2.70-2.90 (2H, m, CHC$\underline{H}_2C\underline{H}_2$C$\underline{H}_2$), 3.10 (1.5H, s, N(C$\underline{H}_3$)CH$_2$Ph), 3.13 (1.5H, s, N(C$\underline{H}_3$)CH$_2$Ph), 3.73 (2H, t, J=6 Hz, NC$\underline{H}_2$CH$_2$O), 4.10-4.30 (3H, m, NCH$_2$C$\underline{H}_2$O, C$\underline{H}$CH$_2$CH$_2$CH$_2$), 4.42 (1H, s, OC$\underline{H}_2$Ph), 4.44 (1H, s, OC$\underline{H}_2$Ph), 4.80 (1H, s, N(CH$_3$)C$\underline{H}_2$Ph), 4.81 (1H, s, N(CH$_3$)C$\underline{H}_2$Ph), 6.90-7.50 (14H, m).

Example 5d 9-(2-hydroxy-ethyl)-2,3,4,9-tetrahydro-1H-carbazole-4-carboxylic acid benzyl-methyl-amide (28)

To a solution of 9-(2-benzyloxy-ethyl)-2,3,4,9-tetrahydro-1H-carbazole-4-carboxylic acid benzyl-methyl-amide (27) (246 mg, 0.5 mmol) in methanol (15 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo to afford 36 mg (20%) of 9-(2-hydroxy-ethyl)-2,3,4,9-tetrahydro-1H-carbazole-4-carboxylic acid benzyl-methyl-amide (28) as a green oil which was used in the next step without purification. The structure was confirmed by $^1H$ NMR ($CDCl_3$) $\delta_H$ 1.80-2.20 (4H, m), 2.70-3.00 (2H, m), 3.20-4.30 (10H, m), 6.90-7.50 (9H, m).

Example 5(e)

Methanesulfonic acid 2-[4-(benzyl-methyl-carbamoyl)-1,2,3,4-tetrahydro-carbazol-9-yl]-ethyl ester To a solution of 9-(2-hydroxy-ethyl)-2,3,4,9-tetrahydro-1H-carbazole-4-carboxylic acid benzyl-methyl-amide (28) (36 mg, 0.1 mmol) in dichloromethane (2 mL) was added pyridine (7.91 g, 1.0 mmol, 8.1 mL). The reaction was cooled to 0° C. and methanesulfonyl chloride (57 mg, 0.5 mmol, 0.04 mL) was added. The reaction was allowed to warm to room temperature overnight. The mixture was washed with 2 N HCl (2×10 mL) and water (2×10 mL), dried and concentrated in vacuo. The crude material was purified by silica gel chromatography eluting with petrol (A) and ethyl acetate (B) (20-80% B, 4 g, 45 CV, 18 mL/min) to afford 14 mg (32%) of methanesulfonic acid 2-[4-(benzyl-methyl-carbamoyl)-1,2,3,4-tetrahydro-carbazol-9-yl]-ethyl ester as a yellow oil. The structure was confirmed by $^1H$ NMR ($CDCl_3$) $\delta_H$ 1.10-2.40 (5H, m), 2.51 (1.5H, s, OSO$_2$C$\underline{H}_3$), 2.54 (1.5H, s, OSO$_2$C$\underline{H}_3$), 2.70-2.90 (2H, m), 3.08 (1.5H, s, NC$\underline{H}_3$), 3.15 (1.5H, s, NC$\underline{H}_3$), 3.40-3.70 (1H, m), 4.10-4.80 (4H, m), 7.00-7.50 (9H, m).

Example 5(f)

9-(2-[$^{18}F$]fluoro-ethyl)-2,3,4,9-tetrahydro-1H-carbazole-4-carboxylic acid benzyl-methyl-amide (imaging agent 7)

Labelling of methanesulfonic acid 2-[4-(benzyl-methyl-carbamoyl)-1,2,3,4-tetrahydro-carbazol-9-yl]-ethyl ester with $^{18}F$ was carried out as described in Example 1(f). Semi-preparative HPLC: HICHROM ACE 5 C18 column (100× mm i.d.), particle size 5 μm; mobile phase A: Water, mobile phase B: Methanol; flow gradient: 3 ml/min; 0-1 min 50% B; 1-20 mins 50-95% B; Wavelength 254 nm; $t_R$ imaging agent 7, 17 mins.

Figure 3:
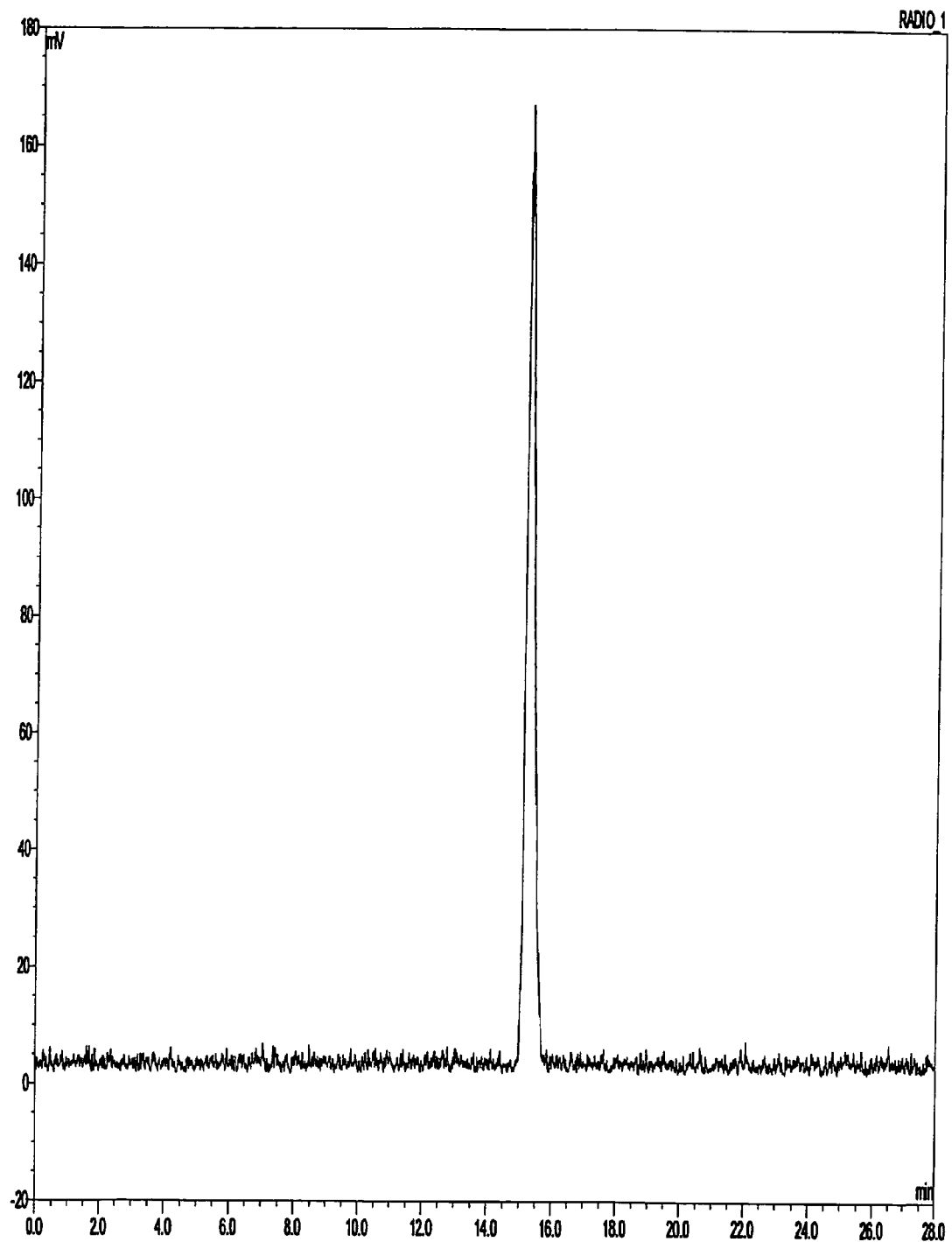
FIG. 3 shows co-elution of imaging agent 7 (prepared according to Example 5) and non-radioactive imaging agent 7 (prepared according to Example 6).

Analytical-HPLC: Phenomenex Luna C18 column (150× 4.6 mm i.d.), particle size 5 μm; mobile phase A: Water, mobile phase B: Methanol; flow gradient: 1 ml/min; 0-1 min 50% B; 1-20 mins 50-95% B; Wavelength 230 nm; $t_R$ imaging agent 7 16 mins. Radiochemical yield 23±2% (n=3) non-decay corrected, time 90-120 mins, radiochemical purity ≥99%. FIG. 3 shows co-elution of imaging agent 7 and non-radioactive imaging agent 7 (prepared according to Example 6).

Example 6

9-(2-fluoro-ethyl)-2,3,4,9-tetrahydro-1H-carbazole-4-carboxylic acid benzyl-methyl-amide (non-radioactive imaging agent 7)

Example 6(a)

3-Bromo-2-hydroxy-cyclohex-1-enecarboxylic acid ethyl ester (29)

Ethyl 2-oxocyclohexanecarboxylate (5.0 g, 29 mmol, 4.7 mL) was dissolved in diethyl ether (5 mL) and cooled to 0° C. under $N_2$. Bromine (4.6 g, 29 mmol, 4.2 mL) was added dropwise over 15 min and the reaction mixture was allowed to warm to room temperature over 90 min. The mixture was slowly poured into ice-cold saturated aqueous sodium carbonate solution (40 mL) and extracted with ethyl acetate (3×40 mL). The combined organic layers were dried and concentrated in vacuo to afford 5.96 g (81%) of 3-bromo-2-hydroxy-cyclohex-1-enecarboxylic acid ethyl ester (29) as a pale yellow oil which was used in the next step without purification. The structure was confirmed by $^{13}$C NMR (75 MHz, DMSO-$d_6$) $\delta_C$ 14.14, 17.65, 21.77, 32.02, 59.95, 60.83, 99.70, 166.33, 172.81.

Example 6(b)

9-(2-Fluoro-ethyl)-2,3,4,9-tetrahydro-1H-carbazole-4-carboxylic acid ethyl ester (30)

A mixture of (2-fluoro-ethyl)-phenyl-amine (24; prepared according to Example 4(a)) (560 mg, 4.0 mmol) and 3-bromo-2-hydroxy-cyclohex-1-enecarboxylic acid ethyl ester (29) (500 mg, 2.0 mmol) was stirred under $N_2$ at 50° C. for 3 h and the reaction turned brown. The resulting mixture was dissolved in propan-2-ol (4 mL) and dry zinc chloride (820 mg, 6 mmol) was added. The mixture was heated to reflux under $N_2$ for 16 h and then concentrated in vacuo. The product was dissolved in ethyl acetate/ether (30 mL/150 mL) and washed with 2 N HCl (40 mL), water (2×100 mL) and aqueous potassium carbonate solution (2×100 mL) then dried and concentrated to afford 447 mg (91%) of 9-(2-fluoro-ethyl)-2,3,4,9-tetrahydro-1H-carbazole-4-carboxylic acid ethyl ester (30) as a yellow oil which was used in the next step without purification. The structure was confirmed by $^{13}$C NMR (75 MHz, CDCl$_3$) $\delta_C$ 14.3, 20.4, 21.7, 26.4, 38.5, 43.1 (d, $J_{CF}$=15 Hz), 60.6, 76.6, 77.0, 77.4, 82.1 (d, $J_{CF}$=173 Hz), 106.9, 108.5, 118.9, 119.4, 121.1, 127.1, 136.2, 136.7, 174.9.

Example 6(c)

9-(2-Fluoro-ethyl)-2,3,4,9-tetrahydro-1H-carbazole-4-carboxylic acid (31)

9-(2-Fluoro-ethyl)-2,3,4,9-tetrahydro-1H-carbazole-4-carboxylic acid ethyl ester (30) (380 mg, 1.3 mmol) was dissolved in ethanol (3 mL) and then NaOH (520 nm) in water (5 mL) was added The reaction was heated at reflux for 2 h. The reaction was concentrated in vacuo and the residue diluted with water and washed with dichloromethane (2×50 mL). The aqueous layer was added drop wise to 2 N HCl (50 mL) and then extracted into dichloromethane (3×50 mL).

The organics were dried and concentrated in vacuo to afford 130 mg (37%) of 9-(2-fluoro-ethyl)-2,3,4,9-tetrahydro-1H-carbazole-4-carboxylic acid (31) as a yellow solid which was used in the next step without purification. The structure was confirmed by $^1$H NMR (300 MHz, CDCl$_3$) $\delta$ 1.90-2.42 (4H, m, 2- and 3-C$\underline{H}_2$), 2.60-2.91 (2H, m, 1-C$\underline{H}_2$), 3.94 (1H, t, J=6 Hz, 4-C$\underline{H}$), 4.30 (1H, t, J=6 Hz, NC$\underline{H}_2$CH$_2$F), 4.37 (1H, t, J=6 Hz, NC$\underline{H}_2$CH$_2$F), 4.59 (1H, t, J=6 Hz, NCH$_2$C$\underline{H}_2$F), 4.74 (1H, t, J=6 Hz, NCH$_2$C$\underline{H}_2$F), 7.05-7.26 (3H, m, Ar$\underline{H}$), 7.59 (1H, d, J=9 Hz, Ar$\underline{H}$).

Example 6(d)

9-(2-Fluoro-ethyl)-2,3,4,9-tetrahydro-1H-carbazole-4-carbonyl chloride (32)

9-(2-Fluoro-ethyl)-2,3,4,9-tetrahydro-1H-carbazole-4-carboxylic acid (31) (0.5 g, 1.91 mmol) in dry dichloromethane (6 mL) was stirred under an atmosphere of nitrogen at room temperature with oxalyl chloride (490 mg, 3.8 mmol, 0.34 mL) and a drop of DMF. The reaction was concentrated in vacuo to afford 545 mg (quantitative) of 9-(2-fluoro-ethyl)-2,3,4,9-tetrahydro-1H-carbazole-4-carbonyl chloride (32) which was used in the next step without purification. The structure was confirmed by $^{13}$C NMR (75 MHz, CDCl$_3$) $\delta_C$ 20.2, 21.6, 26.7, 43.1, 43.4, 50.6, 80.9, 83.1, 105.3, 108.8, 118.3, 120.0, 121.6, 126.5, 136.2, 137.5, 176.1.

Example 6(e)

9-(2-Fluoro-ethyl)-2,3,4,9-tetrahydro-1H-carbazole-4-carboxylic acid benzyl-methyl-amide (non-radioactive imaging agent 7)

9-(2-Fluoro-ethyl)-2,3,4,9-tetrahydro-1H-carbazole-4-carbonyl chloride (32) (110 mg, 0.4 mmol) was dissolved in dichloromethane (1 mL) and cooled to 0° C. N-Benzylmethylamine (92 mg, 0.8 mmol, 98 μL) was then added and the reaction was stirred overnight at RT. The reaction was quenched with 10% aqueous potassium carbonate solution (2 mL). The dichloromethane layer was collected through a phase separator then concentrated in vacuo. The crude material was purified by silica gel chromatography eluting with petrol (A) and ethyl acetate (B) (20-100% B, 12 g, 30 CV, 30 mL/min) to afford 39 mg (28%) of 9-(2-fluoro-ethyl)-2,3,4, 9-tetrahydro-1H-carbazole-4-carboxylic acid benzyl-methyl-amide (non-radioactive imaging agent 7). The structure was confirmed by $^1$H NMR (300 MHz, CDCl$_3$) $\delta_H$ 1.75-2.32, (4H, m, 2- and 3-C$\underline{H}_2$), 2.68-2.86 (2H, m, 1-C$\underline{H}_2$), 3.10 (1H, s, NC$\underline{H}_3$), 3.14 (2H, s, NC$\underline{H}_3$), 4.17-4.39 (3H, m, NC$\underline{H}_2$CH$_2$F and 4-C$\underline{H}_2$), 4.52-4.87 (4H, m, NC$\underline{H}_2$Ph and NCH$_2$C$\underline{H}_2$F), 6.96-7.42 (9H, m, Ar$\underline{H}$).

Example 7

Synthesis of 6-Fluoro-9-(2-[$^{18}$F]fluoro-ethyl)-2,3,4, 9-tetrahydro-1H-carbazole-4-carboxylic acid diethylamide (imaging agent 8)

Example 7(a)

2-benzyloxy-N-(4-fluoro-phenyl)-acetamide (33)

To a solution of benzyloxyacetic acid (4.6 g, 28.0 mmol, 4.0 mL) in DCM (52 mL) was added oxalyl chloride (7.7 g, 61 mmol, 5.3 mL) and a drop of DMF. The reaction mixture was stirred at room temperature for 4 h. Excess of oxalyl chloride was removed in vacuo to give benzyloxy-acetyl chloride. The crude acyl chloride was diluted into DCM (100 mL) and triethylamine (5.3 mL, 41.6 mmol, 4.2 g) was added followed by 4-fluoroaniline (3.5 g, 32 mmol, 3.0 mL). The reaction mixture was stirred at RT overnight. The reaction was then quenched with 1 M aqueous HCl (100 mL), dried and concentrated in vacuo to give 7.1 g (95%) of 2-benzyloxy-N-(4-fluoro-phenyl)-acetamide (33) as a yellow oil which was used in the next step without purification. The structure was confirmed by $^{13}$C NMR (75 MHz, CDCl$_3$) $\delta_C$ 69.2, 73.5, 115.4 (d, $J_{CF}$=22 Hz), 121.4 (d, $J_{CF}$=7 Hz), 127.9, 128.2, 128.5, 132.5 (d, $J_{CF}$=3 Hz), 136.3, 157.6, 160.8, and 167.5.

Example 7(b)

(2-Benzyloxy-ethyl)-(4-fluoro-phenyl)-amine (34)

To a suspension of LAH (1.25 g, 27 mmol) in dry diethyl ether (100 mL) was added dropwise a solution of 2-benzyloxy-N-(4-fluoro-phenyl)-acetamide (33) (6.9 g, 27 mmol) in dry diethyl ether (100 mL). The addition was such as a reflux was maintained. Once the addition was completed, the reaction mixture was heated to reflux for 4 h, then poured into ice-water and DCM was added. In order to break down the aluminium salt, 2M aqueous sodium hydroxide solution was added until strong basic pH was obtained. The layers were separated and the aqueous layer was washed with DCM, dried and concentrated in vacuo. The crude material was purified by silica gel chromatography eluting with petrol (A) and ethyl acetate (B) (5-50% B, 100 g, 12 CV, 60 mL/min) to afford 5.5 g (84%) of (2-benzyloxy-ethyl)-(4-fluoro-phenyl)-amine (34) as a yellow oil. The structure was confirmed by $^{13}$C NMR (75 MHz, CDCl$_3$) $\delta_C$ 44.0, 68.3, 72.8, 113.7 (d, J$_{CF}$=7 Hz), 115.3 (d, J$_{CF}$=22 Hz), 127.5, 127.6 (d, J$_{CF}$=3 Hz), 128.3, 137.8, 144.5, 154.1, and 157.2.

Example 7(c)

3-Bromo-2-oxo-cyclohexanecarboxylic acid diethylamide 35

Ethyl 2-cyclohexone-carboxylate (7.50 mL, 47.0 mmol), DMAP (1.72 g, 14.1 mmol) and diethylamine (9.77 mL, 94.0 mmol) were heated at reflux for 72 hours in toluene (100 mL). The reaction was allowed to cool and the toluene was removed under reduced pressure. The crude oil was purified by silica gel chromatography eluting with petrol (A) and ethyl acetate (B) (1:1, 100 g, SiO$_2$) to afford 6.8 g (73%) of 2-oxo-cyclohexanecarboxylic acid diethylamine as an orange oil. The structure was confirmed by $^{13}$C NMR (CDCl$_3$) $\delta$11.1, 12.7, 21.3, 24.9, 28.5, 39.4, 39.6, 51.7, 166.5, 205.9.

2-oxo-cyclohexanecarboxylic acid diethylamine (3.56 mL, 19.3 mmol) was dissolved in diethyl ether (5 mL) and cooled with stirred to 0° C. under N$_2$. Bromine (0.99 mL, 19.3 mmol) was added drop wise over 15 minutes and the reaction mixture was allowed to warm to room temperature over 3 hours. A solid had precipitated out of the reaction. It was collected by filtration and washed with ether to give 5.85 g (109%) of 3-Bromo-2-oxo-cyclohexanecarboxylic acid diethylamide (35) as a pale yellow solid. The structure was confirmed by $^{13}$C NMR (CDCl$_3$) $\delta$11.2, 12.8, 22.7, 28.8, 37.6, 37.9, 39.4, 51.0, 55.7, 165.5, 197.2

Example 7(d)

9-(2-Benzyloxy-ethyl)-6-fluoro-2,3,4,9-tetrahydro-1H-carbazole-4-carboxylic acid diethylamide (36)

A mixture of 2-benzyloxy-N-(4-fluoro-phenyl)-acetamide (33) (5.3 g, 22 mmol) and 3-bromo-2-oxo-cyclohexanecarboxylic acid diethylamide (35) (3.0 g, 13 mmol)) was stirred under N$_2$ at 50° C. for 3 h and the reaction turned brown. The resulting mixture was dissolved in propan-2-ol (30 mL) and dry zinc chloride (9.0 g, 66 mmol) was added. The mixture was heated to reflux under N$_2$ for 16 h and then concentrated in vacuo. The residue was dissolved in ethyl acetate (300 mL) and washed with 2 N HCl (100 mL), water (2×100 mL) and aqueous potassium carbonate solution (2×100 mL) then dried and concentrated in vacuo. The crude material was purified by silica gel chromatography eluting with petrol (A) and ethyl acetate (B) (10-50% B, 100 g) to afford 196 mg (11%) of 9-(2-benzyloxy-ethyl)-6-fluoro-2,3,4,9-tetrahydro-1H-carbazole-4-carboxylic acid diethylamide (36) as a white solid. The structure was confirmed by $^1$H NMR (300 MHz, CDCl$_3$) $\delta_H$ 1.14 (3H, t, J=7 Hz, N(CH$_2$CH$_3$)$_2$), 1.30 (3H, t, J=7 Hz, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and NCH$_2$CH$_2$OBn), 3.66-3.75 (1H, m, 4-CH), 4.00-4.25 (2H, m, NCH$_2$CH$_2$OBn), 4.41 (2H, s, OCH$_2$Ph), 6.75-6.95 (2H, m, NCCHCHCFCH), 7.05-7.15 (1H, m, NCCHCHCFCH), and 7.16-7.25 (5H, m, Ph).

Example 7(d)

6-Fluoro-9-(2-hydroxy-ethyl)-2,3,4,9-tetrahydro-1H-carbazole-4-carboxylic acid diethylamide (37)

To a solution of 9-(2-benzyloxy-ethyl)-6-fluoro-2,3,4,9-tetrahydro-1H-carbazole-4-carboxylic acid diethylamide (36) (600 mg, 1.4 mmol) in methanol (40 mL) was added a slurry of Pd/C (100 mg) in methanol (5 mL). The mixture was placed on the Parr hydrogenator and shaken for 24 h under a hydrogen atmosphere. The reaction was filtered through a pad of celite, washed with methanol and concentrated in vacuo to afford 460 mg (80%) of 6-fluoro-9-(2-hydroxy-ethyl)-2,3,4, 9-tetrahydro-1H-carbazole-4-carboxylic acid diethylamide (37) as a yellow oil which was used in the next step without purification. The structure was confirmed by $^1$H NMR (300 MHz, MeOD-d$_3$) $\delta_H$ 1.18 (3H, t, J=9 Hz, N(CH$_2$CH$_3$)$_2$), 1.35 (3H, t, J=9 Hz, N(CH$_2$CH$_3$)$_2$), 1.80-2.20 (4H, m, 2- and 3-CH$_2$), 2.69-3.88 (2H, m, 1-CH$_2$), 3.40-3.86 (6H, m, N(CH$_2$CH$_3$)$_2$ and NCH$_2$CH$_2$OH), 4.03-4.22 (3H, m, NCH$_2$CH$_2$OH and 4-CH), 6.75-6.95 (2H, m, NCCHCHCFCH), and 7.05-7.15 (1H, m, NCCHCHCFCH.

Example 7(e)

Methanesulfonic acid 2-(4-diethylcarbamoyl-6-fluoro-1,2,3,4-tetrahydro-carbazol-9-yl)-ethyl ester To a solution of 6-fluoro-9-(2-hydroxy-ethyl)-2,3,4,9-tetrahydro-1H-carbazole-4-carboxylic acid diethylamide (37) (460 mg, 1.4 mmol) in dichloromethane (20 mL) was added pyridine (1.11 g, 14.0 mmol, 1.1 mL). The reaction was cooled to 0° C. and methanesulfonyl chloride (722 mg, 6.3 mmol, 0.5 mL) was added. The reaction was allowed to warm to room temperature overnight. The mixture was washed with 2 N HCl (2×30 mL) and water (2×30 mL), dried and concentrated in vacuo. The crude material was purified by silica gel chromatography eluting with petrol (A) and ethyl acetate (B) (0-100% (B), 10 g, 45 CV, 30 mL/min) then triturated with diethyl ether to afford 166 mg (30%) of methanesulfonic acid 2-(4-diethylcarbamoyl-6-fluoro-1,2,3,4-tetrahydro-carbazol-9-yl)-ethyl ester as a white solid. The structure was confirmed by $^{13}$C NMR (75 MHz, CDCl$_3$) $\delta_C$ 12.9, 15.0, 21.1, 27.7, 36.1, 36.7, 40.6, 41.7, 67.8, 103.3 (d, J$_{CF}$=23 Hz), 108.7, 109.0, 109.1, 109.4 (d, J$_{CF}$=5 Hz), 126.9 (d, J$_{CF}$=10 Hz), 132.4, 138.4, 156.1, 159.2, and 173.3.

Example 7(f)

6-Fluoro-9-(2-[$^{18}$F]fluoro-ethyl)-2,3,4,9-tetrahydro-1H-carbazole-4-carboxylic acid diethylamide (imaging agent 8)

Labelling of methanesulfonic acid 2-(4-diethylcarbamoyl-6-fluoro-1,2,3,4-tetrahydro-carbazol-9-yl)-ethyl ester with $^{18}$F was carried out as described in Example 1(f).

Semi-preparative HPLC: HICHROM ACE 5 C18 column (100×10 mm i.d.), particle size 5 μm; mobile phase A: Water, mobile phase B: Methanol; flow gradient: 3 ml/min; 0-1 min 40% B; 1-20 mins 40-95% B; Wavelength 254 nm; t$_R$ imaging agent 8 15 mins.

Figure 4:
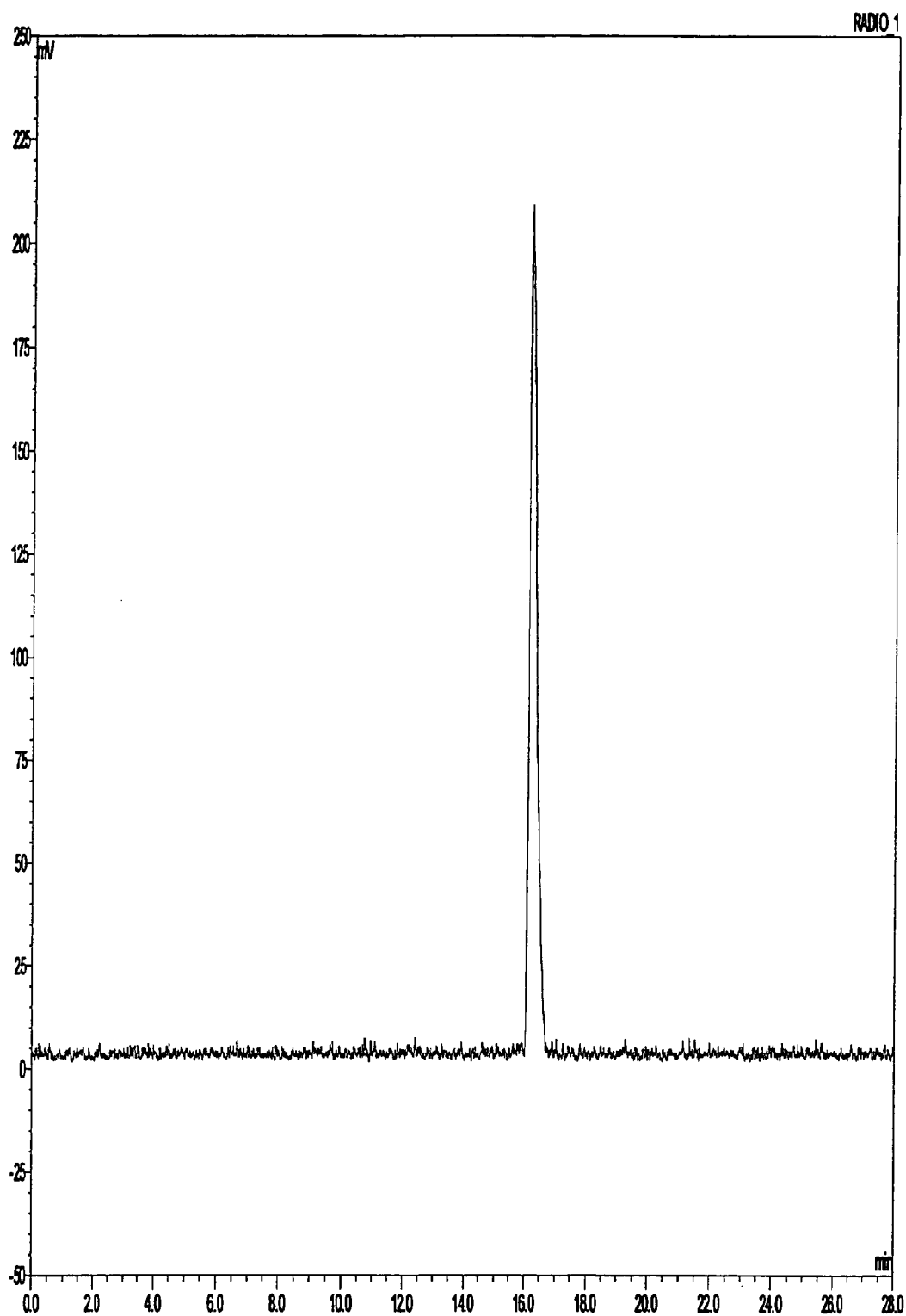
FIG. 4 shows co-elution of imaging agent 8 (prepared according to Example 7) and non-radioactive imaging agent 8 (prepared according to Example 8).

Analytical-HPLC: Phenomenex Luna C18 column (150× 4.6 mm i.d.), particle size 5 μm; mobile phase A: Water, mobile phase B: Methanol; flow gradient: 1 ml/min; 0-1 min 50% B; 1-20 mins 50-95% B; Wavelength 230 nm; $t_R$ imaging agent 8 14 mins. Radiochemical yield 26±8% (n=4) non-decay corrected, time 90-120 mins, radiochemical purity ≥99%. FIG. 4 shows co-elution of imaging agent 8 and non-radioactive imaging agent 8 (prepared according to Example 8).

Example 8

Synthesis of 6-Fluoro-9-(2-fluoro-ethyl)-2,3,4,9-tetrahydro-1H-carbazole-4-carboxylic acid diethylamide (non-radioactive imaging agent 8)

Example 8(a)

(2-Fluoro-ethyl)-(4-fluoro-phenyl)-amine (38)

In a round bottom flask 4-fluoroaniline (1.3 g, 11.6 mmol, 1.6 mL) 2,6-lutidine (1.24 g, 11.6 mmol) and 2-fluoroethyl tosylate (12; prepared according to Example 2(a)) (2.5 g, 11.6 mmol) were combined in DMF (5 mL) and stirred at 100° C. overnight. The reaction was allowed to cool and then diluted with ethyl acetate (100 mL). This was washed with water (3×40 mL) and the organics were dried and concentrated in vacuo. The crude material was purified by silica gel chromatography eluting with petrol (A) and ethyl acetate (B) (10% B, 100 g, 12 CV, 60 mL/min) to afford 383 mg (20%) of (2-fluoro-ethyl)-(4-fluoro-phenyl)-amine (38) as a yellow oil. The structure was confirmed by $^1$H NMR (300 MHz, CDCl$_3$) $\delta_H$ 3.30-3.35 (1H, m, NCH$_2$CH$_2$F), 3.40-3.45 (1H, m, NCH$_2$CH$_2$F), 3.90 (1H, s, br, NH), 4.53 (1H, t, J=3 Hz, NCH$_2$CH$_2$F), 4.69 (1H, t, J=3 Hz, NCH$_2$CH$_2$F), 6.51-6.72 (2H, m, 2×NCCH), 6.85-7.05 (2H, m, 2×NCCHCH).

Example 8b

6-Fluoro-9-(2-fluoro-ethyl)-2,3,4,9-tetrahydro-1H-carbazole-4-carboxylic acid diethylamide (non-radioactive imaging agent 8)

A mixture of 3-bromo-2-oxo-cyclohexanecarboxylic acid diethylamide (35; prepared according to Example 7(c)) (336 mg, 1.2 mmol) and (2-fluoro-ethyl)-(4-fluoro-phenyl)-amine (38) (383 mg, 2.4 mmol) was stirred under N$_2$ at 500° C. for 3 h and the reaction turned brown. The resulting mixture was dissolved in propan-2-ol (2 mL) and dry zinc chloride (491 mg, 3.6 mmol) was added. The mixture was heated to reflux under N$_2$ for 16 h and then concentrated in vacuo. The residue was dissolved in ethyl acetate (20 mL) and washed with 2 N HCl (10 mL), water (2×10 mL) and aqueous potassium carbonate solution (2×5 mL) then dried and concentrated in vacuo. The crude material was triturated with diethyl ether to afford 40 mg (10%) of 6-fluoro-9-(2-fluoro-ethyl)-2,3,4,9-tetrahydro-1H-carbazole-4-carboxylic acid diethylamide (non-radioactive imaging agent 8) as white solid. The structure was confirmed by $^1$H NMR (300 MHz, CDCl$_3$) $\delta_H$ 1.13 (3H, t, J=9 Hz, N(CH$_2$CH$_3$)$_2$), 1.30 (3H, t, J=9 Hz, N(CH$_2$CH$_3$)$_2$), 1.55-2.14 (4H, m, 2- and 3-CH$_2$), 2.78-2.86 (2H, m, 1-CH$_2$), 3.36-3.67 (4H, m, N(CH$_2$CH$_3$)$_2$), 4.00-4.10 (1H, m, 4-CH), 4.30 (2H, dm, J=21 Hz, NCH$_2$CH$_2$F), 4.60 (2H, dm, J=41 Hz, NCH$_2$CH$_2$F), 6.75-6.95 (2H, m, NCCHCHCFCH), and 7.05-7.15 (1H, m, NCCHCHCFCH).

Example 9

Synthesis of 5-Fluoro-9-(2-[$^{18}$F]fluoro-ethyl)-2,3,4,9-tetrahydro-1H-carbazole-4-carboxylic acid diethylamide (imaging agent 10)

Example 9(a)

2-benzyloxy-N-(3-fluoro-phenyl)-acetamide (39)

To a solution of benzyloxyacetic acid (4.65 g, 28 mmol, 4.0 mL) in DCM (52 mL) was added oxalyl chloride (7.7 g, 61 mmol, 5.3 mL) and a drop of DMF. The reaction mixture was stirred at room temperature for 4 h. Excess of oxalyl chloride was removed in vacuo and the crude acyl chloride was diluted into DCM (100 mL) and triethylamine (5.3 mL, 41.6 mmol, 4.2 g) was added followed by 3-fluoroaniline (3.5 g, 32 mmol, 3.0 mL). The reaction mixture was stirred at RT overnight. The reaction was then quenched with 1 M aqueous HCl (100 mL), dried and concentrated in vacuo to afford 7.10 g (95%) of 2-benzyloxy-N-(3-fluoro-phenyl)-acetamide (39) as a yellow oil which was used in the next step without purification. The structure was confirmed by $^{13}$C NMR (75 MHz, CDCl$_3$) $\delta_C$ 69.2, 73.5, 106.9, 107.2, 111.0 (d, $J_{CF}$=24 Hz), 114.9 (d, $J_{CF}$=3 Hz), 127.8, 128.2, 128.5, 129.7 (d, $J_{CF}$=9 Hz), 136.2, and 167.6.

Example 9(b)

(2-Benzyloxy-ethyl)-(3-fluoro-phenyl)-amine (40)

To a suspension of LAH (1.25 g, 27 mmol) in dry diethyl ether (100 mL) was added dropwise a solution of 2-benzyloxy-N-(3-fluoro-phenyl)-acetamide (39) (7.0 g, 27 mmol) in dry diethyl ether (100 mL). The addition was such as a reflux was maintained. Once the addition was completed, the reaction mixture was heated to reflux for 4 h, then poured into ice-water and DCM was added. In order to break down the aluminium salt, 2M aqueous sodium hydroxide solution was added until strong basic pH was obtained. The layers were separated and the aqueous layer was washed with DCM, dried and concentrated in vacuo. The crude material was purified by silica gel chromatography eluting with petrol (A) and ethyl acetate (B) (5-50% B, 100 g, 12 CV, 60 mL/min) to afford 4.1 g (84%) of (2-benzyloxy-ethyl)-(3-fluoro-phenyl)-amine (40) as a yellow oil. The structure was confirmed by $^{13}$C NMR (75 MHz, CDCl$_3$): $\delta_C$ 43.3, 68.2, 73.0, 99.4 (d, $J_{CF}$=24 Hz), 103.5, 103.8, 108.8, 127.4 (d, $J_{CF}$=3 Hz), 127.6, 128.4, 130.0 (d, $J_{CF}$=9 Hz), and 138.8.

Example 9(c)

9-(2-Benzyloxy-ethyl)-5-fluoro-2,3,4,9-tetrahydro-1H-carbazole-4-carboxylic acid diethylamide (41)

A mixture of 3-bromo-2-oxo-cyclohexanecarboxylic acid diethylamide (35; prepared according to Example 7(c)) (2.3 g, 10 mmol) and (2-benzyloxy-ethyl)-(3-fluoro-phenyl)-amine (40) (4.1 g, 17 mmol) was stirred under N$_2$ at 50° C. for 3 h and the reaction turned brown. The resulting mixture was dissolved in propan-2-ol (10 mL) and dry zinc chloride (4.09 g, 30 mmol) was added. The mixture was heated to reflux under N$_2$ for 16 h and then concentrated in vacuo. The residue was dissolved in ethyl acetate (200 mL) and washed with 2 N HCl (50 mL), water (2×50 mL) and aqueous potassium carbonate solution (2×50 mL) then dried and concentrated in vacuo. The crude material was purified by silica gel chromatography eluting with petrol (A) and ethyl acetate (B) (5-100% B, 100 g, 28 CV, 60 mL/min) to afford 1.3 g (30%) of 9-(2-benzyloxy-ethyl)-5-fluoro-2,3,4,9-tetrahydro-1H-carbazole-4-carboxylic acid diethylamide (41) along with the isomer 9-(2-benzyloxy-ethyl)-7-fluoro-2,3,4,9-tetrahydro-1H-carbazole-4-carboxylic acid diethylamide as a mixture which was used in the next step without purification. The structure of 9-(2-benzyloxy-ethyl)-5-fluoro-2,3,4,9-tetrahydro-1H-carbazole-4-carboxylic acid diethylamide (41) was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OBn), 4.00-4.30 (3H, m, CH$_2$CH$_2$OBn and 4-CH), 4.43 (2H, s, OCH$_2$Ph), 6.55-6.65 (1H, m, NCCHCHCHCF), 6.90-7.05 (1H, m, NCCHCHCHCF), 7.05-7.15 (1H, m, NCCHCHCHCF), and 7.16-7.25 (5H, m, Ph).

The structure of 9-(2-benzyloxy-ethyl)-7-fluoro-2,3,4,9-tetrahydro-1H-carbazole-4-carboxylic acid diethylamide was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and NCH$_2$CH$_2$OBn), 4.00-4.30 (3H, m, NCH$_2$CH$_2$Obn and 4-CH), 4.55 (2H, s, OCH$_2$Ph), 6.70-6.80 (1H, m, NCCHCFCHCH), and 7.00-7.40 (7H, m, NCCHCFCHCH and Ph).

Example 9(d)

5-Fluoro-9-(2-hydroxy-ethyl)-2,3,4,9-tetrahydro-1H-carbazole-4-carboxylic acid diethylamide (42)

To a solution of a mixture of 9-(2-benzyloxy-ethyl)-5-fluoro-2,3,4,9-tetrahydro-1H-carbazole-4-carboxylic acid diethylamide (41) and 9-(2-benzyloxy-ethyl)-7-fluoro-2,3,4,9-tetrahydro-1H-carbazole-4-carboxylic acid diethylamide (1.3 g, 3.0 mmol) in methanol (75 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo to afford 743 mg (80%) of a mixture of 5-fluoro-9-(2-hydroxy-ethyl)-2,3,4,9-tetrahydro-1H-carbazole-4-carboxylic acid diethylamide (42) and 7-fluoro-9-(2-hydroxy-ethyl)-2,3,4,9-tetrahydro-1H-carbazole-4-carboxylic acid diethylamide as a yellow oil which was used in the next step without purification. The structure of 5-fluoro-9-(2-hydroxy-ethyl)-2,3,4,9-tetrahydro-1H-carbazole-4-carboxylic acid diethylamide (55) was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OH), 4.00-4.30 (3H, m, CH$_2$CH$_2$OH, 4-CH), 6.55-6.65 (1H, m, NCCHCHCHCF), 6.90-7.05 (1H, m, NCCHCHCHCF), and 7.05-7.15 (1H, m, NCCHCHCHCF).

The structure of 7-fluoro-9-(2-hydroxy-ethyl)-2,3,4,9-tetrahydro-1H-carbazole-4-carboxylic acid diethylamide was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OH), 4.00-4.30 (3H, m, NCH$_2$CH$_2$OH, 4-CH), 6.70-6.80 (1H, m, NCCHCFCHCH), and 7.00-7.40 (2H, m, NCCHCFCHCH).

Example 9(e)

Methanesulfonic acid 2-(4-diethylcarbamoyl-5-fluoro-1,2,3,4-tetrahydro-carbazol-9-yl)-ethyl ester To a solution of a mixture of 5-fluoro-9-(2-hydroxy-ethyl)-2,3,4,9-tetrahydro-1H-carbazole-4-carboxylic acid diethylamide (42) and 7-fluoro-9-(2-hydroxy-ethyl)-2,3,4,9-tetrahydro-1H-carbazole-4-carboxylic acid diethylamide (743 mg, 2.2 mmol) in dichloromethane (30 mL) was added pyridine (1.74 g, 22.0 mmol, 1.8 mL). The reaction was cooled to 0° C. and methanesulfonyl chloride (1.01 g, 8.8 mmol, 0.7 mL) was added. The reaction was allowed to warm to room temperature overnight. The mixture was washed with 2 N HCl (2×50 mL) and water (2×50 mL), dried and concentrated in vacuo. The crude material was purified by semi preparative HPLC eluting with water (A) and methanol (B) (Gemini 5u, C18, 110A, 150×21 mm, 50-95% B over 20 min, 21 mL/min) to afford 10 mg (1%) of methanesulfonic acid 2-(4-diethylcarbamoyl-7-fluoro-1,2,3,4-tetrahydro-carbazol-9-yl)-ethyl ester as a white solid and 30 mg (9%) of a mixture of methanesulfonic acid 2-(4-diethylcarbamoyl-7-fluoro-1,2,3,4-tetrahydro-carbazol-9-yl)-ethyl ester and methanesulfonic acid 2-(4-diethylcarbamoyl-5-fluoro-1,2,3,4-tetrahydro-carbazol-9-yl)-ethyl ester as a white solid. Using these purification conditions, methanesulfonic acid 2-(4-diethylcarbamoyl-5-fluoro-1,2,3,4-tetrahydro-carbazol-9-yl)-ethyl ester could not be isolated as a single component. The structure of methanesulfonic acid 2-(4-diethylcarbamoyl-7-fluoro-1,2,3,4-tetrahydro-carbazol-9-yl)-ethyl ester was confirmed by $^1$H NMR (300 MHz, CDCl$_3$) $\delta_H$ 1.18 (3H, t, J=7 Hz, N(CH$_2$CH$_3$)$_2$), 1.39 (3H, t, J=7 Hz, N(CH$_2$CH$_3$)$_2$) 1.70-2.30 (4H, m, 2- and 3-CH$_2$), 2.58 (3H, s, OSO$_2$CH$_3$), 2.60-2.80 (2H, m, 1-CH$_2$), 3.40-3.65 (4H, m, N(CH$_2$CH$_3$)$_2$), 4.02 (1H, t, J=6 Hz, 4-CH), 4.20 (2H, t, J=7 Hz, NCH$_2$CH$_2$O Ms), 4.35 (2H, t, J=7 Hz, NCH$_2$CH$_2$O Ms), 6.70-6.85 (1H, m, NCCHCFCHCH), 6.90-7.00 (1H, m, NCCHCFCHCH), and 7.05-7.15 (2H, m, NCCHCFCHCH).

The structure of methanesulfonic acid 2-(4-diethylcarbamoyl-5-fluoro-1,2,3,4-tetrahydro-carbazol-9-yl)-ethyl ester was confirmed by $^1$H NMR (300 MHz, CDCl$_3$) $\delta_H$ 1.18 (3H, t, J=7 Hz, N(CH$_2$CH$_3$)$_2$), 1.39 (3H, t, J=7 Hz, N(CH$_2$CH$_3$)$_2$) 1.70-2.30 (4H, m, 2- and 3-CH$_2$), 2.58 (3H, s, OSO$_2$CH$_3$), 2.60-2.80 (2H, m, 1-CH$_2$), 3.40-3.65 (4H, m, N(CH$_2$CH$_3$)$_2$), 4.15 (1H, m, 4-CH), 4.20 (2H, t, J=7 Hz, NCH$_2$CH$_2$OMs), 4.35 (2H, t, J=7 Hz, NCH$_2$CH$_2$OMs), 6.55-6.65 (1H, m, NCCHCHCHCF), 6.90-7.05 (1H, m, NCCHCHCHCF), and 7.05-7.15 (1H, m, NCCHCHCHCF).

Example 9(f)

5-Fluoro-9-(2-[$^{18}$F]fluoro-ethyl)-2,3,4,9-tetrahydro-1H-carbazole-4-carboxylic acid diethylamide (imaging agent 10)

The mixture of methanesulfonic acid 2-(4-diethylcarbamoyl-5-fluoro-1,2,3,4-tetrahydro-carbazol-9-yl)-ethyl ester and methanesulfonic acid 2-(4-diethylcarbamoyl-7-fluoro-1,2,3,4-tetrahydro-carbazol-9-yl)-ethyl ester was used in the radiolabelling reaction. Labelling with $^{18}$F was carried out as described in Example 1(f). 7-Fluoro-9-(2-[$^{18}$F]fluoro-ethyl)-2,3,4,9-tetrahydro-1H-carbazole-4-carboxylic acid diethylamide imaging agent 10 were obtained.

Semi-preparative HPLC: HICHROM ACE 5 C18 column (100×10 mm i.d.), particle size 5 μm; mobile phase A: Water, mobile phase B: Methanol; flow gradient: 3 ml/min; 0-1 min 50% B; 1-20 mins 50-95% B; Wavelength 254 nm; $t_R$ imaging agent 10 15 mins; $t_R$ 7-Fluoro-9-(2-[$^{18}$F]fluoro-ethyl)-2,3,4,9-tetrahydro-1H-carbazole-4-carboxylic acid diethylamide 14 mins.

Figure 5:
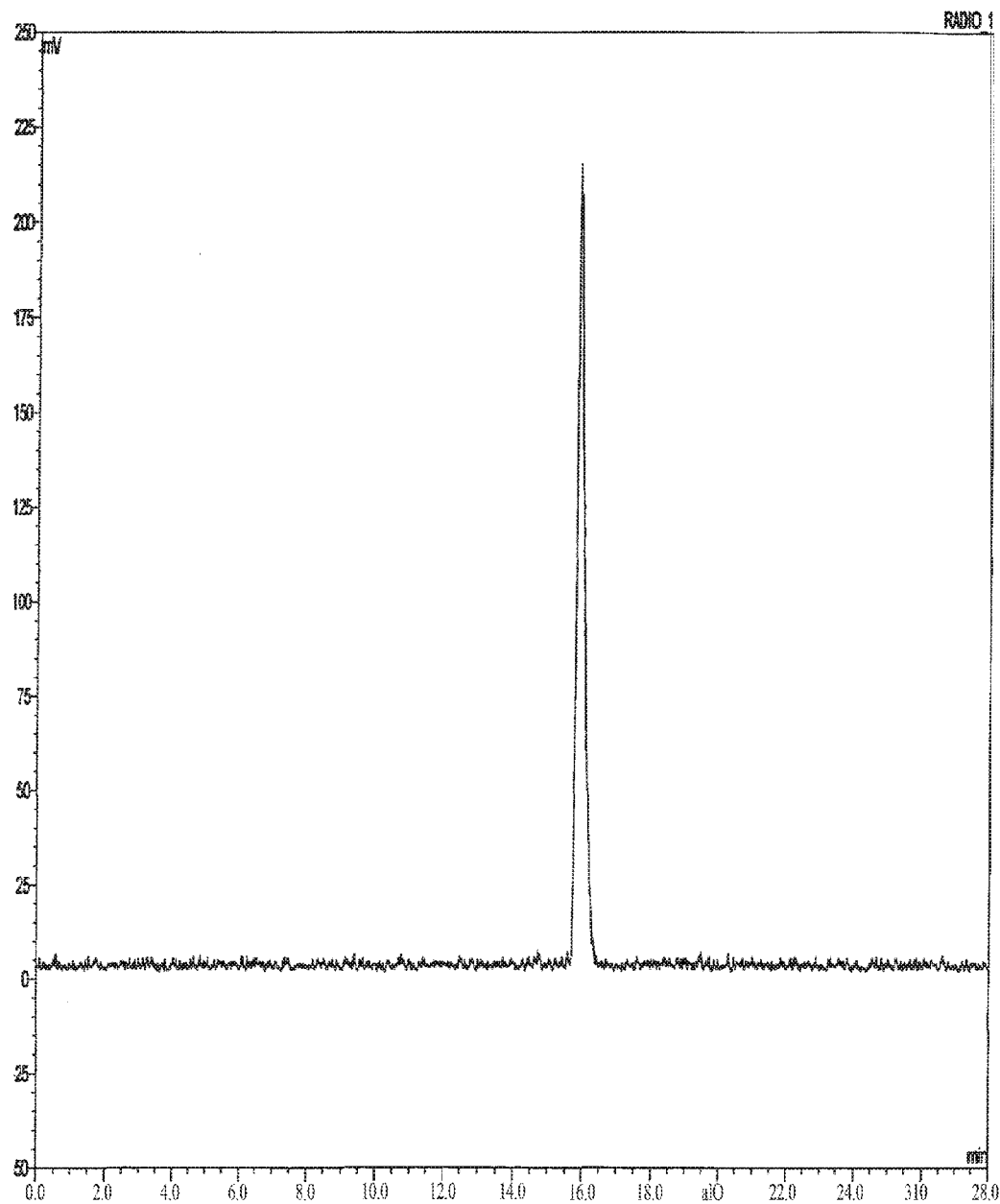
FIG. 5 shows imaging agent 10 (top) and 7-Fluoro-9-(2-[18F]fluoro-ethyl)-2,3,4,9-tetrahydro-1H-carbazole-4-carboxylic acid diethylamide (middle) and 7-Fluoro-9-(2-[19F]fluoro-ethyl)-2,3,4,9-tetrahydro-1H-carbazole-4-carboxylic acid diethylamide (bottom) (each obtained according to Example 9).

Analytical-HPLC: Phenomenex Luna C18 column (150× 4.6 mm i.d.), particle size 5 m; mobile phase A: Water, mobile phase B: Methanol; flow gradient: 1 ml/min; 0-1 min 50% B; 1-20 mins 50-95% B; Wavelength 230 nm; $t_R$ imaging agent 10 16 mins; t$_R$ 7-Fluoro-9-(2-[$^{18}$F]fluoro-ethyl)-2,3,4,9-tetrahydro-1H-carbazole-4-carboxylic acid diethylamide 14 mins. Radiochemical yield of imaging agent 10 8.7±1% (n=3) non-decay corrected, time 90-120 mins, radiochemical purity ≥99%. FIG. 5 shows imaging agent 10 (top) and 7-Fluoro-9-(2-[$^{18}$F]fluoro-ethyl)-2,3,4,9-tetrahydro-1H-carbazole-4-carboxylic acid diethylamide (middle) and 7-Fluoro-9-(2-[$^{19}$F]fluoro-ethyl)-2,3,4,9-tetrahydro-1H-carbazole-4-carboxylic acid diethylamide (bottom).

Example 10

Synthesis of 5-Fluoro-9-(2-fluoro-ethyl)-2,3,4,9-tetrahydro-1H-carbazole-4-carboxylic acid diethylamide (non-radioactive imaging agent 10)

Example 10(a)

(2-fluoro-ethyl)-(3-fluoro-phenyl)-amine (43)

3-Fluoroaniline (1.4 g, 11.6 mmol, 1.2 mL) and 2-fluoroethyl tosylate (12; prepared according to Example 2(a)) (2.5 g, 11.6 mmol) and lutidine (1.24 g, 11.6 mmol) were stirred and heated in DMF (5 mL) at 100° C. overnight. The reaction was allowed to cool and then diluted with ethyl acetate (100 mL). This was washed with water (3×40 mL) and the organics were dried and concentrated in vacuo. The crude material was purified by silica gel chromatography eluting with petrol (A) and ethyl acetate (B) (10% B, 100 g, 12 CV, 60 mL/min) to afford 184 mg (10%) of (2-fluoro-ethyl)-(3-fluoro-phenyl)-amine (43) as a yellow oil. The structure was confirmed by $^1$H NMR (300 MHz, CDCl$_3$) δ$_H$ 3.37 (1H, q, J=6 Hz, NCH$_2$CH$_2$F), 3.46 (1H, q, J=6 Hz, NCH$_2$CH$_2$F), 4.12 (1H, s, br, NH), 4.54 (1H, t, J=3 Hz, NCH$_2$CH$_2$F), 4.69 (1H, t, J=3 Hz, NCH$_2$CH$_2$F), 6.31-6.50 (3H, m, NCCHCHCH), 7.10-7.25 (1H, m, NCCHCF).

Example 10(b)

5-Fluoro-9-(2-fluoro-ethyl)-2,3,4,9-tetrahydro-1H-carbazole-4-carboxylic acid diethylamide (non-radioactive imaging agent 10)

A mixture of 3-bromo-2-oxo-cyclohexanecarboxylic acid diethylamide (35; prepared according to Example 7(c)) (161 mg, 0.6 mmol) and (2-fluoro-ethyl)-(3-fluoro-phenyl)-amine (43) (184 mg, 1.2 mmol) was stirred under N$_2$ at 50° C. for 3 h and the reaction turned brown. The resulting mixture was dissolved in propan-2-ol (1 mL) and dry zinc chloride (245 mg, 1.8 mmol) was added. The mixture was heated to reflux under N$_2$ for 16 h and then concentrated in vacuo. The residue was dissolved in ethyl acetate (10 mL) and washed with 2 N HCl (5 mL), water (2×5 mL) and aqueous potassium carbonate solution (2×5 mL) then dried and concentrated in vacuo. The crude material was purified by semi preparative HPLC eluting with water (A) and methanol (B) (Gemini 5u, C18, 110A, 150×21 mm, 50-95% B over 20 min, 21 mL/min) to afford 20 mg (6%) of 7-fluoro-9-(2-fluoro-ethyl)-2,3,4,9-tetrahydro-1H-carbazole-4-carboxylic acid diethylamide as a white solid and 10 mg (3%) of 5-fluoro-9-(2-fluoro-ethyl)-2,3,4,9-tetrahydro-1H-carbazole-4-carboxylic acid diethylamide (non-radioactive imaging agent 10) as a white solid. The structure of 7-fluoro-9-(2-fluoro-ethyl)-2,3,4,9-tetrahydro-1H-carbazole-4-carboxylic acid diethylamide was confirmed by $^1$H NMR (300 MHz, CDCl$_3$) δ$_H$ 1.14 (3H, t, J=7 Hz, N(CH$_2$CH$_3$)$_2$), 1.33 (3H, t, J=7 Hz, N(CH$_2$CH$_3$)$_2$), 1.80-2.15 (4H, m, 2- and 3-CH$_2$), 2.70-2.80 (2H, m, 1-CH$_2$), 3.50-3.80 (4H, m, N(CH$_2$CH$_3$)$_2$), 4.20-4.35 (1H, m, 4-CH), 4.40 (2H, dm, J=21 Hz, NCH$_2$CH$_2$F), 4.60 (2H, dm, J=41 Hz, NCH$_2$CH$_2$F), 6.70-6.80 (1H, m, NCCHCFCHCH), and 7.00-7.10 (2H, m, NCCHCFCHCH).

The structure of 5-fluoro-9-(2-fluoro-ethyl)-2,3,4,9-tetrahydro-1H-carbazole-4-carboxylic acid diethylamide (non-radioactive imaging agent 10) was confirmed by $^1$H NMR (300 MHz, CDCl$_3$) δ$_H$ 1.14 (3H, t, J=7 Hz, N(CH$_2$CH$_3$)$_2$), 1.33 (3H, t, J=7 Hz, N(CH$_2$CH$_3$)$_2$), 1.80-2.15 (4H, m, 2- and 3-CH$_2$), 2.70-2.80 (2H, m, 1-CH$_2$), 3.50-3.80 (4H, m, N(CH$_2$CH$_3$)$_2$), 4.20-4.35 (1H, m, 4-CH), 4.40 (2H, dm, J=21 Hz, NCH$_2$CH$_2$F), 4.60 (2H, dm, J=41 Hz, NCH$_2$CH$_2$F), 6.55-6.65 (1H, m, NCCHCHCHCF), 6.90-7.05 (1H, m, NCCHCHCHCF), and 7.05-7.15 (1H, m, NCCHCHCHCF).

Example 11

9-(2-[$^{18}$F]Fluoro-ethyl)-2-methyl-2,3,4,9-tetrahydro-1-carbazole-4-carboxylic acid diethylamide (imaging agent 11)

Example 11(a)

4-(4-Methyl-cyclohex-1-enyl)-morpholine (44)

In a flask equipped with a dean stark, a solution of 4-methylcyclohexanone (20.1 g, 179.3 mmol, 22 mL) and morpholine (31.3 g, 359.0 mmol, 31.4 mL) were refluxed in benzene (55 mL) for 26 hours. The benzene was removed under vacuum and the crude product was purified by distillation under reduced pressure to afford 23 g (70%) of 4-(4-methyl-cyclohex-1-enyl)-morpholine (44) as an oil (b.p. 120° C. at 10 mmHg). The structure was confirmed by $^1$H NMR (300 MHz, CDCl$_3$): δ$_H$ 0.94 (3H, d, J=6.0 Hz, CH$_3$), 1.15-1.35 (1H, m, CH$_2$CH=CN), 1.50-1.80 (3H, m, CH$_2$CH$_2$CHCH$_3$), 2.00-2.25 (4H, m, CH$_2$CH=CN and CH$_2$CH$_2$CHCH$_3$), 2.65-2.95 (4H, m, OCH$_2$NCH$_2$), 3.73 (4H, t, J=6.0 Hz, OCH$_2$NCH$_2$), and 4.60-4.65 (1H, m, CH$_2$CH=CN).

Example 11(b)

5-Methyl-2-oxo-cyclohexanecarboxylic acid ethyl ester (45)

To a solution of 4-(4-methyl-cyclohex-1-enyl)-morpholine (44) (23 g, 127.0 mmol) in benzene (55 mL), ethyl chloroformate (7.5 g, 69.0 mmol, 6.6 mL) was added under nitrogen while the enamine solution was being stirred rapidly.

After refluxing for 18 h, the solution was cooled and filtered. The precipitate of enamine hydrochloride was washed with dry ether. The filtrate and washings were returned to the reaction flask and 10% aqueous HCl (40 mL) was added. The mixture was stirred vigorously for 15-30 min. The layers were separated, the aqueous layer was extracted with ethyl acetate (2×100 mL) and the combined organic layers were concentrated in vacuo. The crude material was purified by distillation under reduced pressure to afford 12.5 g (53%) of 5-methyl-2-oxo-cyclohexanecarboxylic acid ethyl ester (45) as an oil (b.p. 85° C.-90° C. at 10 mmHg). The structure was confirmed by $^1$H NMR (300 MHz, CDCl$_3$): δ$_H$ 0.85-0.95 (3H, m, CH$_3$), 1.17 (3H, t, J=7 Hz, OCH$_2$CH$_3$), 1.25-2.00 (5H, m, 5-CH, 4- and 6-CH$_2$), 2.15-2.40 (3H, m, 1-CH and 3-CH$_2$), and 4.00-4.20 (2H, m, OCH$_2$CH$_3$).

Example 11(c)

5-Methyl-2-oxo-cyclohexanecarboxylic acid diethylamide (46)

5-Methyl-2-oxo-cyclohexanecarboxylic acid ethyl ester (45) (5.9 g, 32 mmol), DMAP (1.12 g, 10 mmol) and diethylamine (4.7 g, 65 mmol, 6.7 mL) in toluene (90 mL) were heated at reflux for 4 days. The reaction was allowed to cool and the toluene was removed under reduced pressure to give a yellow oil. The crude material was purified by silica gel chromatography eluting with petrol (A) and ethyl acetate (B) (20-50% B, 80 g) to afford 4.4 g (65%) of 5-methyl-2-oxo-cyclohexanecarboxylic acid diethylamide (46) as a yellow oil. The structure was confirmed $^1$H NMR (300 MHz, CDCl$_3$) $\delta_H$ 0.8-1.05 (9H, m, CH$_3$ and N(CH$_2$CH$_3$)$_2$), 1.05-2.10 (5H, m, 5-CH and 4- and 6-CH$_2$), 2.15-2.80 (2H, m, 3-CH$_2$), 2.95-3.55 (5H, m, 1-CH and N(CH$_2$CH$_3$)$_2$).

Example 11(d)

3-Bromo-2-hydroxy-5-methyl-cyclohex-1-enecarboxylic acid diethylamide (47)

5-methyl-2-oxo-cyclohexanecarboxylic acid diethylamide (46) (4.4 g, 21 mmol) was dissolved in diethyl ether (5 mL) and cooled to 0° C. under N$_2$. Bromine (3.32 g, 21 mmol, 1.1 mL) was added dropwise over 15 min and the reaction mixture was allowed to warm to room temperature over 90 min. The mixture was slowly poured into ice-cold saturated aqueous sodium carbonate solution (40 mL) and extracted with ethyl acetate (3×40 mL). The combined organic layers were dried and concentrated in vacuo to afford 6.1 g (quantitative) of 3-bromo-2-hydroxy-5-methyl-cyclohex-1-enecarboxylic acid diethylamide (47) as an off-white solid. The structure was confirmed by $^1$H NMR (300 MHz, CDCl$_3$) $\delta_H$ 0.8-1.20 (9H, m, CH$_3$ and N(CH$_2$CH$_3$)$_2$), 1.80-2.40 (5H, m, CH$_2$CH(CH$_3$)CH$_2$), 3.15-3.55 (4H, m, N(CH$_2$CH$_3$)$_2$), 4.65-4.74 (1H, m, CHBr), and 12.04 (1H, s, OH).

Example 11(e)

9-(2-Benzyloxy-ethyl)-2-methyl-2,3,4,9-tetrahydro-1H-carbazole-4-carboxylic acid diethylamide (48)

A mixture of 3-bromo-2-hydroxy-5-methyl-cyclohex-1-enecarboxylic acid diethylamide (47) (4.0 g, 14 mmol) and (2-benzyloxy-ethyl)-phenyl-amine (21; prepared according to Example 3(c)) (6.3 g, 28 mmol) was stirred under N$_2$ at 50° C. for 3 h and the reaction turned brown. The resulting mixture was dissolved in propan-2-ol (14 mL) and dry zinc chloride (5.72 g, 42 mmol) was added. The mixture was heated to reflux under N$_2$ for 16 h and then concentrated in vacuo. The residue was dissolved in ethyl acetate (200 mL) and washed with 2 N HCl (50 mL), water (2×50 mL) and aqueous potassium carbonate solution (2×50 mL) then dried and concentrated in vacuo. The crude mixture was purified by SCX cartridge (40 mL) and then silica gel chromatography eluting with petrol (A) and ethyl acetate (B) (10-50% B, 100 g, 12 CV, 85 mL/min) to afford 467 mg (8%) of 9-(2-Benzyloxy-ethyl)-2-methyl-2,3,4,9-tetrahydro-1H-carbazole-4-carboxylic acid diethylamide (48) as a white solid. The structure was confirmed by $^1$H NMR (300 MHz, CDCl$_3$) $\delta_H$ 1.20-1.40 (9H, m, CH$_3$ and N(CH$_2$CH$_3$)$_2$), 1.90-2.20 (3H, m, 2-CH and 3-CH$_2$), 2.35-2.45 (1H, m, 1-CH$_2$), 2.85-2.95 (1H, m, 1-CH$_2$), 3.40-3.70 (4H, m, N(CH$_2$CH$_3$)$_2$), 3.70-3.80 (1H, m, 4-CH), 4.10-4.30 (4H, m, NCH$_2$CH$_2$OBn), 4.43 (2H, s, OCH$_2$Ph), and 7.00-7.30 (9H, m, CHCHCHCH and Ph).

Example 11(f)

9-(2-Hydroxy-ethyl)-2-methyl-2,3,4,9-tetrahydro-1H-carbazole-4-carboxylic acid diethylamide 49)

To a solution of 9-(2-benzyloxy-ethyl)-2-methyl-2,3,4,9-tetrahydro-1H-carbazole-4-carboxylic acid diethylamide (48) (460 mg, 1.1 mmol) in methanol (25 mL) was added a slurry of Pd/C (100 mg) in methanol (5 mL). The mixture was placed on the Parr hydrogenator and shaken for 24 h under a hydrogen atmosphere. The reaction was filtered through a pad of celite, washed with methanol and concentrated in vacuo to afford 250 mg (79%) of 9-(2-hydroxy-ethyl)-2-methyl-2,3,4,9-tetrahydro-1H-carbazole-4-carboxylic acid diethylamide (49) as a yellow oil which was used in the next step without purification. The structure was confirmed by $^1$H NMR (300 MHz, CDCl$_3$) $\delta_H$ 1.20-1.40 (9H, m, CH$_3$ and N(CH$_2$CH$_3$)$_2$), 1.90-2.20 (3H, m, 2-CH and 3-CH$_2$), 2.35-2.45 (1H, m, 1-CH$_2$), 2.85-2.95 (1H, m, 1-CH$_2$), 3.40-3.70 (4H, m, N(CH$_2$CH$_3$)$_2$), 3.70-3.80 (1H, m, 4-CH), 4.10-4.30 (4H, m, NCH$_2$CH$_2$OH), 6.91 (1H, t, J=7 Hz, NCCHCHCHCH), 7.00 (1H, t, J=7 Hz, NCCHCHCHCH), 7.12 (1H, d, J=7 Hz, NCCHCHCHCH), and 7.15 (1H, d, J=7 Hz, NCCHCHCHCH).

Example 11(g)

Methanesulfonic acid 2-(4-diethylcarbamoyl-2-methyl-1,2,3,4-tetrahydro-carbazol-9-yl)-ethyl ester To a solution of 9-(2-hydroxy-ethyl)-2-methyl-2,3,4,9-tetrahydro-1H-carbazole-4-carboxylic acid diethylamide (49) (250 mg, 0.8 mmol) in dichloromethane (10 mL) was added pyridine (633 mg, 8.0 mmol, 0.6 mL). The reaction was cooled to 0° C. and methanesulfonyl chloride (367 mg, 3.2 mmol, 0.2 mL) was added. The reaction was allowed to warm to room temperature overnight. The mixture was washed with 2 N HCl (2×20 mL) and water (2×20 mL), dried and concentrated in vacuo. The crude material was purified by silica gel chromatography eluting with petrol (A) and ethyl acetate (B) (0-100% B, 10 g, 34 CV, 30 mL/min) then triturated with diethyl ether to afford 250 mg (80%) of methanesulfonic acid 2-(4-diethylcarbamoyl-2-methyl-1,2,3,4-tetrahydro-carbazol-9-yl)-ethyl ester as a white solid. The structure was confirmed by $^{13}$C NMR (75 MHz, CDCl$_3$) δ 12.9, 13.0, 15.2, 22.0, 29.7, 30.2, 36.7, 36.8, 40.8, 41.6, 42.0, 67.8, 108.6, 109.5, 118.6, 119.6, 121.2, 126.4, 136.2, 136.4, 173.7.

Example 11(h)

9-(2-[$^{18}$F]Fluoro-ethyl)-2-methyl-2,3,4,9-tetrahydro-1H-carbazole-4-carboxylic acid diethylamide (imaging agent 11)

Labelling of methanesulfonic acid 2-(4-diethylcarbamoyl-2-methyl-1,2,3,4-tetrahydro-carbazol-9-yl)-ethyl ester with $^{18}$F was carried out as described in Example 1(f).

Semi-preparative HPLC: HICHROM ACE 5 C18 column (100×10 mm i.d.), particle size 5 μm; mobile phase A: Water, mobile phase B: Methanol; flow gradient: 3 ml/min; 0-26 min 50% B; Wavelength 254 nm; $t_R$ imaging agent 11 15 mins.

Figure 6:
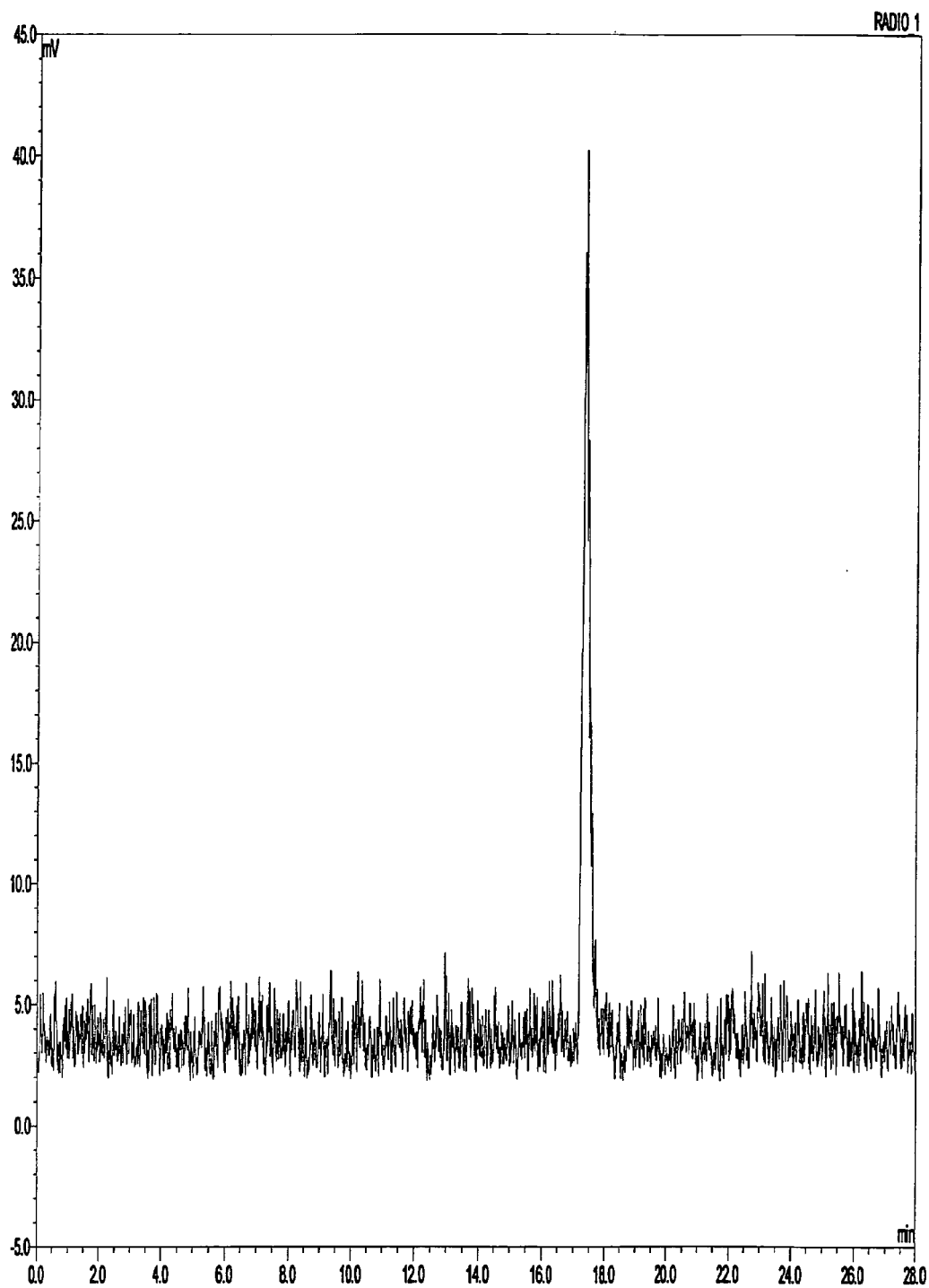
FIG. 6 shows co-elution of imaging agent 11 (prepared according to Example 11) and non-radioactive imaging agent 11 (prepared according to Example 12).

Analytical-HPLC: Phenomenex Luna C18 column (150× 4.6 mm i.d.), particle size 5 μm; mobile phase A: Water, mobile phase B: Methanol; flow gradient: 1 ml/min; 0-1 min 40% B; 1-20 mins 40-95% B; Wavelength 230 nm; $t_R$ imaging agent 11 17 mins. Radiochemical yield 14±13% (n=3) non-decay corrected, time 90-120 mins, radiochemical purity ≥99%. FIG. 6 shows co-elution of imaging agent 11 and non-radioactive imaging agent 11.

Example 12

Synthesis of 9-(2-Fluoro-ethyl)-2-methyl-2,3,4,9-tetrahydro-1H-carbazole-4-carboxylic acid diethylamide (non radioactive imaging agent 11)

A mixture of 3-bromo-2-hydroxy-5-methyl-cyclohex-1-enecarboxylic acid diethylamide (47; prepared according to Example 11(d)) (2.0 g, 7 mmol) and (2-fluoro-ethyl)-phenyl-amine (24; prepared according to Example 4(a)) (1.9 g, 14 mmol) was stirred under $N_2$ at 50° C. for 3 h and the reaction turned brown. The resulting mixture was dissolved in propan-2-ol (7 mL) and dry zinc chloride (2.86 g, 21 mmol) was added. The mixture was heated to reflux under $N_2$ for 16 h and then concentrated in vacuo. The residue was dissolved in ethyl acetate (100 mL) and washed with 2 N HCl (30 mL), water (2×30 mL) and aqueous potassium carbonate solution (2×30 mL) then dried and concentrated in vacuo. The crude mixture was purified by SCX cartridge (40 mL) and then silica gel chromatography eluting with petrol (A) and ethyl acetate (B) (0-100% B, 100 g, 12 CV, 85 mL/min) to afford 400 mg (17%) of 9-(2-fluoro-ethyl)-2-methyl-2,3,4,9-tetrahydro-1H-carbazole-4-carboxylic acid diethylamide (non-radioactive imaging agent 11) as a white solid. The structure was confirmed by $^1$H NMR (300 MHz, CDCl$_3$) $\delta_H$ 1.10-1.35 (9H, m, C$\underline{H}_3$ and N(CH$_2$C$\underline{H}_3$)$_2$), 1.95-2.10 (2H, m, 3-C$\underline{H}_2$), 2.30-2.50 (1H, m, 2-C$\underline{H}$), 2.70-2.80 (2H, m, 1-C$\underline{H}_2$), 3.40-3.70 (4H, m, N(C$\underline{H}_2$CH$_3$)$_2$), 4.05-4.15 (1H, m, 4-C$\underline{H}$), 4.30 (2H, dm, J=21 Hz, NC$\underline{H}_2$CH$_2$F), 4.65 (2H, dm, J=41 Hz, NCH$_2$C$\underline{H}_2$F), and 7.00-7.30 (4H, m, NCC$\underline{H}$C$\underline{H}$C$\underline{H}$C$\underline{H}$.

Example 13

Preparation of the (S) and (R) Enantiomers of Imaging Agent 5

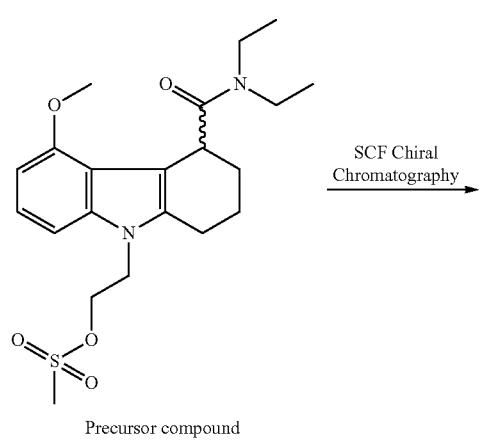

Precursor compound

SCF Chiral Chromatography →

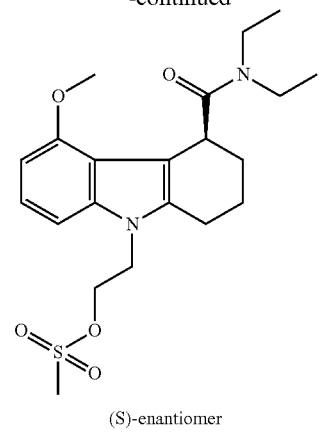

(S)-enantiomer

+

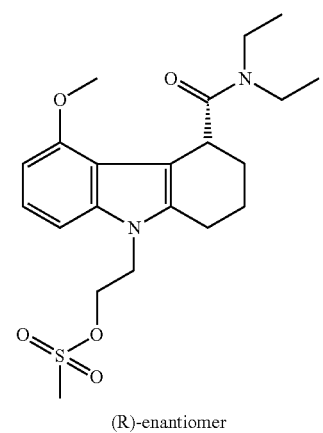

(R)-enantiomer

The precursor compound methanesulphonic acid 2-(4-diethylcarbamyl-5-methoxy-1,2,3,4-tetrahydro-carbazol-9-yl) ethyl ester (obtained as described in Example 1(I)) was separated into its enantiomers using chiral supercritical fluid (CO$_2$) chromatography on a Kromasil Amycoat, 250×10 mm, 5 μm, 100 Å column using 30% IPA at 40° C. at 13 ml a min with a run time of 6 min. 60 mg of the racemate was dissolved in 1,4-Dioxane (2 ml) and up to 200 μl at a time was as injected for each run. Baseline separation between the two enantiomers was achieved. Analytical HPLC determination of the enantiomeric purity of the two separated enantiomers on an IC from Chiral Technologies, 250×4.6 mm, 5 μm, run isocratic, 80:20—MeOH:IPA at 0.5 ml/min and room temperature indicated an enantiomeric purity of 99.5% of each of the enantiomers.

Labelling of the (S) and (R) enantiomers of the precursor compound with $^{18}$F was done using a FASTLab™ (GE Healthcare) cassette. [$^{18}$F]Fluoride supplied from GE Healthcare on a GE PETrace cyclotron was trapped on a QMA cartridge. K222 (8 mg), KHCO3 (200 μl, 0.1M aq.) and MeCN(1 ml) were added to eluant vial 1. 0.6 ml of eluant from eluant vial 1 was used to elute the QMA cartridge. Drying of the $^{18}$F eluate was carried out at 100° C. for 20 mins, followed by cooling to 86° C. before addition of precursor.

3 mg of each of the (S) and (R) enantiomers of the precursor compound was dissolved in 1.6 ml of CH₃CN. 1 ml of this solution was added to the reaction vessel. The reaction vessel was heated at 100° C. for 15 mins. The reaction vessel was then rinsed with 2 ml water.

Semi-preparative HPLC was carried out as follows:

| | |
|---|---|
| 0-40 mins | 45% (B) |
| Column | ACE 5 C18 column, 5u, 100 × 10 mm |
| Eluent | water (pump A):MeCN (pump B) |
| Loop Size | 5 ml |
| Pump speed | 3 ml/min, |
| Wavelength | 254 nm, 2 AUFS |

Figure 7:
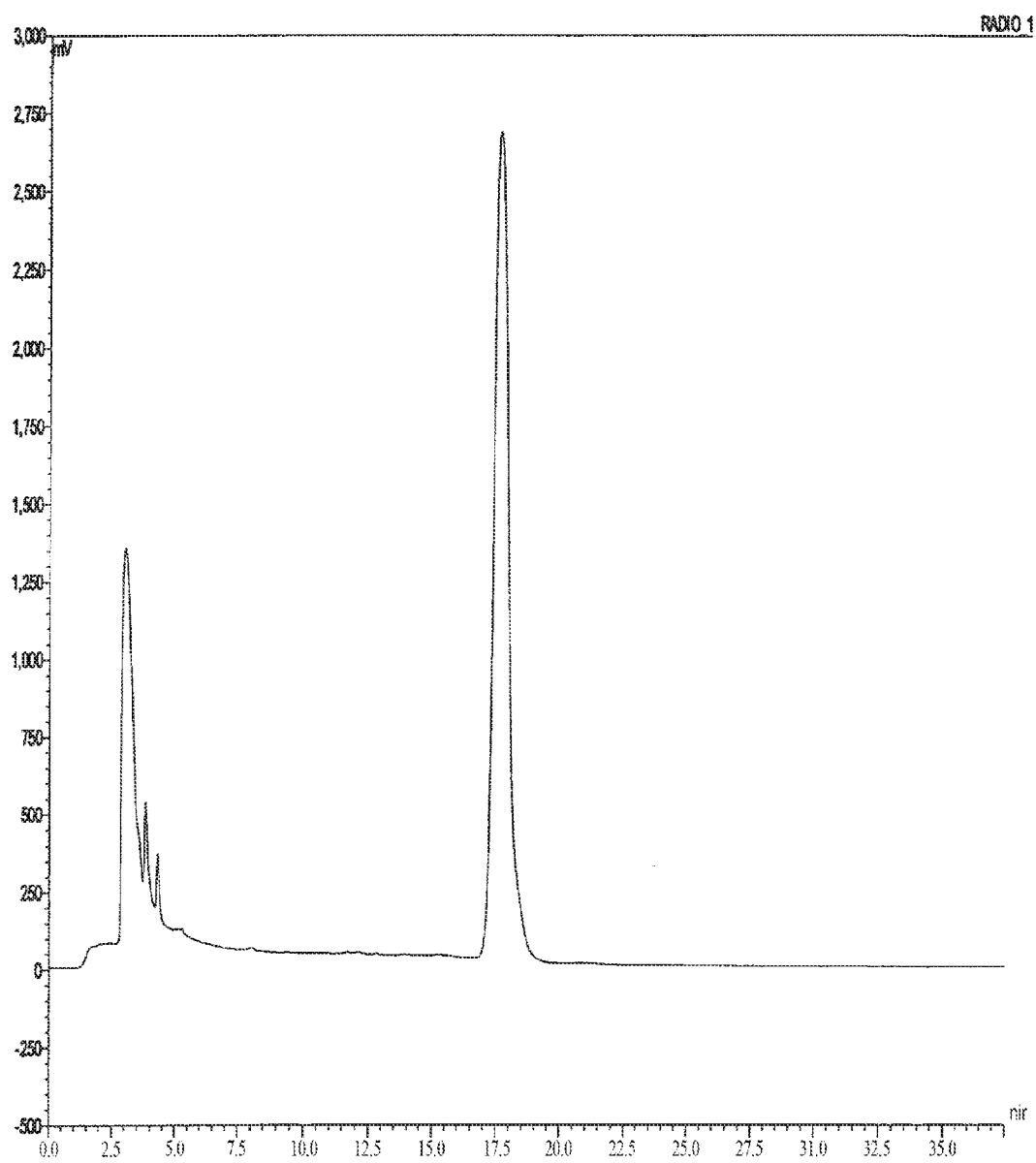
FIGS. 7 and 8 show the radioactive (top) and the UV (bottom) HPLC traces obtained using the above semi-preparative method for the PET tracer of the invention and its alternative enantiomer, respectively.
Figure 8:
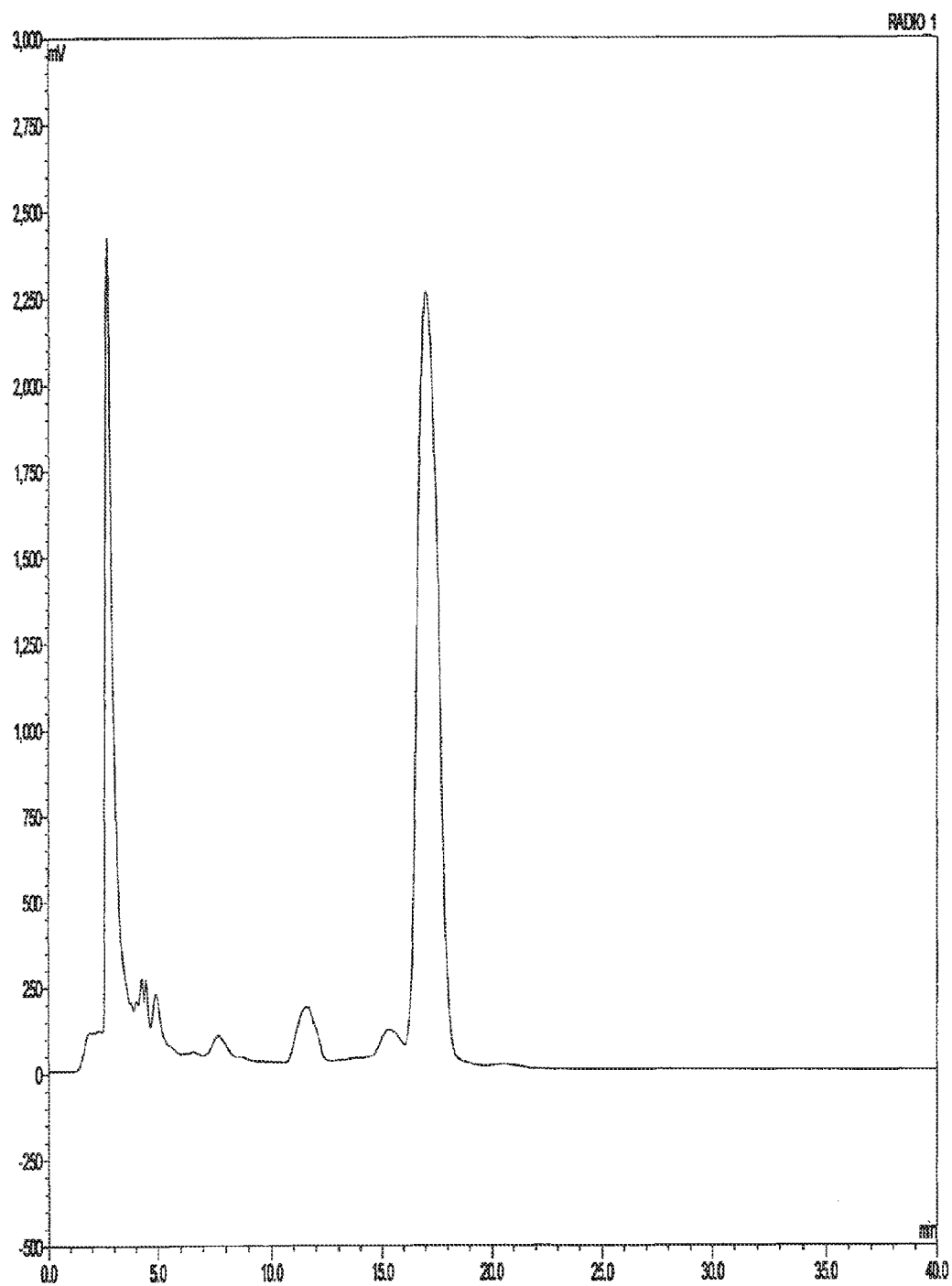

FIGS. 7 and 8 show the radioactive (top) and the UV (bottom) HPLC traces obtained using the above semi-preparative method for the PET tracer of the invention and its alternative enantiomer, respectively.

Analytical achiral HPLC was carried out as follows:

| | |
|---|---|
| 0-25 mins | 60% (B) |
| 25-25.5 mins | 60-95% (B) |
| 25.5-26.5 mins | 95% (B) |
| 26.5-27 mins | 95-60% (B) |
| 27-30 mins | 60% (B) |
| Column | Chromolith RP-18e 100 × 4.6 mm (H10-0022) Luna C18 Guard |
| Eluent | water (pump A):MeOH (pump B) |
| Loop Size | 20 ul |
| Pump speed | 1 ml/min, |
| Wavelength | 254, 230 nm |

Figure 9:
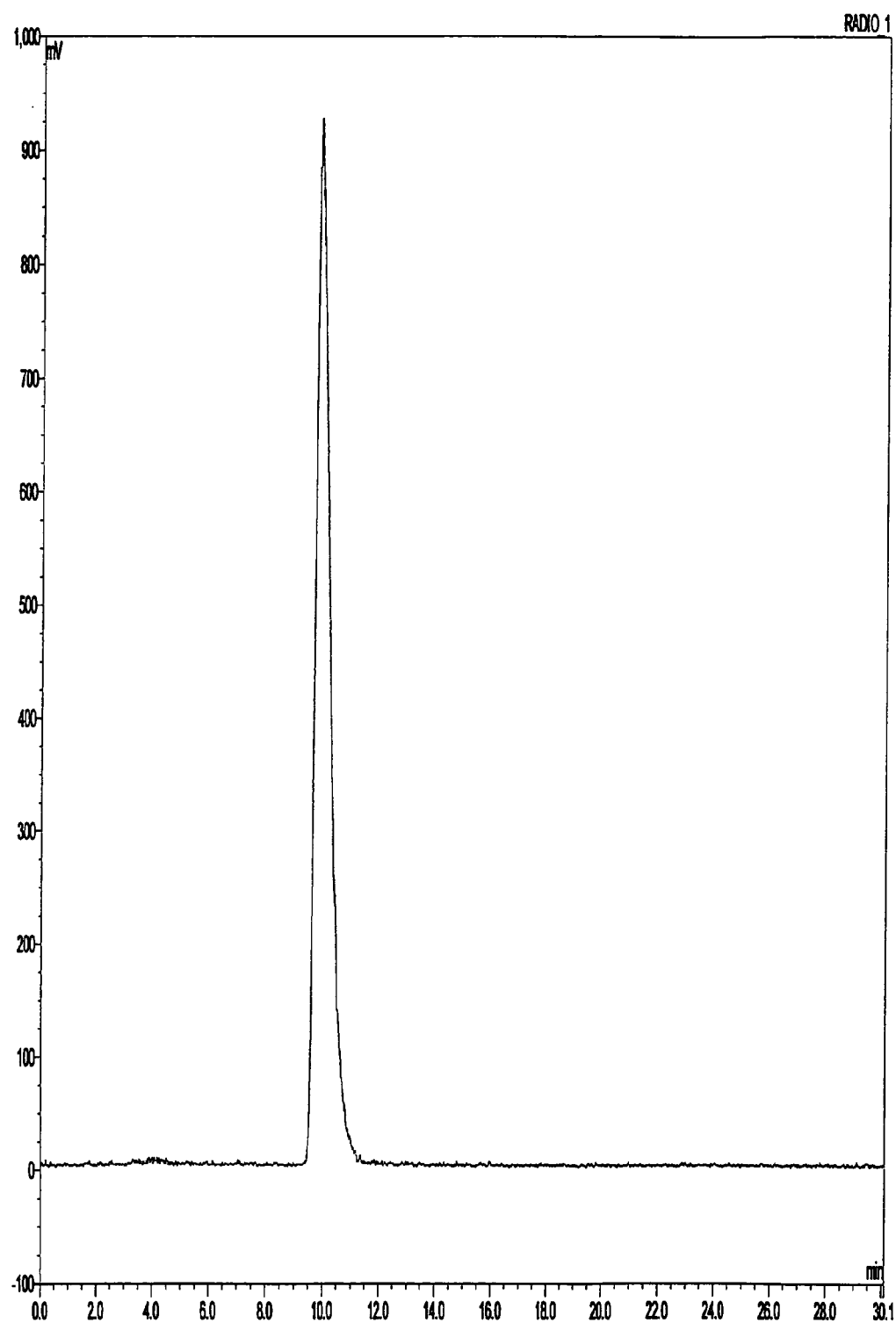
FIGS. 9 and 10 show the HPLC traces obtained using the above analytical achiral method for the PET tracer of the invention and its alternative enantiomer, respectively.
Figure 10:
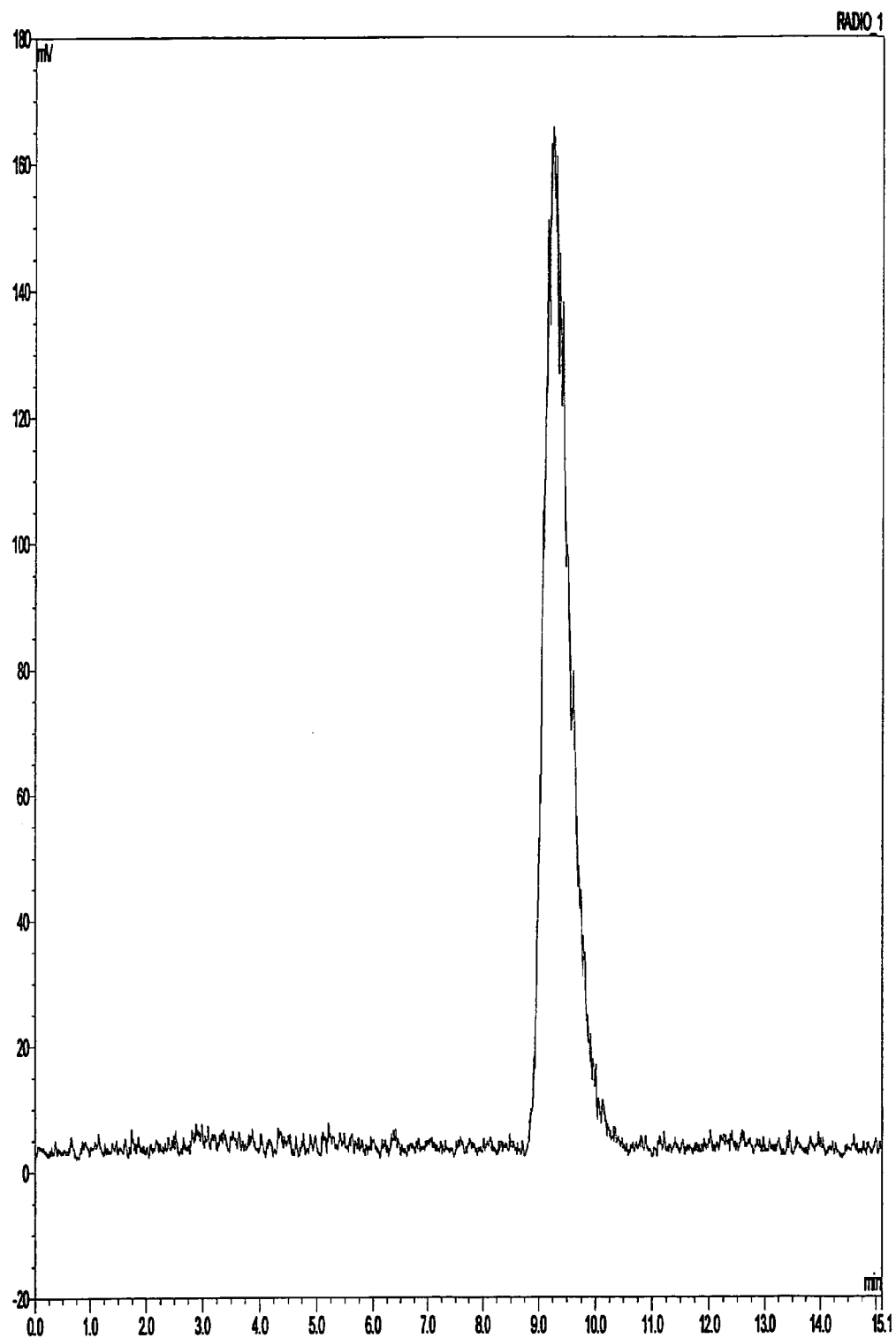

FIGS. 9 and 10 show the HPLC traces obtained using the above analytical achiral method for the PET tracer of the invention and its alternative enantiomer, respectively.

Analytical chiral HPLC was carried out as follows:

| | |
|---|---|
| 0-10 mins | 20% (B) |
| Column | Chiralpak IC 250 × 4.6 mm and Chiralpak IC guard column |
| Eluent | Methanol (pump A):Isopropyl alcohol (pump B) |
| Loop Size | 10 ul |
| Pump speed | 1 ml/min, |
| Wavelength | 220, 230 nm |

Figure 11:
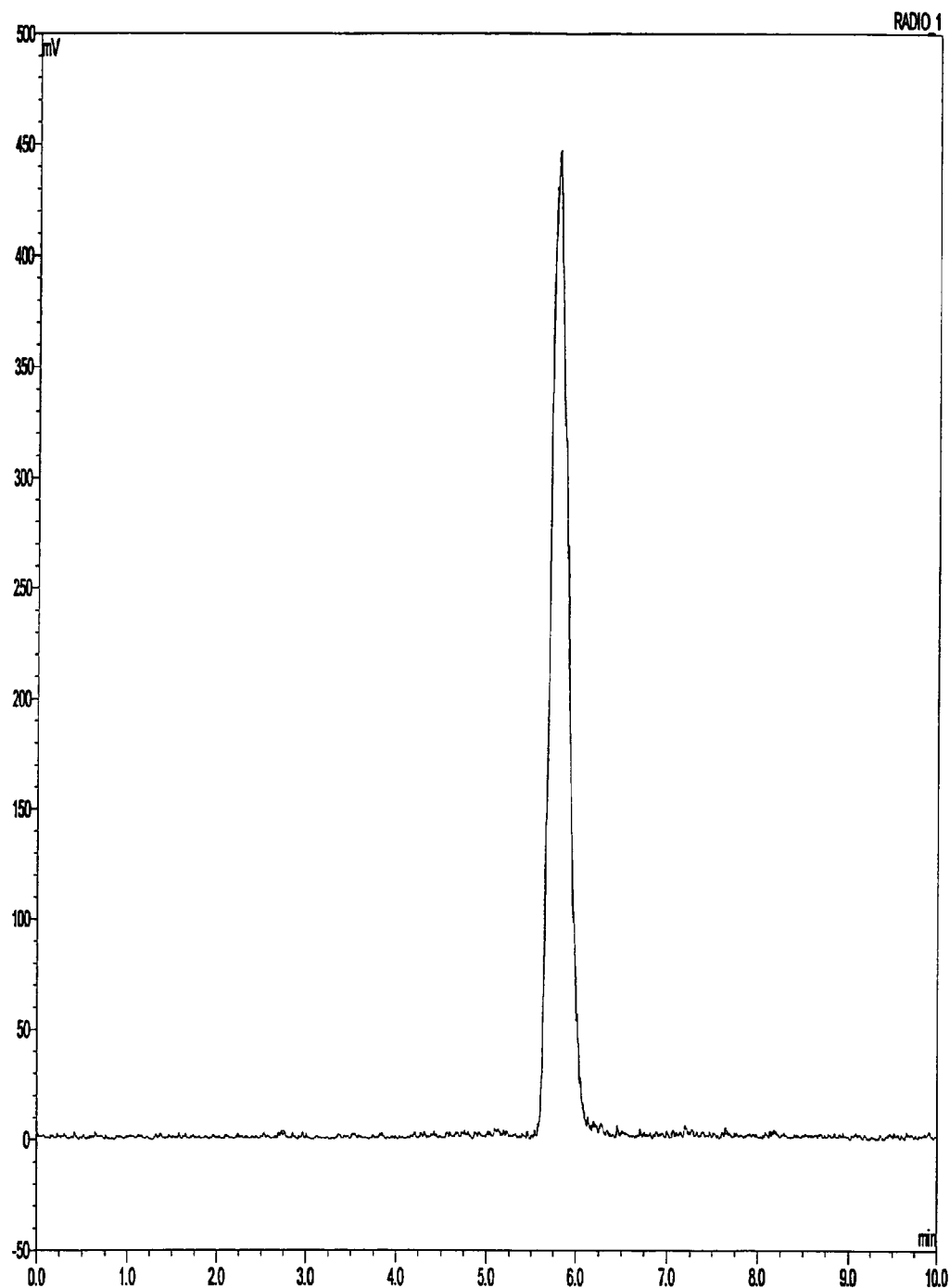
FIGS. 11 and 12 show the HPLC traces obtained using the above chiral HPLC method for the PET tracer of the invention and its alternative enantiomer, respectively.
Figure 12:
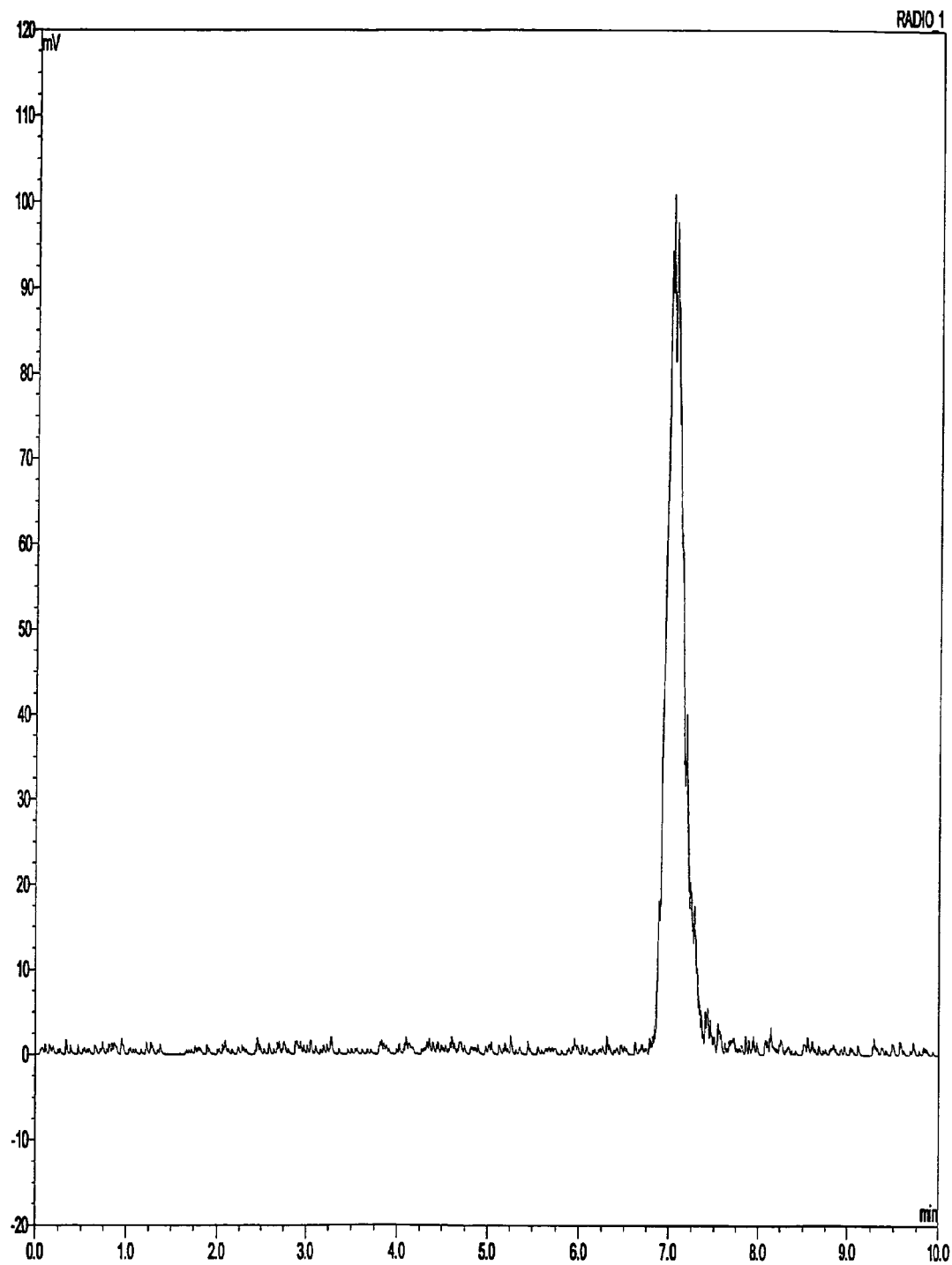

FIGS. 11 and 12 show the HPLC traces obtained using the above chiral HPLC method for the PET tracer of the invention and its alternative enantiomer, respectively.

The EOS yield for the PET tracer of the invention was 32%, and for its enantiomer was 19%.

Example 14

Synthesis of the Non-radioactive Version of the (S) and (R) Enantiomers of Imaging Agent 5

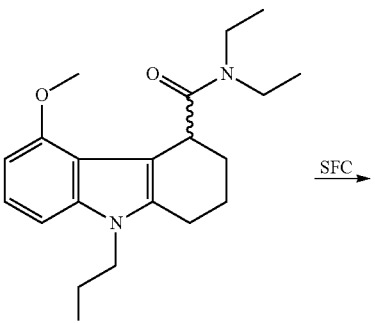

Non-radioactive imaging agent 5

$\xrightarrow{\text{SFC}}$

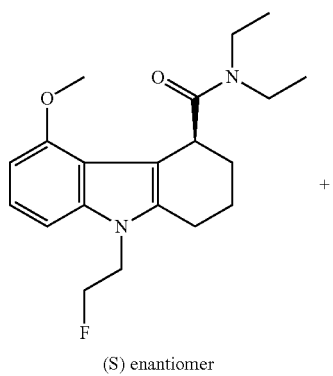

(S) enantiomer

+

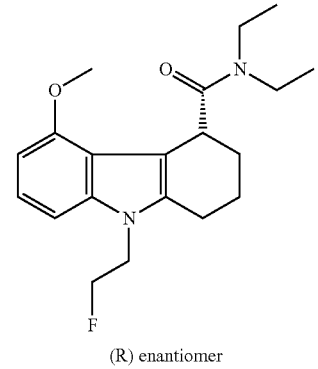

(R) enantiomer

Non-radioactive imaging agent 5 (obtained as described in Example 2) was separated into its enantiomers using chiral supercritical fluid (CO₂) chromatography (SFC) on a Kromasil Amycoat, 250×10 mm, 5 μm, 100 Å column using 20% IPA at 40° C. at 14 ml a min with a run time of 6 min. 100 mg of the racemic mixture was dissolved in 1,4-Dioxane (2.5 ml) and up to 200 μl at a time was as injected for each run. The fractions were cut by time to ensure that no mixed fractions were collected. Analytical HPLC determination of the enantiomeric purity of the two separated enantiomers on an IC from Chiral Technologies, 250×4.6 mm, 5 μm, run isocratic, 80:20—MeOH:IPA at 0.5 ml/min and room temperature indicated an enantiomeric purity of 99.5% of each of the enantiomers.

Example 15

In Vitro Potency Assay

Affinity for PBR was screened using a method adapted from Le Fur et al (Life Sci. 1983; USA 33: 449-57). Non-radioactive analogues of in vivo imaging agents of the invention were tested.

Each test compound (dissolved in 50 mM Tris-HCl, pH 7.4, 10 mM $MgCl_2$ containing 1% DMSO) competed for binding to Wistar rat heart PBR against 0.3 nM [$^3$H]PK-11195. The reaction was carried out in 50 mM Tris-HCl, pH 7.4 10 mM $MgCl_2$ for 15 minutes at 25° C. Each test compound was screened at 6 different concentrations over a 300-fold range of concentrations around the estimated $K_i$. The following data were observed:

| Imaging Agent | Ki (nM) |
|---|---|
| 5 | 1.47 |
| (S)-5 | 0.87 |
| (R)-5 | 3.87 |
| 6 | 18.30 |
| 7 | 1.25 |
| 9 | 3.79 |
| 10 | 7.62 |
| 11 | 2.12 |

Example 16

In Vivo Biodistribution Method

Imaging agents of the invention were tested in an in vivo biodistribution model.

Adult male Wistar rats (200-300 g) were injected with 1-3 MBq of test compound via the lateral tail vein. At 2, 10, 30 or 60 min (n=3) after injection, rats were euthanised and tissues or fluids were sampled for radioactive measurement on a gamma counter.

The following data of note were observed:

| Imaging Agent | Brain 2 min (% ID/g) | OB 30 min (% ID/g) | OB:Str 30 min |
|---|---|---|---|
| 5 | 0.52 | 0.36 | 3.00 |
| (S)-5 | 0.53 | 0.45 | 3.20 |
| (R)-5 | 0.53 | 0.23 | 2.90 |
| 6 | 0.51 | 0.25 | 2.50 |
| 7 | 0.55 | 0.34 | 3.40 |
| 9 | 0.56 | 0.41 | 3.72 |
| 10 | 0.50 | 0.51 | 3.19 |
| 11 | 0.51 | 0.42 | 3.50 |

% ID/g: percentage of injected dose per gram;
OB: olfactory bulb;
Str: striatum

FIGS. 13-18 illustrate the biodistribution profile in the brain imaging agents 5-8, 10 and 11, respectively. It can be seen that the in vivo imaging agents of the present invention have good brain uptake and improved specific uptake in PBR-expressing tissues.

What is claimed is:

1. A method for the identification and/or monitoring of cancer in a subject wherein said cancer is characterised by abnormal expression of peripheral benzodiazepine receptors (PBR) and with the proviso that said cancer is not colon cancer, prostate cancer, breast cancer or colorectal carcinoma, wherein said method comprises the following steps:

(a) administering to said subject an in vivo imaging agent of Formula I:

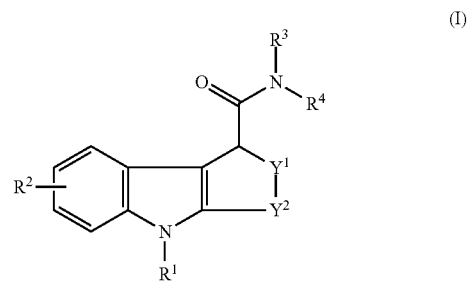

wherein:
$R^1$ is $C_{1-3}$ alkyl or $C_{1-3}$ fluoroalkyl;
$R^2$ is hydrogen, hydroxy, halo, cyano, $C_{1-3}$ alkyl, $C_{1-3}$ alkoxy, $C_{1-3}$ fluoroalkyl, or $C_{1-3}$ fluoroalkoxy;
$R^3$ and $R^4$ are independently $C_{1-3}$ alkyl, $C_{7-10}$ aralkyl, or $R^3$ and $R^4$, together with the nitrogen to which they are attached, form a nitrogen-containing $C_{4-6}$ aliphatic ring optionally comprising 1 further heteroatom selected from nitrogen, oxygen and sulfur;
$Y^1$ is O, S, SO, $SO_2$ or $CH_2$; and,
$Y^2$ is $CH_2$, $CH_2$—$CH_2$, $CH(CH_3)$—$CH_2$ or $CH_2$—$CH_2$—$CH_2$;
and wherein said in vivo imaging agent of Formula I comprises an atom which is a radioisotope suitable for in vivo imaging;

(b) allowing said administered in vivo imaging agent of step (a) to bind to PBR expressed in said subject;

(c) detecting signals emitted by the radioisotope comprised in said bound in vivo imaging agent of step (b) using a suitable in vivo imaging procedure;

(d) generating an image representative of the distribution and/or extent of said signals detected in step (c);

(e) determining the distribution and/or extent of PBR expression in said subject wherein said expression is directly correlated with the distribution and/or extent of said signals as represented in said image generated in step (d); and, (f) using the distribution and extent of PBR expression as determined in step (e) in the identification and/or monitoring of said cancer.

2. The method as defined in claim 1 wherein said in vivo imaging agent is administered as a radiopharmaceutical composition comprising said in vivo imaging agent together with a pharmacologically-acceptable carrier.

3. The method as defined in claim 1 wherein said radioisotope suitable for in vivo imaging is selected from $^{11}$C, $^{18}$F and $^{123}$I.

4. The method as defined in claim 1 wherein $R^1$ of Formula I is methyl or $C_{2-3}$ fluoroalkyl.

5. The method as defined in claim 1 wherein $R^2$ of Formula I is hydrogen, halo, $C_{1-3}$ alkoxy or $C_{1-3}$ fluoroalkoxy.

6. The method as defined in claim 1 wherein $R^3$ and $R^4$ of Formula I are independently methyl, ethyl or benzyl.

7. The method as defined in claim 1 wherein $R^3$ and $R^4$ of Formula I, together with the nitrogen to which they are attached, form a nitrogen-containing $C_{5-6}$ aliphatic ring.

8. The method as defined in claim 1 wherein $Y^1$ of Formula I is $CH_2$.

9. The method as defined in claim 1 wherein $Y^2$ of Formula I is $CH_2$—$CH_2$.

10. The method as defined in claim 1 wherein said in vivo imaging agent is of Formula Ia:

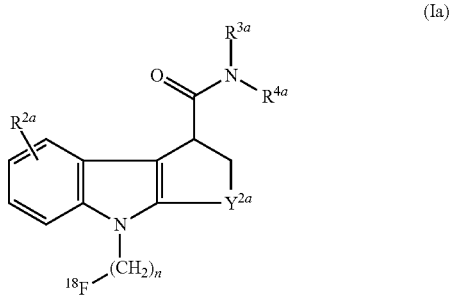

(Ia)

wherein:

$R^{2a}$ is hydrogen, halo or $C_{1-3}$ alkoxy;

$R^{3a}$ and $R^{4a}$ are independently methyl, ethyl or benzyl, or together with the nitrogen to which they are attached form a pyrrolidinyl, piperidinyl, azepanyl, or morpholinyl ring;

$Y^{2a}$ is as defined in claim 1 for $Y^2$; and;

n is 1, 2 or 3.

11. The method as defined in claim 10 wherein for Formula Ia:

$R^{3a}$ and $R^{4a}$ are both ethyl or $R^{3a}$ is methyl and $R^{4a}$ is benzyl, or together with the nitrogen to which they are attached form an azepanyl ring;

$R^{2a}$ is hydrogen, methoxy or fluoro;

$Y^{2a}$ is $CH_2$—$CH_2$ or $CH(CH_3)$—$CH_2$; and, n is 2.

12. The method as defined in claim 11 wherein said in vivo imaging agent is of the following chemical structure:

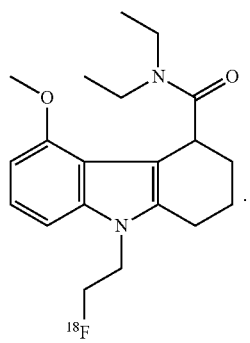 [SMILES: CCN(CC)C(=O)C1CCCc2c1c1c(OC)cccc1n2CC[18F]]

13. The method as defined in claim 12 wherein said in vivo imaging agent is the purified enantiomer having the following chemical structure:

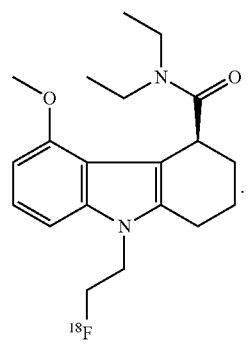 [SMILES: CCN(CC)C(=O)[C@H]1CCCc2c1c1c(OC)cccc1n2CC[18F]]

14. The method as defined in claim 1 which is carried out repeatedly during the course of a treatment regimen for said subject, said regimen comprising administration of a drug to combat a cancer wherein said cancer is as defined in claim 1.

15. The method as defined in claim 1 wherin said cancer is selected from glioma, astrocytoma, ovarian cancer, hepatocarinona, fibrosarcoma and oral cancer.

* * * * *